(12) United States Patent
Lee et al.

(10) Patent No.: US 6,972,130 B1
(45) Date of Patent: Dec. 6, 2005

(54) BIOCERAMIC COMPOSITIONS

(75) Inventors: Dosuk D. Lee, Brookline, MA (US); Christian Rey, Castanet (FR); Maria Aiolova, Brookline, MA (US); Aliassghar Tofighi, Belmont, MA (US)

(73) Assignee: Etex Corporation, Cambridge, MA (US)

( * ) Notice: Subject to any disclaimer, the term of this patent is extended or adjusted under 35 U.S.C. 154(b) by 0 days.

(21) Appl. No.: 09/284,436

(22) PCT Filed: Oct. 16, 1997

(86) PCT No.: PCT/US97/18528

§ 371 (c)(1),
(2), (4) Date: Jun. 8, 2000

(87) PCT Pub. No.: WO98/16209

PCT Pub. Date: Apr. 23, 1998

Related U.S. Application Data

(63) Continuation-in-part of application No. 08/729,354, filed on Oct. 16, 1996, now Pat. No. 6,132,463, and a continuation-in-part of application No. 08/729,342, filed on Oct. 16, 1996, now Pat. No. 6,541,037.

(51) Int. Cl.$^7$ .................................................. A61F 2/00
(52) U.S. Cl. ........................ 424/426; 424/422; 424/423; 424/600; 424/601; 424/602
(58) Field of Search ................................ 424/422, 423, 424/426, 600, 601, 602

(56) References Cited

U.S. PATENT DOCUMENTS

| 4,157,378 A | 6/1979 | Tomlinson et al. |
| 4,346,709 A | 8/1982 | Schmitt |
| 4,347,234 A | 8/1982 | Wahlig et al. |
| 4,429,691 A | 2/1984 | Niwa et al. |
| 4,612,053 A | 9/1986 | Brown et al. |

(Continued)

FOREIGN PATENT DOCUMENTS

| EP | 0 268 463 | 5/1988 |
| EP | 0347028 | 11/1989 |

(Continued)

OTHER PUBLICATIONS

Aoki, "Science and medical applications of hydroxyapatite", *JAAS*, 11–15, 1991.

(Continued)

*Primary Examiner*—Shelley A. Dodson
*Assistant Examiner*—Konata M. George
(74) *Attorney, Agent, or Firm*—Clark & Elbing LLP; Paul T. Clark

(57) ABSTRACT

The present invention provides a synthetic, poorly crystalline apatite (PCA) calcium phosphate containing a biologically active agent and/or cells (preferably tissue-forming or tissue-degrading cells). The compositions provided by the present invention are useful for a variety of in vivo and in vitro applications, including drug delivery (for example, to bony sites, the central nervous system, intramuscular sites, subcutaneous sites, interperitoneal sites, and occular sites) tissue growth (preferably bone or cartilage) osseous augmentation, and methods of diagnosing disease states by assaying tissue forming potential of cells isolated from a host. The invention also provides methods of preparing delivery vehicles, of altering delivery vehicle characteristics, and of delivering biologically active agents to a site. The invention further provides in vitro cell culture systems and cell encapsulation materials. The invention is useful for both medical and veterinary applications.

18 Claims, 22 Drawing Sheets

U.S. PATENT DOCUMENTS

| | | | |
|---|---|---|---|
| 4,684,673 A | 8/1987 | Adachi | |
| 4,737,411 A | 4/1988 | Graves, Jr. et al. | |
| 4,842,603 A | 6/1989 | Draenert | |
| 4,849,193 A | 7/1989 | Palmer et al. | |
| 4,880,610 A | 11/1989 | Constantz | |
| RE33,161 E | 2/1990 | Brown et al. | |
| 4,917,702 A | 4/1990 | Scheicher et al. | |
| RE33,221 E | 5/1990 | Brown et al. | |
| 4,938,938 A | 7/1990 | Ewers et al. | |
| 4,959,104 A | 9/1990 | Lino et al. | |
| 5,034,059 A | 7/1991 | Constantz | |
| 5,037,639 A | 8/1991 | Tung | |
| 5,047,031 A | 9/1991 | Constantz | |
| 5,053,212 A | 10/1991 | Constantz et al. | |
| 5,085,861 A | 2/1992 | Gerhart et al. | |
| 5,129,905 A | 7/1992 | Constantz | |
| 5,149,368 A | 9/1992 | Liu et al. | |
| 5,152,836 A | 10/1992 | Hirano et al. | |
| 5,164,187 A | 11/1992 | Constantz et al. | |
| 5,178,845 A | 1/1993 | Constantz et al. | |
| 5,197,985 A | 3/1993 | Caplan et al. | |
| 5,226,914 A | 7/1993 | Caplan et al. | |
| 5,262,166 A | 11/1993 | Liu et al. | |
| 5,279,831 A | 1/1994 | Constantz et al. | |
| 5,281,265 A | 1/1994 | Liu | |
| 5,286,763 A | 2/1994 | Gerhart et al. | |
| 5,336,264 A | * 8/1994 | Constanz et al. | 424/423 |
| 5,342,441 A | 8/1994 | Mandai et al. | |
| 5,352,715 A | 10/1994 | Wallace et al. | |
| 5,399,665 A | 3/1995 | Barrera et al. | |
| 5,470,803 A | 11/1995 | Bonfield et al. | |
| 5,486,359 A | 1/1996 | Caplan et al. | |
| 5,496,399 A | 3/1996 | Ison et al. | |
| 5,514,378 A | 5/1996 | Mikos et al. | |
| 5,516,532 A | 5/1996 | Atala et al. | |
| 5,522,893 A | 6/1996 | Chow et al. | |
| 5,525,148 A | 6/1996 | Chow et al. | |
| 5,542,973 A | 8/1996 | Chow et al. | |
| 5,545,254 A | 8/1996 | Chow et al. | |
| 5,565,502 A | 10/1996 | Glimcher et al. | |
| 5,605,713 A | 2/1997 | Boltong | |
| 5,665,120 A | 9/1997 | Ohtsuka et al. | |
| 5,691,397 A | 11/1997 | Glimcher et al. | |
| 5,700,289 A | 12/1997 | Breitbart et al. | |
| 6,132,463 A | * 10/2000 | Lee et al. | 600/36 |

FOREIGN PATENT DOCUMENTS

| | | |
|---|---|---|
| EP | 0664133 | 7/1995 |
| JP | 63111875 | 5/1988 |
| JP | 63170205 | 7/1988 |
| JP | 2-182261 | 7/1990 |
| JP | 5-305134 | 11/1993 |
| JP | 06228011 | 8/1994 |
| JP | 7277712 | 10/1995 |
| WO | WO 92/02453 | 7/1991 |
| WO | WO 92/00109 | 1/1992 |
| WO | WO 94/04657 | 8/1993 |
| WO | WO 94/02412 | 2/1994 |
| WO | WO 94/20064 | 9/1994 |
| WO | WO 95/08319 | 9/1994 |
| WO | WO 96/36562 | 5/1996 |
| WO | WO 97/17285 | 11/1996 |

OTHER PUBLICATIONS

Appel et al., "Oncologic, Endocrine & Metabolic—Overview—Recent advances in implants for bone growth promotion", *Exp. Opin. Ther. Patents*, 4(12):1461–1469, 1994.

Atala et al., "Injectable alginate seeded with chondrocytes as a potential treatment for vesicoureteral reflux", *J. Urol.*, 150:745, 1993.

Athanasou et al., "Current Concepts Review: Cellular Biology of Bone Resorbing Cells", *J. Bone and Joint Surg.*, 78–A:1096–1112, 1996.

Barton, et al., "Surface and bulk properties of amorphous calcium phosphate" Colloid Interface Sci. [Proc. Int. Conf.], $50^{th}$ 371 (1976) [CA 87:73954v].

Benghuzzi et al., "Alcap ceramic implantable devices and the effect of surface area on the delivery of various steroid hormones", Abstract, Eighth Southern Biomedical Engineering Conference Richmond, VA, Oct. 15–16, 1989; Biomater. Artif. Cells Artif. Organs, 17:464, 1989.

Benghuzzi et al., "Controlled release of hydrophilic compounds by resorbable and biodegradable ceramic drug delivery devices", Biomed, Sci. Instrum., 28:179–182, 1992.

Benghuzzi et al., "Resorbable and biogradable ceramics as drug delivery systems", Abstract, *Eighth Southern Biomedical Engineering Conference Richmond, VA, Oct. 15–16, 1989; Biomater. Artif. Cells Artif. Organs*, 17:463, 1989.

Benghuzzi, et al., "Long–term delivery of Danazol by biogradable ceramic devices", Abstract, *Eighth Southern Biomedical Engineering Conference Richmond, VA, Oct. 15–16, 1989; Biomater. Artif. Cells Artif. Organs*, 17:465, 1989.

Besic et al., "Electron probe microanalysis of noncarious enamel and dentin and calcified tissues in mottled teeth", *J. Dent. Res.*, 48:131, (Jan.–Feb., 1969).

Blumenthal et al., "Effect of Preparation Conditions on the Properties and Transformation of Amorphous Calcium Phosphate", *Mat Res. Bull.*, 7(11):1181 (Nov. 1972).

Boskey, Adele, "Matrix Proteins and Mineralization: An Overview", *Connect Tissue Res.*, 35:(1–4):357–63, 1996.

Cannon et al., "Continuous delivery of azidothymidine by hydroxyapatite or tricalcium phosphate ceramics", *Biomed. Sci. Instrm.* 31:159–164, 1995.

Chu et al., "Articular cartilage repair using allogeneic perichondrocyte–seeded biodegradable porous polylactic acid (PLA): a tissue–engineering study", *J. Biomed. Mater. Res.*, 29:1147, 1995.

Chung, et al., "Biological effects of drug–loaded biodegradable membranes for guided bone regeneration" *J. Periodont. Res.*, 32:172–175. 1997.

Clarke, et al., "Non–sterodial Anti–Inflammatory Drug Induced Differentiation of Bone Marrow Stromal Cells" $43^{rd}$ Annual Meeting, Ortho Res. Soc., San Francisco, CA, 574. Feb. 9–13, 1997.

Constantz et al., "Skeletal repair by in situ formation of the mineral phase of bone", *Sci.*, 267:1976, 1995.

Dennissen, et al., "New–shaped hysroxyapatite implants for release of agents modulating periodontal–like tissues" *J. Periodont. Res.*, 32:40–46, 1997.

Driessens et al., "Calcium Phosphate bone Cements" *Encycl. Hndbk. Of Biomat. And Bioeng.*, Wise (EDS) NY, Marcel Dekker, 1995.

Ducheyne et al., "Bioceramic Composites", Chapter 15 from "An Introduction to Bioceramics, Advanced Series in Ceramics", vol. I.

Eanes et al., "Intermediate states in the precipitation of hydroxyapatite", *Nature*, 208:365–367, Oct. 23, 1965.

Eanes et al. "Intermediate phases in the basic solution preparation of alkaline earth phosphates" *Calcif. Tiss. Res.*, 2(1):38 (1968)[CA 69:110373f].

Eanes et al., "Thermochemical studies on amorphous calcium phosphate", *Calc. Tiss. Res.*, 5:133, 1970.

Etex (D. Knaack) "Endothermically Setting Calcium Phosphate Bone Substitute" Orthop. Cong. Aug. 20–22, 1997, Boston, MA.

Etex (Knaack et al) "Novel Fully Resorbable Calcium Phosphate Bone Substitute" 1997 *ASBMR Abstract*, vol. 12, Supplement 1:202 Aug., 1997.

Etex (Knaack et al) "A Fully Resorbable Calcium Phosphate Bone Substitute" *Portland Bone Symp.*, 1997.

Fabbri et al., "Hydroxyapatite–based porous aggregates: physico–chemical nature, structure, texture and architecture", *Biomat.*, 16:225–228, 1995.

Glimcher et al., "Recent studies of bone mineral: Is the amorphous calcium phosphate theory valid?", *J. of Cryst. Growth*, 53:100–119, 1981.

Glimcher et al., "Recent studies of the mineral phase in bone and its possible linkage to the organic matrix by protein–bound phosphate bonds", *Phil. Trans. R. Soc. Lond.*, B 304:479–508, 1984.

Graves et al., "Resorbable ceramic implants", *J. Biomed. Mater. Res. Symp.*, No. 2 (part 1), 9–115, 1971.

Greenfield et al., "Formation chemistry of amorphous calcium phosphates prepared from carbonate containing solutions", *Calc. Tiss. Res.*, 9:152, 1972.

Hirasawa et al., "Manufacture of high purity hydroxyapatite", Chem. Abstr., 108(10): 166, No. 78193h (Mar. 7, 1988).

Holmes, et al., "Surface areas by gas adsorption on amorphous calcium phosphate and crystalline hydroxyapatite", *Calc. Tiss. Res.*, 7:163, 1971.

Hubbell, "Biomaterials in tissue engineering", *Bio/Tech.*, 13:56, 1995.

Ijnterna et al., "Hydroxyapatite microcarriers for biocontrolled release of protein drugs", *Int'l J. of Pharm.*, 112:215, 1994.

Ikada et al., "Release of antibodic from composites of hydroxyapatite and poly(lactic acid)", J. of Controlled Rel., 2:179–186, 1985.

Itokazu et al., "Drug delivery systems using porous hydroxyapatite blocks", J. Ortho. Surg., 2(2):47–50, 1994.

Ishikawa et al., "Effects of preparation in aqueous solution on properties of hydroxyapatites" *Dent. Mater. J.*, 9(1):58 (1990) [CA 113:218168j].

Jang, B.Z., "Advanced Polymer Composites", Ch. 1, Intro., *The Mater. Info. Soc.*

Kim et al., "Effect of Recombinant Human (1–84) Parathyroid Hormone on Fracture Healing In Ovariectomized Rats" $43^{rd}$ Annual Meeting, orthopaidic Research Society, San Francisco, CA, 181–31, Feb. 9–13, 1997.

Labarthe et al., "Sur la structure et les propiétés des apatites carbonatées de type B phospho–calciques", *Ann. Chem.*, 8:289, 1973.

Mileti, et al., "Development of a Hydroxyapatite ceramic matrix for the continuous delivery of coumadin", *Biomed. Sci. Instrm.*, 31:179–182, 1995.

Moldovan et al., "Continuous delivery of analgesics by ceramics", Abstract, *Fifth World Biomaterials Congress*, Toronto, Canada, Jun. 2, 1996.

Moldavan et al., "A ceramic system for continuous release of acetylsalicylic acid", *Biomed. Sci. Instrm.* 30:175–180, 1994.

Nolan, et al., "Calcium hydroxyapatite ceramic delivery system", *J. Bone and Joint Surg.*, 75–13:334, 1993.

Norian, et al., "The Material Science of Norian SRS, Skeletal Repair System."

Nylen, et al., "Molecular and ultrastructural studies of non–crystalline calcium phosphates", Calc. Tiss. Res., 9:95, 1972.

Onodera et al., "Identification of Macrophage Migration Inhabitory Factor in Murine Neonatal Calvariae and Osteoblasts" $43^{rd}$ *Annual Meeting, Orthopaedic Research Society, San Francisco*, CA, 322, Feb. 9–13, 1997.

Otsuka et al., Effect of particle size of metastable calcium phosphates on mechanical strength of a novel self–setting bioactive calcium phosphate cement, *J. of Biomed. Mater. Res.*, 29:25–32, 1995.

Otsuka et al., "A novel skeletal drug–delivery system using self–setting calcium phosphate cement. 4. Effects of the mixing solution volume on anticancer drug release from homogeneous drug–loaded cement", *J. of Pharm. Sci.*, 84(6), Jun. 1995.

Otsuka et al., "A novel skeletal drug–delivery system using self–setting calcium phosphate cement. 4. Effects of the mixing solution volume on the drug–release rate of heterogeneous aspirin–loaded cement", *J. of Pharm. Sci.*, 83(2), Feb. 1994.

Pool, "Coral chemistry leads to human bone repair", *Sci.*, 269:1772 (Mar., 1995).

Posner et al., "Synthetic amorphous calcium phosphate and its relation to bone mineral structure", *Bone Min. Struc.*, 8:273–281, 1975.

Rey, et al., "Structural studies of the mineral phase of calcifying cartilage", *J. Bone Min. Res.*, 6:515, 1991.

Rey et al., "Chemical Properties of Poorly Crystalline Apatites" *Phosphorus Res. Bull.* 6:67–70 (1996) abstract only.

Rey et al., "The carbonate environment in bone mineral: a resolution–enhanced fourier transform infrared spectroscopy study", *Calcif. Tiss. Int.*, 45:157, 1989.

Rey et al., "Preparation of Microporous Ceramic at Low Temperature from Poorly Crystalline Apatite" *Symposium Abstract*, 1993.

Roodman, D.G., "Advances in Bone Biology: The Osteoclast", Endo. Rev., 17(4):308–332, 1996.

Shinto, et al., "Calcium hydroxyapatite ceramic used as a delivery system for antibiotics", J. of Bone and Joint Surg., 74B(4):600–604, Jul. 1992.

Shors et al., "porous hydroxyapatite" in An Introduction to Bioceramics (Hersch et al., eds), Work Sci. Publ. Co. Pte. Ltd., 1993.

Suzuki, et al., "Identification Macrophage Migration Ingibitory Factor in Murine Neonatal Clavariae and Osteoblast", $43^{rd}$ *Ann. Mtg., Orthop. Res. Soc., Feb. 9–13, 1997, San Francisco, CA.*

Termine, et al., "Amorphous/Crystalline Interrelationships in Bone Mineral", Calc. Tiss. Res. 1, 8–23, 1967.

Thoma, et al., "Biodegradable controlled release implants based on β–tricalcium phosphate ceramic", *Eur. J. Pharm. Biopharm.*, 38(3):107–112, 1992.

Thoma, et al., "Biodegradable Gentamicin–Depotimplantate aus β–tricalcium–phosphatkeramik", *Pharmazie*, 46, 1991.

Thomson et al, "Fabrication of biogradable polymer scaffolds to engineer trabecular bone", *J. Biomat. Sci. Polymer Edn.*, 7:23, 1995.

Tona, et al., "Derivatized hyaluronic acid films support mesenchymal stem cell attachment and proliferation", *Fifth*

*World Biomat. Cong., May 29–Jun. 2, 1996, Toronto, Canada*.

Tormala, "Biodegradable self–reinforced composite materials; manufacturing structure and mechanical properties", *Clin. Mat.* 10:29, 1992.

Tung, et al., "An intermediate state in hydrolysis of amorphous calcium phosphate", Calcif. Tissue Int., 35:783, 1983.

Tung et al., "In vitro drug release of antibiotic–loaded porous hydroxyapatite cement", *Art. Cell, Blood Subs., and Immob. Biotech.*, 23(1), p. 81–88, 1995.

Uchida et al., "Slow release of anticancer drugs from porous calcium hydroxyapatite ceramic", *J. of Ortho. Res.*, 10:440–445, 1992.

Van Valkenburg, J., *"Biological bone graft substitute helps body heal itself", Commercial Appeal*, B4 (Aug. 22, 1996).

Yasue, et al., "Effect of Adsorption of Succinic Acid on the Formation of Amorphous Calcium Phosphate," Journal of the Ceramic Society of Japan (Japanese Version), vol. 102, No. 12, pp. 1122–1127, 1994.*/1.

* cited by examiner

FIG. 4
(a) REACTIVE ACP
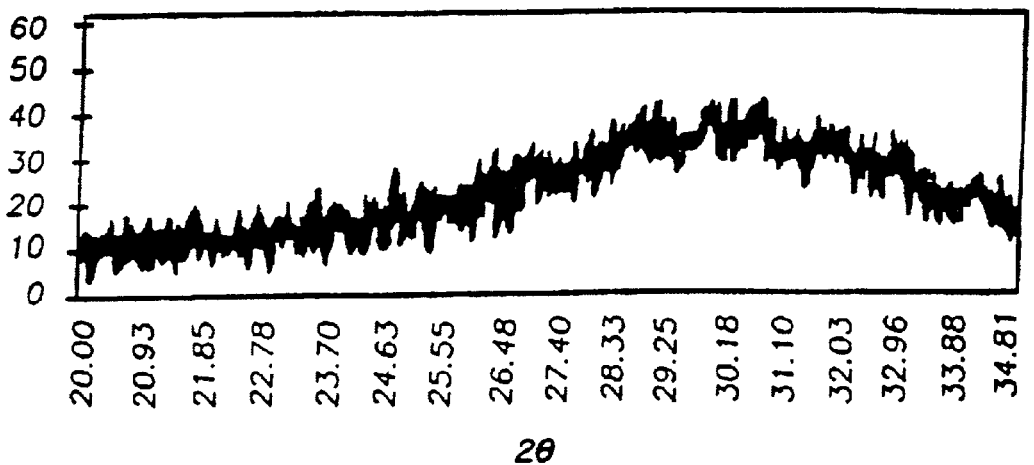
(b) DCDP
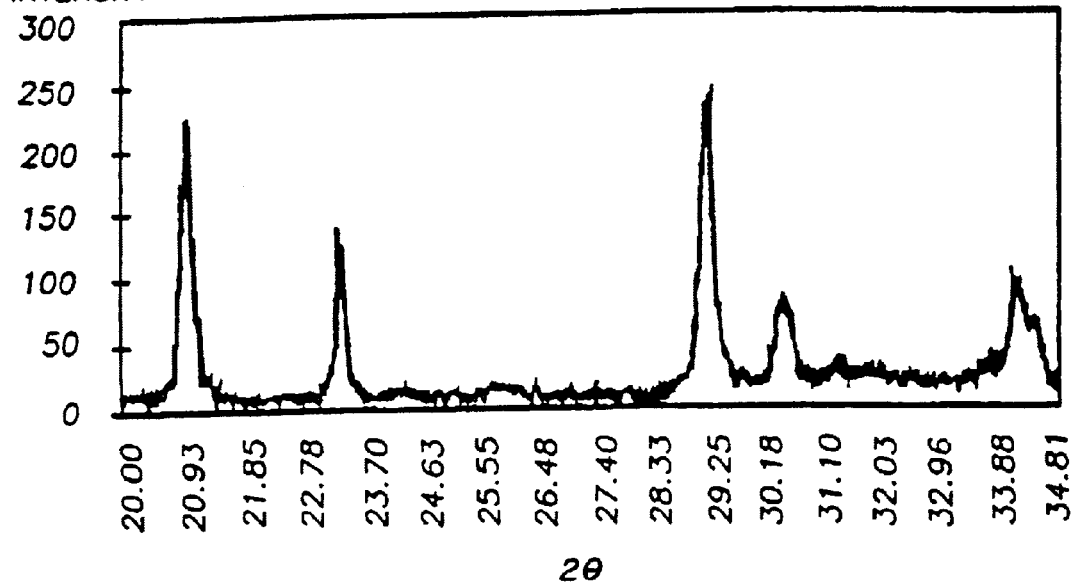

FIG. 6
(a)
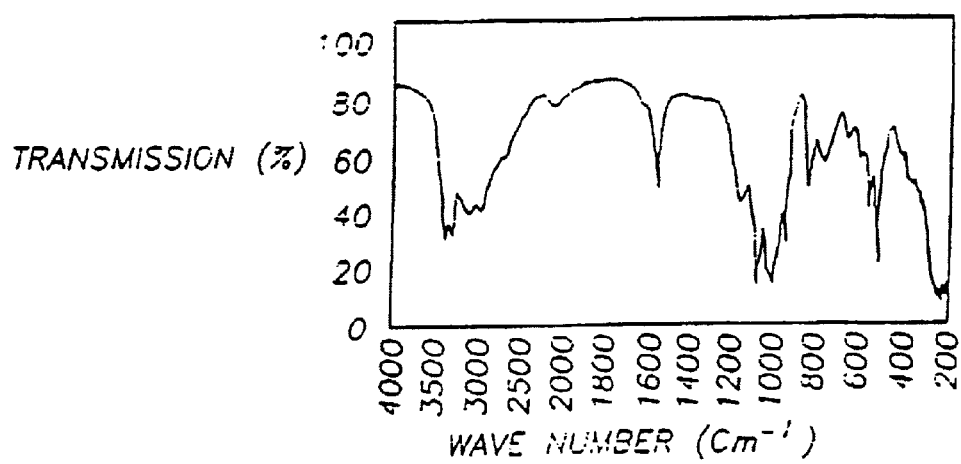
(b)
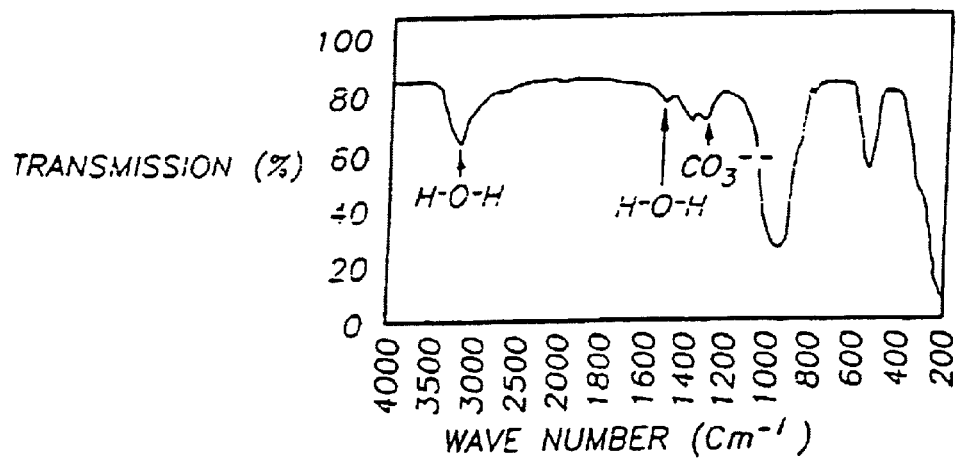
(c)
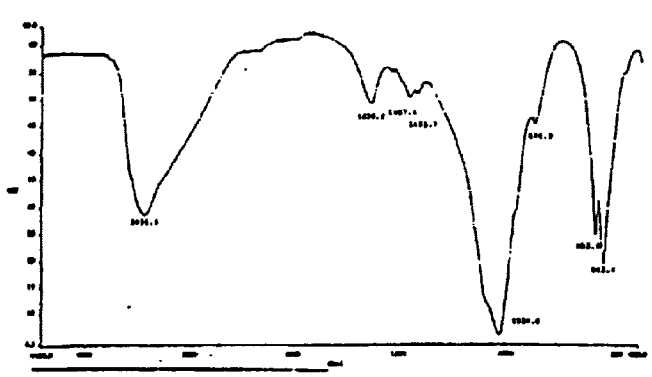

Study EX96-1-002
Bone Substitute Material (BSM™) Screening Assay in the NZW Rabbit Proximal Tibia Bone Defect Model Study EX96-1-002
Bone Substitute Material (BSM™) Screening Assay in the NZW Rabbit Proximal Tibia Bone Defect Model
FIG. 10⊃

Study EX95-1-004
Pilot Efficacy Study of Bone Substitute Material (BSM™) in the Canine Proximal Tibia Bone Defect Model

Photomicrograph of canine trabecular bone grown into the defect site treated with BSM. The small arrows denote osteoblast-like cells lining the bone spicules and are indicative of enhanced cellular activity. (Magnification 10X decalcified Hematoxylin & Eosin.

FIG. 11

Study EX95-1-004
Pilot Efficacy Study of Bone Substitute Material (BSM™) in the Canine Proximal Tibia Bone Defect Model

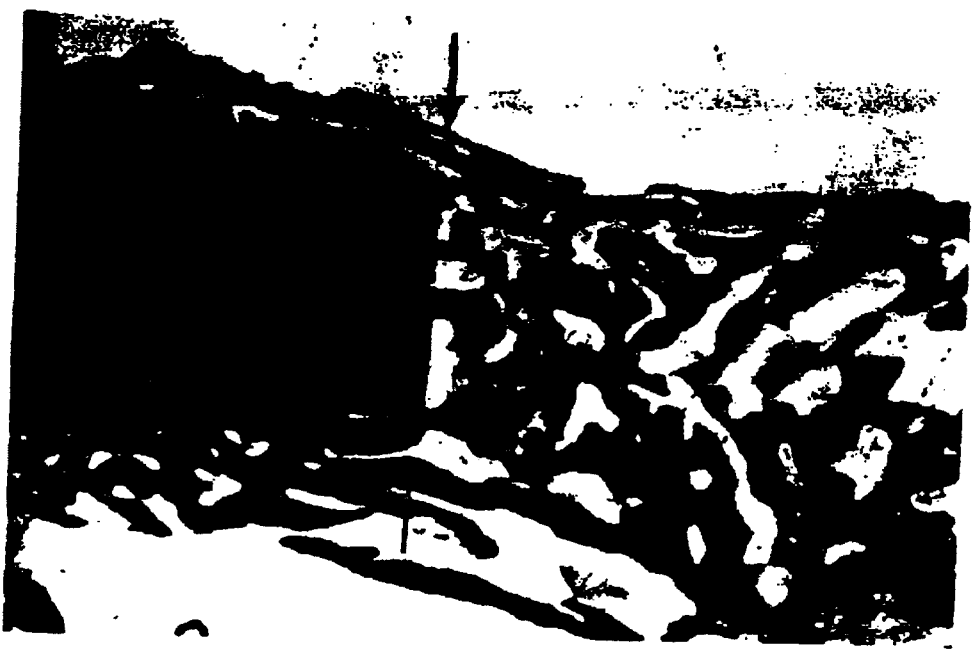

Photomicrograph of a canine cortical bone defect that was treated with BSM. The large arrows indicate one edge of the defect. The new bone growth is to the right of the defect and at 4 weeks after surgery is thick trabecular bone. (Magnification 4X undecalcified. Light Green Basic Fuchsin)

FIG. 12

Study EX95-1-005
Establishment of a Bone Substitute Material (BSM™) Screening Assay in the NZW Rabbit Proximal Tibia Bone Defect Model

Photomicrograph of an untreated (control) tibia defect in rabbit #31 at 4 weeks after surgery. The large arrow indicates the edge of the defect. The small arrowheads indicate the remaining defect with no bone. Small arrows denote an abundance of fibrous connective tissue in the defect site. The large arrowhead points to new trabecular bone in the defect. (Magnification 4X, decalcified Masson's Trichrome)

FIG. 13a

Study EX95-1-005
Establishment of a Bone Substitute Material (BSM™) Screening Assay in the NZW Rabbit Proximal Tibia Bone Defect Model

XRD ANALYSIS OF EXPLANTED α-BSM™ FOR DAYS 4,7,14

BIOCERAMIC COMPOSITIONS

This application is a 371 of PCT/US97/18528 filed Oct. 16, 1997, which is a continuation-in-part of Ser. No. 08/729,354 filed Oct. 16, 1996 now Pat. No. 6,132,463, and is a continuation-in-part of Ser. No. 08/729,342 filed Oct. 16, 1996 now U.S. Pat. No. 6,541,037.

BACKGROUND OF THE INVENTION

Much research in the area of bipharmaceutics is directed toward the development of effective implantable vehicles for drug delivery and other surgical applications. Such vehicles must be biocompatible and also must be capable of protecting the activity of any biologically active agent they are intended to delivery. Many biologically active agents are labile and easily lose activity when they are incorporated into a delivery material. Preservation of protein activity has posed particularly difficult problems.

In the drug delivery area, calcium phosphate ceramics have been studied as potential delivery vehicles due to their well known biocompatibility and their affinity for protein reagents (see, for example, IJntema et al., *Int. J. Pharm.* 112:215, 1994; Itokazu et al., *J. Orth. Surg.* 2:47, 1994; Shinto et al., *J. Bone Joint Surg.* 74-B:600, 1992; IJchida et al., *J. Orth. Res.* 10:440, 1992). However, the reaction employed to produce known calcium phosphate ceramic materials typically require elevated temperatures and/or pressures, and also require the presence of acids or bases. Because most biologically active agents would be destroyed by one or more of the conditions required to produce the ceramic, the biologically active agents can only be loaded in after the material is produced, which can limit the amount and type of agent that can be delivered.

Also, although a number of calcium phosphate materials have been referred to as "resorbable", such compounds, usually comprising or derived from tricalcium phosphate, tetracalcium phosphate or hydroxyapatite are in fact only weakly resorbable. Of the group, the tricalcium phosphate compounds have been demonstrated to be the most resorbable and, after many years of study, they are still not widely used in clinical settings. The tricalcium phosphates are known to have lengthy and somewhat unpredictable resorption profiles, generally requiring in excess of one year for resorption. Unless steps are taken to produce extremely porous or channeled tricalcium phosphates, these compounds are not replaced by bone. Recent studies have lead to the conclusion that the "biodegradation of TCP, which is higher than that of [hydroxyapatite], is not sufficient" (Berger et al., *Biomaterials,* 16:1241, 1995).

Tetracalcium phosphate and hydroxyapatite derived compounds are also only weakly resorbable. Published reports of tetracalcium phosphate fillers generally describe partial resorption over long periods of time. For example, as reported by Horioglu et al., it is not uncommon for such materials to require 30 months for 80% resorption (*Soc. for Biomaterials,* pg. 198, Mar. 18–22, 1995). Also, many reports that describe "resorption" of calcium phosphate materials do not actually demonstrate resorption because authors do not rule out, for example, migration of the vehicle from the implant site (see, for example, Ijntema et al., supra).

In the surgical arena, One of the goals of reconstructive surgery is to be able to replace damaged tissue with new tissue, perhaps grown from a patient's own cells. For example, researchers have endeavored to develop cartilage regeneration systems in which isolated chondrocytes are injected into a damaged area in the context of a polymer scaffold (see, for example, Atala et al., *J. Urol.* 150:747, 1993; Freed et al., *J. Cell. Biochem.* 51:257, 1993 and references cited therein). Similar seeded scaffold systems have been studied in the context of bone repair, where osteoblast cells are utilized in conjunction with polymeric or ceramic supports (see, for example, Elgendy et al., *Biomater,* 14:263, 1993; Ishaug et al., *J. Biomed. Mater. Res.* 28:1445, 1994). Seeded compositions have also been studied for their utility in bladder control and vesicoureteral applications (see, for example, Griffith-Cima et al., published PCT application no. WO 94/25080.

Researchers in the field have identified several characteristics that are desirable for scaffold materials to be used in such seeded compositions. For example, Freed et al. (*Bio/Technology* 12:689, 1994) list in the following six factors as desirable features:

(1) the scaffold surface should permit cell adhesion and growth;

(2) neither the scaffold material nor its degradation products should provoke inflammation or toxicity when implanted in vivo;

(3) the scaffold material should be reproducibly processable into three dimensional structures;

(4) the scaffold material should have a porosity of at least 90% so that it provides high surface area for cell-scaffold interactions, sufficient space for extracellular matrix regeneration, and minimal diffusion constraints during in vitro culture;

(5) the scaffold material should resorb once it has served its purpose of providing a template for the regenerating tissue; and (6) the scaffold degradation rate should be adjustable to match the rate of tissue regeneration by the cell type of interest.

There remains a need for the development of a drug delivery vehicle that is biocompatible, fully resorbable, and not detrimental to drug activity. There is also a need to develop suitable materials for use as scaffolds in tissue repair. The present invention solves these needs, providing materials and compositions useful in drug delivery and in tissue repair.

DEFINITIONS

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in the material. However, for the amorphous precursor materials of the present invention, it is preferable that the degree of crystallinity be less than that desired in the product material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, IJntema et al., *Int. J. Pharm.* 112:215 (1994)).

"Bioresorbable"—"Bioresorbable" refers to the ability of a material to be resorbed in vivo. "Full" means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted, "Strongly bioresorbable", as that term is used herein, means that at least 80%, preferably 95–99%, and most preferably >99% of the total mass of material implanted intramuscularly or subcutaneously is resorbed within one year. In preferred embodiments of the invention, the strongly resorbing poorly crystalline apatitic (PCA) calcium phosphate is characterized in that, when at least 1 g (preferably 1–5 g) of PCA material is implanted at a subcutaneous or intramuscular site, at least 80% of the material is resorbed within one year. In more preferred embodiments, the material will be resorbed within nine months, six months, three months, and ideally one month. Furthermore, particularly preferred materials are characterized in that they can be fully resorbed in the stated time periods. For the purpose of this disclosure, "weakly" resorbable means that less than 80% of the starting material is resorbed after one year.

"Effective Amount"—An effective amount of a biologically active agent is an amount sufficient to elicit a desired biological response.

"Hardening"—"Hardening" refers to the process by which the hydrated precursor is transformed into a hardened PCA material. The PCA material is considered to be "hardened" when it is a substantially non-formable solid. Such a hardened PCA material has minimal compressibility and tends to undergo plastic as opposed to elastic deformation.

"Hydrated precursor"—The term "hydrated precursor", as used herein, refers to the paste or putty formed by hydration of the dry PCA precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" PCA precursor pastes described herein are hydrated precursors. Preferred "injectable" hydrated precursors have a consistency appropriate for delivery through an 18 gauge needle.

"Poorly-crystalline apatitic calcium phosphate", "PCA calcium phosphate" and "PCA material", as those terms are used herein, describe a synthetic poorly crystalline apatitic calcium phosphate. The PCA material is not necessarily restricted to a single calcium phosphate phase provided it has the characteristic XRD and FTIR pattern. A PCA calcium phosphate has substantially the same X-ray diffraction spectrum as bone. The spectrum is generally characterized by only two broad peaks in the region of 20–35° with one centered at 26° and the other centered at 32°. It is further characterized by FTIR peaks at 563 $cm^{-1}$, 1034 $cm^{-1}$, 1638 $cm^{-1}$ and 3432 $cm^{-1}$ (±2 $cm^{-1}$). Sharp shoulders are observed at 603 $cm^{-1}$ and 875 $cm^{-1}$, with a doublet having maxima at 1422 $cm^{-1}$ and 1457 $cm^{-1}$.

"Promoter"—The term "promoter", as used herein, describes a material or treatment that promotes hardening of a hydrated precursor and may enhances the ACP to PCA calcium phosphate conversion. Some promoters participate in the conversion and are incorporated into the product PCA material; others, known as "passive" promoters, do not participate.

"Reactive"—"Reactive" is used herein to refer to the ability of an amorphous calcium phosphate when mixed with liquid to form a hydrated precursor to undergo conversion to the PCA material of the present invention in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion" can encompass conversion of both the ACP and the second calcium phosphate. The degree of hardening and the kinetics of the hardening process are also important elements of reactivity. Some ACPs are more reactive than others. An ACP is considered "highly reactive" if it undergoes conversion and hardening to a PCA material in the presence of a weak promoter, such as dicalcium phosphate dihydrate ("DCPD") with a grain distribution containing a significant fraction of grain sizes greater than 100 μm. Preferred highly reactive ACPs produce a hardened PCA material in the presence of weakly promoting DCPD and water at 37° C. in less than twelve hours, with hardening being substantially complete in about one to five hours, and ideally 10–30 minutes.

SUMMARY OF THE INVENTION

The present invention provides a synthetic, poorly crystalline apatitic calcium phosphate material that has excellent biocompatibility, resorbability, and processability characteristics and is useful in drug delivery and cell seeding (in vivo and in vitro) applications.

The synthetic PCA material utilized in the present invention is compatible with cells and with a wide array of biologically active agents. The material can be employed to deliver agents or cells to any of a variety of sites in the body, or can be used in vitro. The material is characterized by a distinctive X-ray diffraction pattern that reveals its poor crystallinity. Preferable, the material has a calcium to phosphate ratio in the range of about 1.1 to 1.9. More preferably, this ratio is in the range of about 1.3 to 1.5.

The PCA material utilized in the present invention is strongly bioresorbable. That is, when an implant comprising at least 1 g of material is implanted in pellet form in an intramuscular or subcutaneous site, at least approximately 80%, preferably 90–95%, and most preferably >95%, of the material is resorbed within one year, preferably within 9 months, 6 months, 3 months, and, ideally 1 month. More preferably, at least 80%, preferably 90–95%, and most preferably 22 95%, of a 5 g implant is resorbed within these time frames. It will be appreciated that the conformation of the material (e.g., in a sphere is compared with a rod or other shape) may affect is resorption rate. Furthermore, the resorption rate of the delivery vehicle can be varied through its manner of preparation.

In preferred embodiments of the present invention, the synthetic PCA material is formed in a reaction in which at least one amorphous calcium phosphate (ACP) precursor is exposed to a promoter. In particularly preferred embodiments, the promoter comprises a second calcium phosphate material. The reaction conditions employed to produce the PCA material utilized in the present invention are mild, so that biological agents or cells can be incorporated into the material during the formation reaction, if desired. Alternatively, the agents may be incorporated after the delivery vehicle is made. The delivery vehicle material may be formed into any of a variety of useful delivery shapes, either before or after the introduction of biologically active agent or cell, and may be delivered to the site by, for example, injection or surgical implantation. The material may be introduced into a site in a wet, non-hardened state (i.e., as a hydrated precursor) and allowed to harden in situ. The vehicle may alternately be hardened in vitro at an elevated temperature, generally at or above 37° C., and thereafter surgically implanted into a subject (animal or human).

The PCA material of the present invention may be fabricated in vitro either in the presence or absence of the biologically active agent or cell. Alternatively the biologically active agent or cell may be added post-hardening by exposing the pre-formed vehicle to the agent.

The present invention therefore provides vehicles for delivering biologically active agents, which vehicles comprise to PCA calcium phosphate and a biologically active agent. The inventive vehicles optionally comprise, for example, other bioresorbable materials, erosion rate modifiers, cells, or other factors that modify one or more characteristics of the vehicle (such as its strength, adherence, injectability, frictional characteristics, etc.). One advantage of the delivery system of the present invention is that it allows a high local concentration of drug to be achieved, which is particularly useful with drugs that have toxic side effects and also with labile drugs.

The invention also provides methods of preparing delivery vehicles, of altering delivery vehicle characteristics, and of delivering biologically active agents to a site. Preferred delivery sites include both in vitro and in vivo sites. The delivery vehicles of the invention are suitable for delivery into human or animal sites. Preferred in vivo sites include bony sites, intramuscular sites, interperitoneal sites, subcutaneous sites, central nervours system sites, and occular sites.

The present invention additionally provides therapeutic, structural, or cosmetic implants comprising the inventive PCA material and at least one cell. Preferably, the at least one cell is a bone-forming or bone-degrading cell. Particularly useful cells types include chondrocytes, osteocytes, osteoblasts, osteoclasts, mesenchymal stem cells, fibroblasts, muscle cells, hepatocytes, parenchymal cells, cells of intestinal origin, nerve cells, and skin cells, and may be provided as primary tissue explants, preparations of primary tissue explants, isolated cells, cell lines, transformed cell lines, and host cells. The implants may also comprise additional components such as biologically active agents or factors that alter the characteristics (such as resorbability, strength, adherence, injectability, frictional characteristics, etc.).

The invention also provides methods of preparing such implants; methods of growing bone or cartilage in vivo or in vitro, a natural sites or ectopic sites; methods of osseous augmentation; and methods of diagnosing disease states by assaying tissue-forming potential of cells isolated from a host. The invention also provides in vitro cell culture systems and cell encapsulation matrices.

DESCRIPTION OF THE DRAWINGS

FIG. 4 and X-ray diffraction patterns of (a) reactive amorphous calcium phosphate; and (b) dicalcium diphosphate used in a reaction to form a bone substitute material of the invention;

FIG. 6 is infrared spectra of (a) dicalcium phosphate dihydrate, (b) the activated ACP of the invention and (c) the PCA material of the present invention;

FIG. 10 presents photomicrographs of tibial defects either untreated (10a) or treated (10b) with the PCA material of the present invention. In FIG. 10b, large arrowheads denote one edge of the defect. In both Figures, magnification is 4×, bone is decalcified, and slides are treated with hematoxylin and eosin.

FIG. 11 is a photomicrograph of canine trabecular bone grown into a defect 8 weeks after surgery treated with the drug delivery vehicle of the present invention (Magnification 10×, decalcified; hematoxylin and eosin).

FIG. 12 is a photomicrograph of a canine cortical bone defect 4 weeks after surgery that was treated with the drug delivery vehicle of the present invention. (Magnification 4×; undecalcified, Light Green Basic Fuchasin).

DESCRIPTION OF PREFERRED EMBODIMENT

The PCA Material

Figure 1:
FIG. 1 is a high-resolution transmission electron micrograph of the reactive amorphous calcium phosphate illustrating the nanometer-sized grains in clusters with relatively unclear boundaries and partially immersed in shapeless form (arrows)

The PCA material of the present invention is described in co-pending applications U.S. Ser. No. 08/650,764 and/or U.S. Ser. No. 08/446,182, each of which is incorporated herein by reference. The material is also described in a set of related applications, entitled "Delivery Vehicle"; "Conversion of Amorphous Phosphate to Form a Novel Bioceramic"; "Orthopedic and Dental Ceramic Implants"; and "Bioactive Ceramic Composites", each of which is on even date herewith and is incorporated herein by reference. In light of the bread of disclosures in each of these related applications, the details of the inventive PCA materials will not be belabored here. A summary of its characteristics will suffice.

The PCA material employed in the present invention is characterized by its biocompatibility, its biological resorbability and its minimal crystallinity. The material may be highly porous and rapidly resorbable or of decreased porosity and slowly resorbable. Its crystalline character is substantially the same as natural bone, and lacks the higher degree of crystallinity seen in the bone substitute known to the art. The inventive PCA material also is biocompatible and not detrimental to the host.

The PCA material of the present invention may be implanted in a patient in a paste or putty form (i.e., as a hydrated precursor). Since the inventive reaction that produces the hardened PCA material can be initiated outside the body, and proceeds slowly at room temperature, the possibility that the material will "set up" prior to application to the surgical site and become unusable is minimized. The reaction accelerates significantly at body temperature and the material hardens in place. This feature is particularly useful in the surgical setting, where custom fitting of the device to the implant location is typically required. For example, in some preferred embodiments of the invention, an antibiotic and/or regenerative factor is delivered to a fracture site. In such embodiments, the inventive paste containing the therapeutic agent will be applied to and used to fill a fracture site, as well as to deliver the desired agent.

Alternatively, the inventive PCA material may be pre-hardened outside the body, loaded with the desired biological agent or cell(s), and implanted at a later time. This approach is useful in those situations where custom shapes are not essential, and where production of large numbers of implants is desired.

Generally, the formation reaction of the present invention is completed after application to the surgical site. The material typically hardens in less than five hours, and substantially hardens in about one to five hours, under physiological conditions. Preferably, the material is substantially hardened within about 10–30 minutes. The consistency and formability of the PCA material, as well as the speed of the formation reaction, may be varied according to the therapeutic need by modifying a few simple parameters.

The resorbability of the PCA material employed in the instant invention is attributable to the combination of its porosity, its chemical composition, and its crystallinity. A patites have reduced crystalline characters and display somewhat increased solubility in aqueous solution systems when compared with more crystalline species. The low crystallinity of the inventive PCA material, and/or the presence of stable amorphous domains within it, is believed to promote its resorbability in biological systems.

The resorbability of the PCA material of the present invention can be modified by altering its density and/or porosity. Porosity facilitates both the diffusion of substances to and from the interior of the material and, in certain applications, the penetration of cells and cell processes into the material matrix. Drug delivery materials of lower porosity tend to resorb more slowly in vivo than do those of higher porosity. In one embodiment of the invention, porosity is increased through the use of a dry mixture of controlled particle size reactants; in other embodiments, chemical or physical etching and leaching techniques are employed.

Thus, different embodiments of the present invention provide PCA materials with different resorption rates. Selection of reactants, porosity, final crystallinity, and amounts and types of crystallization inhibitors employed yields difficulty embodiments of the PCA material of the present invention, so that, in different embodiments, 1 g of material is resorbed (i.e., at least 80%, preferably 90–95%, and most preferably >95%, resorbed) within any desired time period from 2 weeks to 1, 3, 6, and 9 months, to 1 year.

In a preferred embodiment of the present invention, the reaction that produces the PCA material is initiated by adding physiological saline to a mixture of two dry components so that a thick paste forms that hardens in about a half an hour. Other aqueous agents, such as serum, tissue culture medium, or another buffered solution or distilled water, may be used in place of saline. Most often, the resulting resorbable PCA material will be "calcium deficient", with a calcium to phosphate ratio of less than 1.5 as compared to the ideal stoichiometric value of approximately 1.67 for hydroxyapatite.

The invention provides a test for identifying suitable PCA materials and reactive precursors. Specifically, precursors are combined, are hydrated with a limited amount of water (so that a paste or putty is formed), and are allowed to harden into a PCA material. Desirable precursors are capable of hardening in a moist environment, at or around body temperature. The hardened product is then placed intramuscularly or subcutaneously in a test animal. Desirable materials are those that, when implanted as an at least 1 g pellet are at least 80%, preferably 90–95%, and most preferably >95%, resorbed within 1 year (or less). Preferably, the material can be fully resorbed. Generally, it is easier to test resorption of gram quantities of material in subcutaneous sites.

The PCA material of the present invention is formed in a reaction that employs at least one amorphous calcium phosphate (ACP) precursor, preferably an activated ACP (see, for example, Examples 1–4). In some instances, the reaction may employ only one precursor ACP, which is converted in a controlled fashion in part or whole to the PCA material of the invention. Alternatively, the reaction may employ a promoter that comprises one or more additional precursors (preferably one or more calcium and/or a phosphate sources), that combine with the ACP to yield the PCA material of the invention. Also, a non-participating promoter may be employed to facilitate conversion of the activated ACP to the inventive PCA material. In any event, reaction that can be initiated outside the body, that can be carried on in a paste-like configuration, and that significantly accelerate at 37° c. leading to a hardened calcium phosphate product are greatly preferred.

The conversion of ACP to a PCA material is promoted in the presence of water. Generally, the ACP is provided as a powder is combined with any other reactants (e.g. a second calcium phosphate), and is exposed to a limited amount of water, so that a paste or putty is formed. The hydrated precursor then hardens, and the hardening is associated with formation of the PCA material. It is an aim of this invention to provide methods which promote the conversion of ACP to a PCA material in a controlled fashion, producing a hydrated precursor paste or putty that hardens predictably and has utility in dental, orthopedic, drug delivery, cell therapy, and/or other applications. The promoters used to accomplish this conversion may themselves be converted to PCA material, or may participate in other chemical or physical reactions. Some preferred promoters may also remain unchanged during the conversion, providing a catalytic or nucleator function. Particularly suitable in this regard are substances that provide reactive surfaces that weakly promote crystallization to produce PCA calcium phosphate.

ACP precursors only: When amorphous calcium phosphate is used as the sole precursor to produce a reasonable PCA material, it is important to control the neutral tendency of the ACP to convert to highly crystalline hydroxyapatite, On the other hand, the time course of conversion should be fast enough to have surgical utility. One approach is to combine a precursor ACP containing an inhibitor of crystal formation (e.g., the ACP of Example 1) with an ACP that does not contain an inhibitor of crystal formation (e.g., a promoter). The reactants may be mixed in a dry state, with the appropriate particulate size and an excess of the inhibitor-containing ACP. The reactants can then be exposed to crystal-forming conditions such as the addition of water, followed by an elevation in temperature (e.g., as occurs following introduction into the body), to convert the reactants to the PCA material of the invention. Other methods of controlled conversion involve the use of catalysts.

ACP precursor plus additional calcium phosphate sources: ACP may be reacted with a second calcium source (including a second ACP) using any reaction-promoting technique. In preferred embodiments; the second calcium source is itself a promoter. The reaction being promoted is the conversion of an amorphous calcium phosphate into a hardened nanocrystalline or poorly crystalline apatitic calcium phosphate. Such reactions include acid/base, displacement, substitution, and hydrolysis reactions as well as purely physical and mechanical reactions (e.g., grinding, mixing). Catalytic conversion, such as surface-catalyzed conversion of ACP to a PCA material, may also be employed. Under any reaction scheme, it is important that the ACP retains significant amorphous character throughout the reaction. Specifically, the overall crystallinity within the starting ACP should not exceed that desired in the end product. Thus, certain reaction schemes may require stabilization of the amorphous nature of the ACP throughout the reaction period. Examples of inhibitors of crystal formation that are known to the art and are useful for such stabilization include carbonate, pyrophosphate and magnesium.

In some preferred embodiments, the ACP component is activated under heat in order to facilitate the conversion being promoted by the second calcium containing reactant or other promoter. Examples of suitable such second reactant promoters include DCPD, other crystalline or poorly crystalline calcium phosphates, calcium sources, phosphate sources, or a second ACP. Other methods of promoting conversion, such as catalysis of the use of ionic solvents or promoters of nucleation, may also be employed to promote reaction between substituents. The second calcium phosphate reactant may be of any crystalline structure and should be chosen so as to be reactive with the first ACP either directly or through the use of reaction enhancing vehicles such as ionic solvents or catalysts. Appropriate reaction conditions will be determined by demonstration of rapid hardening at 37° C. after the reactants are mixed and water is added.

The delivery vehicle formation reaction may also be designed to produce an end product that is porous. In one embodiment, the use of a dry mixture of controlled particle size reactants leads to a porous material. Other methods of promoting porosity, such as chemical or physical etching and leaching, may be employed.

The present invention provides a novel process for activating a standard amorphous calcium phosphate precipitate into highly reactive amorphous solids. The amorphous solids can be used in the reaction described above to form a poorly- or nanocrystalline synthetic apatitic calcium phosphate that provides bioactivity, bioresorbabiity and structural integrity. The novel amorphous material can be reacted with other calcium phosphates at or below 37° C. to form a bone-like material consisting of poorly crystalline apatitic calcium phosphate.

Prior art acid-base reactions of conventional crystalline calcium phosphates produce poorly reacted solids, having reaction products that are too crystalline to be sufficiently resorbable in living tissues. The reactions from the prior art generally incomplete and the reaction products are inhomogeneous. In constrast, the amorphous calcium phosphate of the present invention reacts quickly and completely with a wide variety of calcium phosphates and other calcium- or phosphorus-bearing materials to provide a homogeneous product.

The source of the enhanced reactivity of the ACP of the present invention is not completely understood; however, it is believed to be associated with the amorphicity (lack of crystallinity) and, in some embodiments, ion pair site vacancies in the material, as created by the process of the present invention. The vacancies may provide reactive sites for subsequent reaction. These observations will be discussed more fully, below.

The method of the present invention permits initial formation of amorphous calcium phosphate particles of less than 1000 Å, preferably 200–500 Å, and most preferably 300 Å, the further growth of which is curtailed by rapid precipitation of the product from solution. During reaction of calcium and phosphate ion sources to form an amorphous calcium phosphate, a third ion is introduced in the solution so that this third ion is incorporated in the amorphous precipitate structure instead of trivalent $PO_4^{3-}$ group(s). Because some $PO_4^{3-}$ is replaced by the third ion, the overall $PO_4^{3-}$ decreases, thus increasing the Ca/P ratio of the amorphous precipitate (as compared to standard amorphous calcium phosphate) and modifying the valence or charge sate of the calcium phosphate. The amorphous solids then may be rapidly freeze-dried to preserve the chemical and physical properties of the material. The amorphous solids then may be treated under specific conditions selected to promote removal of at least some of the third ion. Where the third ion is carbonate, specific temperature and pressure conditions lead to the reduction of total carbon, presumably as gaseous carbon dioxide from the amorphous solid, while maintaining the product amorphicity.

The resultant material is an amorphous solid with a higher Ca/P ratio than is typically found in amorphous calcium phosphates, where the ratio generally reported in the past is 1.50. Further, removing carbon from the material results in a vacancies in the interstitial structure within the amorphous solids, rendering it a highly reactive solid. There may be several possible vacancies sources. The material possess a porosity which promotes reactivity by various means, such as increased surface area. The material may also undergo a change in the stoichmetry balance upon removal of the third ion. This stoichiometry change may result a charge imbalance which is responsible for the increased reactivity of the amorphous calcium phosphate.

It is desirable to maintain substantial amorphous character within the material throughout the entire process. If crystallinity in its entirety (single crystalline regions), or even in local domains (microcrystalline regions), is introduced to excess during the process or in the final product, the solid has been found to be less reactive. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

The amorphous state of the amorphous calcium phosphate is induced by controlling the rate and duration of the precipitation process. The amorphous calcium phosphate of the present invention is precipitated from solution under conditions where initial precipitation is rapid. Rapid precipitation results in the formation of many extremely small calcium phosphate nuclei. Additionally, rapid crystal or grain growth leads to the production of more defects within each grain, thereby also increasing solubility. At the extreme end of the spectrum, crystal or grain growth is so rapid and defect density is so significant that an amorphous calcium phosphate results. Amorphous calcium phosphate is gel-like and includes solid solutions with variable compositions. These gels have no long range structure, but are homogeneous when measured on an Angstrom scale. Under physiological conditions, these amorphous compounds have high solubilities, high formation rates and high rates of conversion to poorly crystalline apatitic calcium phosphate.

The amorphous calcium phosphate solids acquired by this method retain their amorphous nature sufficiently long enough to be introduced into the final reaction as substantially amorphous solids. They can also be mixed and reacted with other solids or solutions containing phosphates, to obtain solids containing a homogeneous distribution of nanometer-sized crystals. Further, in preferred embodiments, because the amorphous calcium phosphate reacts completely with the other solids, the Ca/P of the resultant solid will constitute the total calcium and phosphorous from such reaction, i.e., there will be an essentially complete reaction. When a proper molar concentration of phosphate from the solution or solids is reacted with the novel amorphous calcium phosphate material, a poorly crystalline apatitic calcium phosphate material (Ca/P 1.1–1.9) is obtained. Thus, the present invention permits one to design and modify the chemical composition of the resultant product, thereby providing a further mode of controlling bioactivity of the final product used as a delivery vehicle or cell scaffold.

In one embodiment of the present invention, a solution is prepared that contains calcium and phosphate ions and a third ion in a concentration, at a pH, and at a temperature that will promote the rapid nucleation and precipitation of calcium phosphate. When precipitation is sufficiently rapid, an amorphous gel-like calcium phosphate is formed. Because the thermodynamically favored crystalline form of hydroxyapatite is enhanced by reducing the rate of reaction, certain processing steps of increasing the rate of reaction may be taken to ensure than an amorphous compound is obtained. The following factors, among others, are to be considered when designing a solution for the rapid precipitation of the amorphous calcium phosphate of the present invention.

Preferred conditions: Rapid mixture of calcium and phosphate sources to increase the rate of reaction. The rate of reaction is increased to favor non-stable phases as a product. Allowing more reaction time for each of the ions to juxtapose correctly to form a solid will result in a more thermodynamically favorable crystalline and stable structure.

Preferred calcium and phosphate sources: The use of highly concentrated or near supersaturation solutions ensures that a more rapid reaction will occur.

Preferred temperature: Although the reaction can be carried out at room temperature, temperatures of near boiling point to increase the concentration of one reactant is a possible means of increasing the rate of reaction.

In one embodiment calcium ions, phosphate ions and carbonate ions are mixed together rapidly in an aqueous solution to obtain a carbonate containing amorphous calcium phosphate solid. The relative concentrations of the ions are selected to give a precipitate having the desired Ca/P ratio. The carbonate ion substitutes for a phosphate ion in the amorphous calcium phosphate. The carbonated amorphous calcium phosphate may be obtained by precipitation from an aqueous carbonate solution. Suitable aqueous carbonate solutions include, by way of example only, bicarbonate solution, sodium carbonate solution, potassium carbonate solution. It is further contemplated as within the scope of the invention to use non-aqueous solutions.

Use of a carbonated material is desirable because it permits manipulations of the Ca/P ratio by substitution of $PO_4^{3-}$ by $CO_3^{2-}$. Additionally, the presence of $CO_3^{2-}$ is known to retard the development of crystallinity in amorphous calcium phosphate. Is recognized, however, that other ions or a mixture of ions may be suitable in place of or in addition to carbonate ion in modifying the Ca/P ratio and in introduction of reactive site vacancies into the amorphous calcium phosphate, such as by way of example only, nitrate, nitrite, acetate, $Mg^{+2}$ and $P_2O_7^{4-}$ ions.

The amorphous calcium phosphate precipitate may be collected and filtered prior to activation. It is preferred to perform this step in a cold room or at sub-ambient temperatures so as to preserve the amorphous state of the precipitate collected. Collection may typically be carried out by any conventional means, including, but in no way limited to, gravity filtration, vacuum filtration or centrifugation. The collected precipitate is gelatinous and is washed more than once with distilled water.

The washed precipitate is then dried under any condition that maintain the amorphous character of the material. Lyophilization is a suitable, but not exclusive, technique. The precipitate is frozen and, while being kept frozen, is dried to remove the bulk of the entrained liquid. This procedure may be accomplished by placing the frozen precipitate into a vacuum chamber for a given period of time. Freeze-drying typically occurs at liquid nitrogen temperatures for a time in the range of 12–78 hrs, preferably about 24 hours, and under a vacuum in the range of $10^-$–$10^{-4}$, preferably $10^{-4}$, torr. A preferred method includes lyophilizations because the cryogenic temperatures typically used in lyophilization inhibit further crystallization of the material. As a result, the amorphous calcium phosphate obtained thereby is an extremely fine free flowing powder.

The dried ACP may then be activated. In a preferred embodiment, where carbonate is present in the ACP, the ACP powder is heated to drive off remaining free water and water of hydration and to remove carbon, presumably through the decomposition of $CO_3^{2-}$ into $CO_2$ and oxygen. The heating step is carried out at a temperature of less than 500–600° C. but more than 425° C., so as to prevent conversion of the amorphous calcium phosphate into crystalline hydroxypatite. Heating is preferably carried out at a temperature in the range of 450–460° C., preferably for ½ hour to 6 hours.

Low crystallinity and site vacancies (porosity and/or stoichiometric changes) may account for the observed higher reactivity of the activated amorphous calcium phosphate of the present invention. This is exemplified by the following observations. A carbonate-containing amorphous calcium phosphate which has been heated to 525° C. is observed to have an increase in formation of crystalline hydroxyapatite and to have a corresponding decrease in reactivity. Amorphous calcium phosphate that is heated to only 400° C. retains its amorphous characteristic, but exhibits a decreased reactivity. Presumably this decrease in reactivity is related to the higher carbonate levels (and fewer site vacancies) observed by IR in samples treated at this lower temperature. These findings suggest that both amorphicity and decreased carbon content (vacant reactive sites) are a factor in reactivity. This is not limited to be in any way an exclusive basis for reactivity. Other bases for the observed reactivity are considered to be within the scope of the invention. The resulting amorphous calcium phosphate powder is a highly reactive amorphous calcium phosphate material with a Ca/P ratio of between 1.1–1.9, preferably about 1.55 to 1.65, and most preferably about 1.58. The powder has been characterized by a variety of analytical techniques.

In FIG. 1, a high-resolution transmission electron micrograph is shown to illustrate the morphological characteristics and the angstrom-sized nature of the preferred reactive amorphous calcium phosphate of the present invention. Preferred particle sizes are less than 1,000 Å. Note the unclear boundaries separating the globule-like clusters, lacking clear edges and surfaces, in contrast to crystalline materials.

Figure 2:
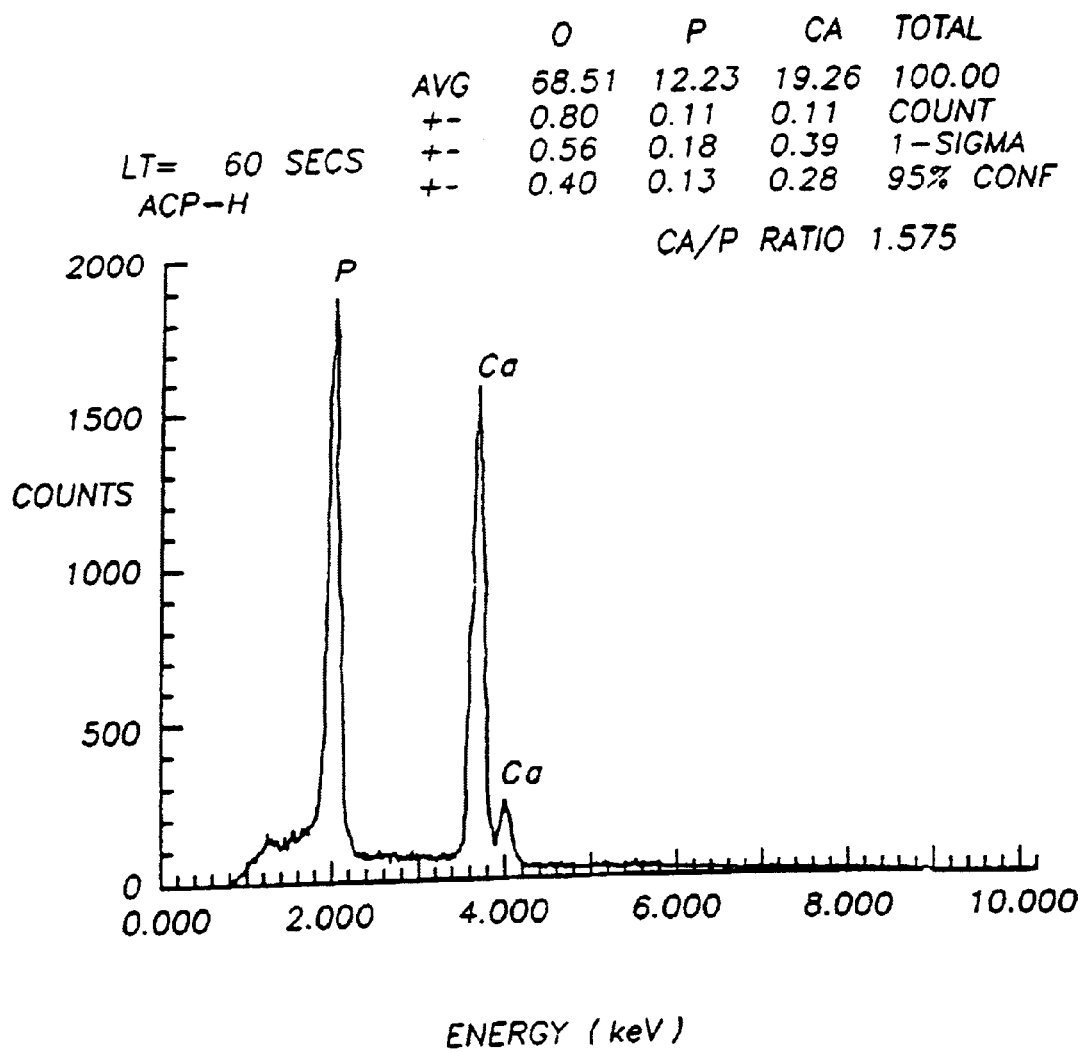
FIG. 2 is an energy-dispersive electron microprobe spectrum of the reactive amorphous calcium phosphate of the present invention after the vacuum heating procedure which yielded Ca/P to be 1.58.

The amorphous nature of the reactive ACP of the invention is characterized by an X-ray pattern that is devoid of sharp peaks at any position of the diffracting angles that correspond to known crystalline calcium phosphates (FIG. 4a). The Ca/P measurement performed using wave length-dispersive X-ray analysis on an electron micro-probe of the same material after heat treatment yields Ca/P to be 1.58 (FIG. 2).

These characterizations demonstrate that although there is a change in the local moiety of certain groups in the amorphous calcium phosphate solids, the overall amorphicity is maintained throughout the process.

In another preferred embodiment, the highly reactive amorphous calcium phosphate is reacted with a second calcium phosphate to obtain a PCA material. As discussed above, crystalline hydroxyapatite is the thermodynamically preferred reaction product, and is usually described as not resorbable under physiological conditions. The use of an amorphous calcium phosphate, which can convert quickly and completely to produce an apatitic compound without significant crystallization, provides a novel route to a poorly-crystalline apatitic calcium phosphate that is resorbable under physiological conditions.

The amorphous calcium phosphate powder of the present invention may be mixed with a promoter and thereby convert to form a PCA material. This reaction may occur at room temperature upon mixing of the powder with any of a variety of both acidic and basic calcium phosphates in the presence of a limited amount of a fluid such as, but not limited to, water, saline, buffer solution, serum or tissue culture medium. Depending upon the amount of fluid added, the mixture of amorphous calcium phosphate of the present invention and a second calcium phosphate results in a highly formable and/or highly injectable paste with varying degrees of paste consistency.

The method of preparation of the promoter and/or the ACP will affect the ease by which the hydrated precursor is converted into the PCA material. As noted above, the method of mixing the powdered reactants prior to addition of liquid affects the reactivity of the system. Thus, hand mixing using a mortar and pestle does not result in as reactive a system as a prolonged machine grinding of the reactant powders. Therefore when comparing promoters, it is important to use standardized preparation conditions.

It is hypothesized that the conversion of ACP to the reactive PCA calcium phosphate is a surface catalyzed phenomenon. If so, it may be desirable to produce a particular promoter with a reproducible surface area. Specific surface area of the ACP and promoter powders can be controlled to control the reaction conditions and final PCA material properties. Thus, to control reaction reproducibility it is advantageous to provide a promoter with a known grain size distribution. Standard sieving techniques are suitable for selection of specific grain sizes. Surface area has been shown to be correlated to the compressive strength, and possibly the porosity and resorbability, of the PCA material.

Man calcium- or phosphate-containing compounds may be used as participating promoters in the hardening reaction. A calcium phosphate promoter, may be of any crystalline structure and should be chosen so as to be reactive with ACP either directly or through the use of enhancing promoters. Preferred participating promoters are those which tend themselves to undergo conversion to hydroxyapatite through an intermediate PCA calcium phosphate phase.

Appropriate calcium phosphates for use as promoters with the ACP described herein include neutral, basic, and acidic calcium phosphates, preferably apatitic phosphates, that provide the appropriate stoichiometry for reaction to obtain a apatitic calcium phosphate. In a preferred embodiment, an acidic (pH 5–7) calcium phosphate is used. Suitable calcium phosphates include, but are in no way limited to, calcium metaphosphate, dicalcium phosphate dihydrate, heptacalcium decaphosphate, tricalcium phosphates, calcium pyrophosphate dihydrate, the poorly crystalline apatitic material of the invention, calcium pyrophosphate, octacalcium phosphate, tetracalcium phosphate and additional ACPs. Other solids that would provide a source of phosphate or calcium, such as, by way of example only, CaO, $CaCO_3$, calcium acetate, and $H_3PO_4$, may be mixed to form a final product to yield a desired Ca/P ratio close to about 1.1–1.9, preferably about 1.3 to 1.5. It may be desirable to provide the second component in the amorphous or poorly crystalline state, as well.

Some calcium phosphate promoters may be prepared as either weak promoters or strong promoters. For instance, a DCPD sample with a grain size in the range of 100–125 µm (or distribution B3 in Example 5) reacts only marginally with the highly reactive ACP of the invention under certain conditions (see Example 5). DCPD of this grain size may be considered "weakly promoting". Thus, DCPD may be used in this format to screen for highly reactive ACPs.

In some embodiments of the invention, it is not required that the reaction employ a participating second calcium phosphate to produce a PCA material. Rather, it is within the scope of the invention to merely promote hardening and the conversion of the reactive ACP into a PCA material by addition of one or more "passive" promoters (also termed "non-reactive" or "non-participatory" promoters) that do not participate in the reaction. Suitable passive promoters include, but are not limited to, materials or treatments that have previously been described as promoting conversion of calcium phosphate materials into hydroxyapatite. For example, water, heat, nucleators and catalysts can be used as passive promoters. In some embodiments, the catalysts provide surface area, the presence of which promoters the hardening and conversion of ACP to poorly crystalline apatitic calcium phosphate. For example, $Al_2O_3$, mica, glass and sand, among other things, are useful passive promoters. In preferred embodiments, material promoters are employed that are insoluble or of low solubility in water, may be prepared in granular form in the range of 1–200 μm in diameter and are resorbable in vivo. Thus, polymers such as poly L-lactic acid (PLLA) and polyglycolic acid (PGA) are particularly desirable promoters.

Where a second calcium phosphate is employed as a promoter, it is often crystalline, as is evidenced by the presence of sharp diffraction peaks typical to the calcium phosphate of interest in the X-ray diffraction pattern (FIG. 4b). In contrast, the reactive ACP is amorphous and shows no identifiable peaks by X-ray diffraction (FIG. 4a). Despite its higher crystallinity, however, X-ray diffraction suggests that dicalcium diphosphate is consumed in the reaction with reactive ACP and the product PCA material is of much reduced crystallinity. Similarly, when stoichiometric HA is employed as a second calcium phosphate source, it is also consumed in the reaction and a PCA material of reduced crystallinity is produced.

Because at least one of the reactants is amorphous and highly reactive, the formation reaction of the present invention proceeds at or above room temperature to provide a hardened apatitic material having a poorly-crystalline or microcrystalline microstructure. In preferred embodiments, the conversion reaction also is substantially complete, thereby insuring that all calcium and phosphate of the mixture are consumed by the resultant PCA product. This result permits reliable manufacture of apatitic products simply by selection of the relative proportions of the starting amorphous and secondary calcium phosphates. It is desirable to maintain a calcium to phosphate ratio of about 1.2–1.68, preferably less than 1.5, and most preferably about 1.38.

The product apatitic material contains labile environments characteristic of naturally-occurring bone. In naturally occurring bone, minerals are characterized by nanometer-sized structure, providing high surface areas to interact with the surrounding tissue environment, resulting in resorption and remodelling of tissues. The present invention, with its nanometer-sized crystals as the product, closely mimics the naturally occurring bone materials. Further, properties such as crystallinity and Ca/P ratios are closely designed in the present invention to simulate the mineral properties found in living tissues of bone.

The PCA produced during the inventive reaction is associated with hardening of the hydrated precursor material. It should be noted, however, that while complete conversion of the ACP precursor is a preferred embodiment, hardening of the hydrated precursors may occur prior to complete conversion or even in the absence of complete conversion. Such partially converting, but nonetheless hardening, reactions are considered to be within the scope of the invention.

As mentioned above, combination of dry ACP with any other reactants and a limited amount of aqueous solution produces a hydrated precursor. By selecting the appropriate amount of liquid to be added to the reactants, the viscosity of the may be adjusted according to need. The hydrated precursor may be prepared either with an injectable or a formable consistency. Injectable consistency means as thick as possible while still capable of passing through a 16 to 18 gauge needle. Most often, this will be a "toothpaste"-like consistency. Formable refers to consistency that allows the material to retain its shape. In the extreme case of a formable consistency, the hydrated precursor will have the consistency of glazing putty or caulking compounds. The hydrated precursor also may be prepared with just enough liquid to be both injectable and formable. In the past form, the material has markedly improved flow characteristics over prior art compositions. Flow characteristics are toothpaste-like while prior art materials generally exhibit a granular or oatmeal-like consistency. The hydrated precursor may be prepared before use, up to a period of several hours if held at room temperature and if evaporation is minimized. The storage time may be extended by maintaining the paste at reduced temperatures in the range of 1–10° C. in the refrigerator provided steps are taken to minimize evaporative loss.

In some preferred embodiments (e.g., Examples 9–14, below), the reaction is endothermic and occurs slowly at room temperature, but is accelerated significantly at body temperature. This is particularly useful in a surgical situation, since the paste formed by mixing reactants with water remains injectable for a considerable period of time (up to several hours) while held at or below room temperature. Thus, at room temperature (ca. 22° C.) the paste hardens after a timer greater than one hour and remains formable and/or injectable for longer than 10 minutes, preferably longer than one hour, and most preferably longer than three hours. Following injection at the implant site (ca. 37° C.), the past hardens in less than about an hour, preferably in about 10–30 minutes.

Composites and Additives

The PCA material of the instant invention may be formed as a composite with other substances. Composites may be desirable to change any number of physical parameters of the vehicle including but not limited to strength, resorption time, adherence, injectability, frictional characteristics, or therapeutic agent carrying capacity or release kinetics. In general, those practiced in the art of composite fabrication will understand the methods and concepts important in composite fabrication. Additional guidance for the preparation of PCA material composites may be obtained in co-pending United States patent application entitled "Bioresorbable Ceramic Composites", filed on even date herewith and incorporated herein by reference.

In vitro Implant Formation

In addition to surgical application in paste form, the inventive implants may be pre-formed outside the body, hardened, and implanted in the solid form. Pre-formed devices may be hand shaped, molded or machined. Loading of the therapeutic agent may be accomplished by addition of the agent directly to the buffer or vehicle used to prepare the hydrated precursor. Alternatively, after hardening, the vehicle may be exposed to the therapeutic agent using dipping, rolling or spray coat methods.

Biologically Active Agents

Any biologically useful agent may be delivered from the inventive PCA material implant. In general, the only requirement is that the substance remain active in the presence of the material during fabrication or be capable of being subsequently activated or re-activated. Since the inventive paste can be prepared with a large number of aqueous vehicles and substituents, those in the art will be familiar with which specific additives can be included in order to improve stability of the agent. The stability and/or compatibility of a particular agent with the inventive material, as well as fabrication strategies, may be tested empirically in vitro. Specifically, the agent may be incorporated into the inventive material by one or more of the of the methods described herein. Following hardening of the vehicle at 37° C., the substance may be leached from the material into an analysis medium such as water or an appropriate buffer and the compound collected from the Material by diffusion into the analysis medium. The analysis medium may then be analyzed for the presence of active agent. In some instances, the material will be broken up, pulverized, or otherwise fragmented prior to contacting the analysis medium. Other methods of analysis that do not require agent diffusion, such as the growth of cells on the material or other physical, chemical, or biological assays will be known to practitioners for specific compounds.

Biologically active agents useful in the practice of the present invention include any substance having biologically activity, including organic molecules, proteins, peptides, nucleic acids, nucleoproteins, polysaccharides, glycoproteins, lipoproteins, and synthetic and biologically engineered analogs thereof. Also included are chemical agents that have biological effects (e.g., antibiotics, dyes, etc.). Proteins can be prepared by synthetic, biochemical, or recombinant techniques. Preferably, though not necessarily, the biologically active agent is one that has been deemed safe and effective for use by an appropriate governmental agency or body. For example, drugs approved for human use in the United States are listed by the Food and Drug Administration (FDA) under 21 C.F.R. §§330.5, 331–361, and 440–460; drugs approved for veterinary use in the United States are listed by the FDA under 21 C.F.R. 517 §500–582.

The term "biologically active agent" includes pharmacologically active substances that produce a local or systemic effect in animals, plants, or viruses. The term thus means any substance intended for use in the diagnosis, cure, mitigation, treatment or prevention of disease or in the enhancement of desirable physical or mental development and conditions in an animal, plant, or virus. The term "animal" used herein is taken to mean mammals, such as primates (including humans), sheep, horses, cattle, pigs, dogs, cats, rats, and mice; birds; fish; insects; arachnids; protists (e.g. protozoa); and prokaryotic bacteria.

Classes of biologically active compounds that can be loaded into the delivery vehicle of the present invention include, but are not limited to, anti-AIDS substances, anti-cancer substances, antibiotics, ACE inhibitors, antigens, adrenegic antagonists, antacids, immunosuppressants, anti-viral substances, enzyme inhibitors, neurotoxins, opioids, hypnotics, antihistamines, lubricants, tranquilizers, anti-convulsants, muscle relaxants and anti-Parkinson substances, anti-spasmodics and muscle contractants, anti-diarrheals, anti-emetics, laxatives, diuretics, miotics and anti-chloinergics, anti-glaucoma compounds, anti-parasite and/or anti-protozoal compounds, anti-hypertensives, analgesics, anti-pyretics, anti-inflammatory agents, anti-histamines, anti-tussive agents, anti-vertigo, antinertigic and anti-motion sickness medications, local anesthetics, ophthalmics, prostaglandins, anti-depressants, anti-psychotic substances, anti-emetics, imaging agents, specific targeting agents, trophic factors, growth factors, immunosuppressants, immunoactivators, anti-mitotics neurotransmitters, proteins, cell response modifiers, vaccines, nucleic acids, genes, gene fragments, gene regulatory sequences (such as promoters, enhancers, or other regulatory sites), antisense molecules, and other bioactive moieties or components of biosynthetic pathways.

A more complete listing of classes of compounds suitable for loading into delivery vehicles according to the present invention may be found in the *Pharmazeutische Wirkstoffe* (Von Kleeman et al. (eds), Stuttgart, N.Y. 1987), or in any of a variety of available pharmacology textbooks, such as *Lippincott's Illustrated Pharmacology Reviews* (Harvey et al. (eds), J. B. Lippincott Co., Philadelphia, 1992) or *Examination & Board Review Pharmacology* (Kratzing et al., Appleton & Lange, Connecticut, 1993), each of which is incorporated herein by reference. Examples of particular biologically active substances are presented below:

Angiogenic factors are substances that stimulate the growth of vasculature and include compounds such as veg-f, and some growth factors and mitogens.

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir(), phosphonoformic acid, 1-adamantanamine, peptide T, and 2',3'-dideoxycytidine.

Anti-cancer substances are substances used to treat or prevent cancer. Examples of such substances include anti-metabolites (such as, for example, methotrexate, fluorouracil, 5-fluorouracil, cytarabine, mercaptopurine, 6-mercaptopurine, 6-thioguanine), antibiotics (such as, for example, daunorubicin, doxoubicin), alkylating agents (such as for example, mechlorethamine, cyclophosphamide, uracil mustard, busulfan, carmustine, lomusline), mitotic spindle poisons (such as, for example, vinblastine, vincritine), hormones (such as, for example, hydroxyprogesterone, medroxyprogesterone acetate, magistral acetate, diethylstilbestrol, testosterone propionate, fluoxymesterone), and other agents (such as, for example, vindesine, hydroxyurea, procarbazine, aminoglutethimide, melphalan, chlorambucil, acarbazine (DTIC: dimethyltriazenomidazole carboxamide), cytosine arabinoxide).

Antibiotics are art recognized and are substances which inhibit the growth of or kill microorganisms. Antibiotics can be produced synthetically or by microorganisms. Examples of antibiotics include bactericidal agents, such as aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztrenam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancmycin; and bacteriostatic agents such as chloramphenicol, clindamyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin. Antibiotics are sometimes provided in insoluble form, which can be used where delayed delivery is desired.

Anti-viral agents are substances capable of destroying or suppressing the replication of viruses. Examples of anti-viral include a-methyl-P-adamantane methylamine, 1,-D-ribofuranosyl-1,2,4-triazole-3 carboxamide, 9-[2-hydroxyethoxy]methylguanine, adamantanamine, 5-iodo-2'-deoxyuridine, trifluorothymidine, interferon, and adenine arabinoside. Particular agents useful in the treatment of herpes viruses include acyclovir, vidarabine, idoxuridine, and ganciclovir.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine,1-hydroxy maleate, iodotubercidin, p-bromotetramisole, 10-(alpha-diethylaminopropionyl)-phenothiazine hydrochloride, calmidazolium chloride, hemicholinium-3,3, 5-dinitrocatechol, diacylglycerol kinase inhibitor I, diacylglycerol kinase inhibitor II, 3-phenylproparglyamine, $N^6$-monomethyl-L-arginine acetate, carbidopa, 3-hydroxybenzylhydrazine HCl, hydralazine HCl, clorgyline HCl, deprenyl HCl,L(−)-, deprenyl HCL,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthane, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate,S(−)-, 3-iodotyrosine, alpha-methyltyrosine,L-, alpha-methyltyrosine,D L-, acetazolamide, dichlorphenamide, 6-hydroxy-2-benzothiazolesulfonamide, and allopurinol.

Neurotoxins are substances which have a toxic effect through their action on the nervous system, e.g. nerve cells. Neurotoxins include adrenergic neurotoxins, chloinergic neurotoxins, dopaminergic neurotoxins, calcium channel blockers, and other neurotoxins. Examples of adrenergic neurorotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide. Examples of calcium channel blockers include Ω-conatoxin and verapamil.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphone sulfate, noscapine, norcodeine, normophine, thebaine. Opioid antagonists include nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarmides, diethyl isovaleramide, a-bromoisovaleryl urea, urethanes and disulfanes.

Antihistamines are substances which competitively inhibit the effects of histamines. Examples include pyrilamine, chloropheniramine, tetrahydrazoline, and the like.

Lubricants are substances that increase the lubricity of the environment into which they are delivered. Examples of biologically active lubricants include water and saline.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, Chk and ethosuximide.

Anti-inflammatories are compounds that inhibit inflammation. Different types of anti-inflammatory drugs block different chemical mediators. Examples of anti-inflammatory agents include nonsteroidal anti-inflammatory drugs (NSAIDS), such as aspirin, phenylibutazone, indomethacin, sulindac, tolmetin, ibuprofen, piroxicam, fenamates, which have anti-inflammatory, analgesic, and antipyretic activities. Also included are non-narcotic analgesics such as acetaminophen and phenacetin, although the anti-inflammatory activity of these drugs is weaker. Certain slow-acting anti-inflammatories, such as gold salts, chloroquine, D-Penicillamine, and methotrexate are useful in the treatment of arthritis. Gout-specific anti-inflammatories include colchicine, allopurinol, probenecid, and sulfinpyrazone.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds include betaxalol, pilocarpine, timilol, timilol salts, and combinations of timolol, and/or its salts, with pilocarpine.

Anti-parasitic, -protozoal and -fungals include ivermectin, pyrimethamine, trisulfapyrimidine, clindamycin, amphotericin B, nystatin, flucytosine, ketoconazol, fluconazole, natamycin, miconazole, metronidazole, diloxanide furoate, paramomycine, chlorquine, emetine, dehydroemetine, sodium stibogluconate, (for leishmaniasis), melarsoprol (for trypanosomiasis), nifurtimox (for trypanosomiasis), suramin (for trypanosomiasis), pentamidone (for trypanosomiasis), and anti-malarial agents (such as, for example, primaquine, chloroquine, quinine, mefloquine, pyrimethamine, and chloroquanide).

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain and Anti-pyretics are substances capable of relieving or reducing fever. Examples of such substances include aspirin, phenybutazone, idomethacin, sulindac, tolmetic, ibuprofen, piroxicam, fenamates, acetaminophen, phenacetin, morphine sulfate, codeine sulfate, meperidine, and nalorphine.

Local anesthetics are substances which have an anesthetic effect in a localized region. Examples of such anesthetics include procaine, lidocain, tetracaine and dibucaine.

Ophthalmics include diagnostics agents such as sodium fluorescein, rose bengal, methacholine, adrenaline, cocaine, and atropine. Ophthalmic surgical additive include alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, imitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, γ-aminobutyric acid, norepinephrine, histamine, acetylcholine, and epinephrine.

Trophic factors, growth factors, and cell response modifiers are factors whose continued presence improves the viability or longevity of a cell. In some cases, they produce chemotactic effects, or have protective effects against toxins or neurotoxins, or against neurodegeneration. Suitable such factors include, but are not limited to, platelet-derived growth factor (PDGF), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, and bone growth/cartilage-inducing factor (alpha and beta), or other bone morphogenetic proteins.

Other cell response modifiers are the interluekins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins such as OP-1, BMP-2 and BMP-7.

Hormones include estrogens (such as, for example, estradiol, estrone, estriol, diethylstibestrol, quinestrol, chlorotrianisene, ethinyl estradiol, mestranol), anti-estrogens (such as, for example, clomiphene, tamoxifen), progestins (such as, for example, medroxyprogesterone, norethindrone, hydroxyprogesterone, norgestrel), anti-progestin (mifepristone), androgens (such as, for example, testosterone cypionate, fluoxymesterone, danazol, testolactone), and anti-androgens (such as, for example, cyproterone acetate, flutamide). Hormones are commonly employed for hormone replacement therapy and/or for purposes of birth control. Steroid hormones, such as prednisone, are also used as immunosuppressants and anti-inflammatories. Delivery of steroid hormones can be delayed by esterification. Thyroid hormones include triiodothyronne, thyroxine, propylthiouracil, methimazole, and iodixode. Pituitary hormones include corticotropin, sumutotropin, oxytocin, and vasopressin.

Nucleic acids are molecules, including DNA or RNA molecules, that comprise one or more nucleosides and/or nucleotides. Since calcium compounds are known to promote cell transfection and DNA uptake in some systems, it is anticipated that resorption of the present delivery device may improve transfection efficiency. Nucleic acid molecules can be delivered as vaccines or, for example, as antisense agents. Alternatively, DNA molecules can be prepared for use in gene therapy, in which molecules can correct or compensate for genetic errors in cells into which the DNA molecules are to be introduced.

Standard protocols and regimens for delivery of the above-listed agents are known in the art. Typically, these protocols are based or oral or intravenous delivery. To the extent that the present invention provides for alternate delivery modes, modification to these protocols may be appropriate.

Biologically active agents are introduced into a delivery vehicle served from PCA material of the present invention during or after its formation (see Examples 20–21). Agents may conveniently be mixed into the paste prior to setting. Alternatively, the vehicle may be shaped and hardened and then exposed to the therapeutic agent in solution. This particular approach is particularly well suited in proteins, which are known to have an affinity for apatitic materials. A buffer solution containing the biologically active agent may be employed, instead of water, as the aqueous solution in which the amorphous calcium phosphate is converted into the synthetic, poorly crystalline apatitic material of the present invention. Buffers may be used in any pH range, but most often will be used in the range of 5.0 to 8.0 in preferred embodiments the pH will be compatible with prolonged stability and efficacy of the desired therapeutic agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for it's biocompatibility with the host tissues and its compatibility with the therapeutic agent. For most applications of nucleic acids, peptides or antibiotics a simple phosphate buffered saline will suffice.

Biologically active agents are introduced into the vehicle in amounts that allow delivery of an appropriate dosage of the agent to the implant site. In most cases, dosages are determined using guidelines known to practitioners and applicable to the particular agent in question. It is generally preferred, for these agents that bind to a receptor, to achieve local levels approximately 1–2 fold higher than the dissociation constant of the receptor-agent complex. Loading levels, device size, and resorption properties can be determined empirically through the use of animal models and human efficacy studies, as is common in the pharmaceutical industry.

One of the advantages of the present delivery material, as compared with ceramic devices generally, and with calcium phosphate materials in particular, is that it can be formed under mild reaction conditions. For example, although calcium phosphate-based ceramics (e.g., hydroxyapatites) have been much studied as potential drug delivery materials because of their biocompatibility and known affinity for protein agents, such materials are typically prepared in processes that require have detrimental effects on many therapeutic agents. For example, some methods require sintering above 500° C., others require the use of acidic conditions, and still others require extended periods of time to grow crystals containing the therapeutic agent. By contrast, the present synthetic PCA drug delivery vehicle can be prepared at ambient temperatures and physiologically relevant pHs (see Example 4). Accordingly, a wide variety of biologically active materials that might be destroyed during the preparation of standard calcium phosphate materials can be incorporated into the drug delivery material of the present invention. Protein agents in particular are often sensitive to heat and other unfavorable conditions; the present synthetic PCA material therefore constitutes a particularly improved delivery system for protein agents.

Cells

Where the PCA material of the invention is to be utilized in a cell seeding application, the hydrated precursor is preferably prepared with an aqueous solution that is a physiological medium. Examples of such media are well known in the art (e.g., Dulbecco's minimal essential medium; phosphate buffered saline; and carbonate, TRIS, or HEPES-buffered solutions); and those of ordinary skill are aware of particular media that are compatible with desired cell types.

Of course, it is not essential that the hydrated precursor be prepared with a buffered aqueous solution rather than water. However, as it is desirable to maintain cell viability, a hydrated precursor or hardened PCA material that has been prepared using water (or other minimal aqueous solution) will preferably be exposed to growth medium prior to, or at least coincident with, its exposure to cells. Introduction of a material into an animal can constitute exposure of the material to growth medium (and to cells).

The PCA material of the present invention may be prepared with any of a variety of additives, and/or may be prepared as a composite. For examples of desirable PCA material composites, see U.S. application entitled "Bioactive Ceramic Composites" and filed on even date herewith; for examples of biologically active materials that can be incorporated into the PCA material before or after cell seeding, see U.S. application entitled "Delivery Vehicle" and filed on even date herewith. In some cases, it will be particularly desirable to add factors to the PCA material that can affect cell growth, differentiation, and/or localization. For example, laminin, fibronectin, collagen, matrigel and its components, and other growth factors and extracellular matrix components.

Cells

The PCA material of the present invention may be seeded with any of a variety of cells. A "cell", according to the present invention, is any preparation of living tissue, including primary tissue explants and preparations thereof, isolated cells, cells lines (including transformed cells), and host cells. Preferably, autologous cells are employed, but xenogeneic, allogeneic, or syngeneic cells are also useful. Where the cells are not autologous, it may be desirable to administer immunosuppressive agents in order to minimize rejection. In preferred embodiments, such agents may be included within the seeded composition to ensure effective local concentrations of the agents and to minimize systemic effects of their administration. The cells employed may be primary cells, explants, or cell lines, and may be dividing or non-dividing cells. Cells may be expanded ex-vivo prior to introduction into the inventive PCA material. Autologous cells are preferably expanded in this way if a sufficient number of viable cells cannot be harvested from the host.

Any preparation of living cells may be use to seed the PCA material of the present invention. For example, cultured cells or isolated individual cells may be used. Alternatively or additionally, pieces of tissue, including tissue that has some internal structure, may be used. The cells may be primary tissue explants and preparations thereof, cell lines (including transformed cells), or host cells. Where the cells are host cells and are introduced into the inventive PCA material in vivo (see below), preferred sources of cells include, but are not limited to, the inner layer of the periosteum or perichondrium, blood or other fluids containing the cells of choice, and damaged host tissue (particularly bone or cartilage) that includes such cells.

Any available methods may be employed to harvest, maintain, expand, and prepare cells for use in the present invention. Useful references that describe such procedures include, for example, Freshney, *Culture of Animal Cells: a Manual of Basic Technique*, Alan R. Liss Inc., New York, N.Y., incorporated herein by reference.

The PCA material of the invention is useful as a scaffold for production of hard or soft tissues. Tissue-producing or -degrading cells that may be incorporated into the material include, but are not limited to, chondrocytes, osteocytes, osteoblasts, osteoclasts, mesenchymal stem cells, other bone- or cartilage-producing cells or cell lines, fibroblasts, muscle cells, hepatocytes, parenchymal cells, cells of intestinal origin, nerve cells, and skin cells.

Methods of isolating and culturing such tissue-producing or -degrading cells, and/or their precursors, are known in the art (see, for example, Vacanti et al., U.S. Pat. No. 5,041,138; Elgendy et al., *Biomater.* 14:263, 1993; Laurencin et al., *J. Biomed. Res.* 27:963, 1993; Freed et al., *J. Cell. Biochem.* 51:257, 1993; Atala et al., *J. Urol.* 150:745, 1993; Ishaug et al., *J. Biomed. Mater. Res.* 28:1445, 1994; Chu et al., *J. Biomed. Mater. Res.* 29:1147, 1995; Thomson et al., *J. Biomater. Sci. Polymer Edn.* 7:23, 1995, each of which is incorporated by reference).

For example, mesenchymal stem cells, which can differentiate into a variety of mesenchymal or connective tissues (including, for example, adipose, osseous, cartilagenous, elastic, and fibrous connective tissues), can be isolated, purified, and replicated according to known techniques (see Caplan et al., U.S. Pat. No. 5,486,359; Caplan et al., U.S. Pat. No. 5,226,914; Dennis et al., *Cell Transplantation* 1:23, 1992, each of which is incorporated herein by reference). Such mesenchymal cells have been studied in association with tricalcium phosphate and hydroxyapatite carriers and have been found to be capable of successful differentiation from within such carriers (see Caplan et al., U.S. Pat. No. 5,197,985, incorporated herein by reference). Similar procedures are employed to direct mesenchymal cell differentiation within PCA material scaffolds of the present invention.

Of course, the present invention is not limited to the use of tissue-producing cells. Certain preferred embodiments of the invention utilize such cells, primarily because the inventive PCA material is so well suited to tissue-regeneration applications (particularly with those involving growth of bone and/or cartilage). Any cell may be seeded into the PCA material of the invention. In some cases, it will be desirable to include other cells in addition with tissue-producing cells.

The cells that are seeded into the inventive PCA material may be genetically engineered, for example to produce a protein or other factor that is useful in the particular application. In preferred embodiments, cells may be engineered to produce molecules that impart resistance to host immune attack and rejection. The Fas-L and CR-1 genes are examples of useful such genes.

Other Components

When the inventive PCA material is used in a cell seeding application, one or more additives may be introduced into the PCA material before or after seeding. In certain preferred embodiments of the invention, one or more biologically active agents is incorporated into the PCA material. For discussion of such biologically active agents and their use in conjunction with the inventive PCA material, see U.S. application entitled "Delivery Vehicle" and filed on even date herewith.

Preferred biologically active agents for use in the seeded PCA material compositions of the present invention include factors that influence cell growth, differentiation, migration, and/or localization. For example, bone matrix contains a variety of protein factors that influence cell behavior (see, for example, Hubbell, *Bio/Technology* 13:565, 1995; Caplan et al., U.S. Pat. No. 4,609,551; Caplan et al., U.S. Pat. No. 4,620,327).

Also, cell matrix components can play important roles in division, differentiation, migration, and localization (see, for example, Hubbell, *Bio/Technology* 13:565, 1995). It may therefore be desirable to localize such matrix components within the seeded PCA material of the present invention. However, many of the functions achieved by association between cells and cell matrix components (e.g., definition of cell shape, achievement of cell polarity and organization, etc.) may well be accomplished by cell attachment directly to the inventive PCA material.

Other biologically active agents that are preferred for use in certain embodiments of the invention include nutrients, angiogenic factors, compounds that enhance or allow ingrowth of the lymphatic network or nerve fibers, etc. Immunomodulatory factors, and particularly inhibitors of inflammation, may be included where it is desirable to inhibit a host response to the implanted composition. Drugs may also be included.

Generally, cells are introduced into the PCA material of the present invention in vitro, although in vivo seeding approaches are employed in some circumstances (see below). Cells may be mixed with the hydrated precursor paste or putty prior to hardening or, alternatively, may be introduced into the PCA material composition after it has hardened. In either case, it is important that adequate growth (or storage) medium be provided to ensure cell viability. If the composition is to be implanted for use in vivo after in vitro seeding, sufficient growth medium must be supplied to ensure viability throughout, and for a short time following, the implant proceeding. Once the composition has been implanted, the porous nature of the PCA material allows the cells' nutritional requirements to be met by the circulating fluids of the host.

We have found Dulbecco's minimal essential medium to be particularly useful in the practice of the present invention. Other solutions that may be employed include, but are not limited to, phosphate-buffered saline; carbonate-, HEPES-, or TRIS-buffered solutions. In some cases, additional growth-stimulating components, such as serum, growth factors, amino acid nutrients, sugars, and salts, may be added to the aqueous solution employed in the present invention. However, it is generally desirable to avoid additives, as they can alter the hardening process of the inventive PCA material. If a particular collection of additives were selected to be used but had negative effects on PCA material characteristics, the precise PCA formulation can be varied and tested for its ability to satisfy hardening parameters in the presence of the additives.

Any available method may be employed to introduce the cells into the PCA material. In many cases, it will be desirable to introduce the cells into the hydrated precursor, before hardening. For example, cells may be injected into the hydrated precursor (preferably in combination with growth medium), or maybe introduced by other means such as pressure, vacuum, or osmosis. Alternatively (or additionally), cells may be layered on the hydrated precursor, or the hydrated precursor may be dipped into a cell suspension and allowed to remain there under conditions and for a time sufficient for cells to impregnate or attach to the material. Generally, it is desirable to avoid excessive manual manipulation of the cells in order to minimize cell death during the impregnation procedure. For example, in most situations it will not be desirable to manually mix or knead the cells with the PCA material paste; however, such an approach is perfectly useful in those cases in which a sufficient number of cells will survive the procedure. Cells may also be introduced into the hydrated precursor in vivo simply by placing the material in the body adjacent a source of desired cells. In some cases, it may be desirable to enhance such in vivo cell impregnation by including within the material an appropriate chemotactic factor, associative factor (i.e., a factor to which cells bind), or factor that induces differentiation of cells into the desired cell type.

Rather than being introduced into the hydrated precursor, cells may be introduced into the PCA material of the invention after it has hardened. Because the material is porous, cells are able to readily migrate into it. Cells may be introduced into the hardened PCA material by any available means. For example, cells may be layered on the material, or may be introduced by pressure, vacuum, or osmosis. Alternatively (or additionally), the hardened material may be placed in a cell suspension and maintained there under conditions and for a time sufficient for the cells to impregnate the material. Furthermore, the hardened PCA material may be prepared with a mold or as a composite with a leachable material (e.g., sugars, salt crystals, or enzyme-degradable fillers) to provide seeding chambers or areas within the device. In such approaches, the cells are preferably introduced into these chambers through a pipette or a syringe. Cells may also be introduced into the inventive hardened PCA material in vivo, by placing the material in the body adjacent to a source of desirable cells or cell precursors as described above for the hydrated precursor. In preferred embodiments, the hardened material is placed adjacent the periosteum or perichondrium, or is exposed to blood, fluids, or damaged host tissue that contains the desirable cells.

As those of ordinary skill will readily appreciate, the number of cells to be introduced into the inventive material (be it the hydrated precursor or the hardened PCA material) will vary based on the intended application of the seeded material and on the type of cell used. Where dividing autologous cells are being introduced by injection into the hydrated precursor, use of 20,000–1,000,000 cells per cm$^3$ are expected to result in cellular proliferation and extracellular matrix formation within the material. Where non-dividing cells are employed, larger numbers of cells will generally be required. In those cases where seeding is accomplished by host cell migration into the material in vivo, exposure of the material to fluids containing cells (e.g., bone-forming cells), or to tissue (e.g., bone) itself has proven to be effective to seed the material with cells without the need for inoculation with a specified number of cells.

Modification of Delivery Kinetics

One advantage of the PCA material present invention is that the rate of resorption of the material can be modulated through modifications in the preparative methods. Specifically, methods that lead to a more dense hardened product will generally result in a slower resorption time of the pure inventive PCA calcium phosphate in vivo. In this regard, there are a variety of ways to alter the density or resorption kinetics of the hardened product. These include adjustment of the volume of liquid used to create the paste, alteration of grain size of the starting materials, and compression of the paste during hardening. Composites, in which leachable or biodegradable particles or materials are incorporated into the paste, and ultimately the hardened PCA material, may also be prepared. The leachable or biodegradable materials may subsequently be removed (e.g., by leaching) from the hardened material in vivo, so that a highly porous implant is produced. Additionally, the inventive PCA material may be prepared with a distribution of densities within the same implant. One way this may be accomplished is by preparing in vitro-hardened PCA material of one density, pulverizing the hardened material to a desired grain size, and then mixing the pulverized material with a second PCA material paste designed to produce a different density PCA material. PCA materials made in this way will resorb asynchronously.

The use of overall smaller grain size material to prepare the PCA material precursor powder results in a longer time to resorb and/or reossify in vivo (see Examples 5 and 19). Since the ACP precursor is generally prepared at a very small grain size, when two components are used to produce the inventive vehicle, the grain size of the other non-ACP component is generally used to adjust resorption time. In this regard, the grain size may be adjusted by using a ground and sieved second component to select a specific grain size distribution for addition to the final mixture. In another embodiment, the second component is ground with the ACP for varying amounts of time to affect the resorption rate.

Composite materials with altered resorbability kinetics are produced by incorporating into the PCA material an "erosion rate modifier", which is a material whose presence alters the rate of resorbability of the device as a whole. Erosion rate modifiers that increase the rate at which the drug delivery device resorbs include any leachable or biodegradable compound that affects the solubility (e.g., by altering the porosity) of the device over time in vivo. Erosion rate modifiers that decrease the rate at which the drug delivery device resorbs include crystalline calcium phosphates, particularly hydroxyapatite, and diphosphate compounds.

Another way that the rate of resorption of the inventive PCA material can be modulated is through the action of osteoclast and/or macrophage cells. Osteoclasts, and possibly macrophages, naturally digest bone. According to the present invention, osteoclast or macrophage cells, or factors that modulate their development and/or activity, can be administered in conjunction with an inventive PCA material implant to accelerate or retard the rate of PCA material resorption.

For example, any agent that directly or indirectly (e.g., through osteoblasts) stimulates osteoclast activity or development may be employed to increase the resorption rate of a PCA material implant. Conversely, any agent that directly or indirectly inhibits osteoclast activity or development may be employed to reduce the resorption rate of an implant. Such stimulatory and inhibitory agents are well known in the art (see, for example, Athanasou, *J. Bone Joint Surg.*, 78-A:1096, 1996 and Roodman *Endocrine Rev.* 17:308, 1996, each of which is incorporated herein by reference). For example, interleukin-1 (IL-1), colony stimulating factors (CSFs) such as macrophage (M)-CSF, transforming growth factor α (TGFα), tumor necrosis factor (TNF), interleukin 6 (IL-6), interleukin-11 (IL-11), interleukin-3 (IL-3), para-thyroid hormone (PTH), vitamin D3 metabolites (e.g., calcitriol), prostaglandins (under certain, known conditions), and oxygen free radicals are known to stimulate osteoclast development and/or activity. Where CSFs are utilized, subsequent administration of 1,25-dihydroxyvitamin $D_3$ can further stimulate osteoclasts; by contrast, concomitant administration of colony stimulating factors and 1,25-dihydroxyvitamin $D_3$ inhibits osteoclast.

Other factors that inhibit osteoclast development and/or activity include transforming growth factor-β (TGFβ), γ-interferon, interleukin-4 (IL-4), nitric oxide, antibodies, for example, against the osteoclast vitronectin receptor, calcitonin, and prostaglandins (under certain, known conditions).

Of course, it is also possible to introduce osteoclasts themselves (or osteoclast precursor cells, preferably in combination with agents that stimulate their differentiation into osteoclasts) into a PCA material implant in order to stimulate its resorption.

Agents that alter PCA material resorption rate may be administered systemically or locally. Local administration is preferably accomplished by introducing the agent into, or associating the agent with, the material itself, preferably according to the procedures described herein. Where local administration is being employed, it is preferred that diffusion of the agent away from the PCA material implant be minimized. For example, relatively insoluble agents are preferred because it is less likely that they will diffuse away from the implant and exert undesirable effects on other cells within the body.

Applications

As alluded to above, the cell seeded PCA material of the present invention can be usefully employed in any of a variety of in vivo and in vitro systems. For example, the material may be used to deliver biologically active agents or cells to any of a variety of sites in a body (preferably a human body, though veterinary applications are also within the scope of the invention. Alternatively or additionally, the material may be used in bone tissue or repair applications or augmentation plastic therapy in vivo. The material may also be employed as a cell encapsulation membrane or matrix, or in artificial organ construction or repair.

In vitro, the material may be used as a three dimensional cell culture matrix, and as a model for analyzing osteoclast, osteoblast, chondrocyte, and/or macrophage cultures, progenitor cell differentiation, and/or reossification and calcium phosphate resorption. The material is particularly useful for tissue formation and/or degradation studies, for example employing cells such as progenitor cells, stem cells, osteocytes, osteoclasts, osteoblasts, chondrocytes, macrophages, myoblasts, and fibroblasts. The material may also be employed to accomplish in vitro delivery of a biologically active agent.

Certain preferred applications are discussed in more detail below, but the discussion is intended only for purposes of exemplification and is not intended to be limiting.

When used as an in vivo or in vitro delivery vehicle, the PCA material of the present invention offers the advantage of controlled, localized delivery. As is well known, smaller amounts of biologically active agent are required when the agent is delivered to a specific site rather than administered systemically. Furthermore, potential toxic side effects of the agent are minimized when the agent is delivered from the delivery vehicle of the present invention. Also, the agent's activity is maximized because it is protected within the delivery vehicle until it is delivered to its site.

The PCA material of the present invention can be injected or implanted into any acceptable tissue. Oral formulations are also considered within the scope of the invention. Preferred delivery sites include sites in bone, muscle, the spinal cord, the central nervous system, the interperitoneal cavity, subcutaneous locations, and the vitreous and aqueous humor of the eye. When the PCA material is delivered to a site under circumstances where implant migration is a concern, anchoring sutures or hooks may be incorporated into the vehicle so that it can be attached and maintained in position. When appropriate, the PCA material may be anchored by insertion into a bony site (see below). Particular applications and preferred delivery sites are discussed in more detail below:

Delivery of Biologically Active Agents to Bony Sites

Figure 9:
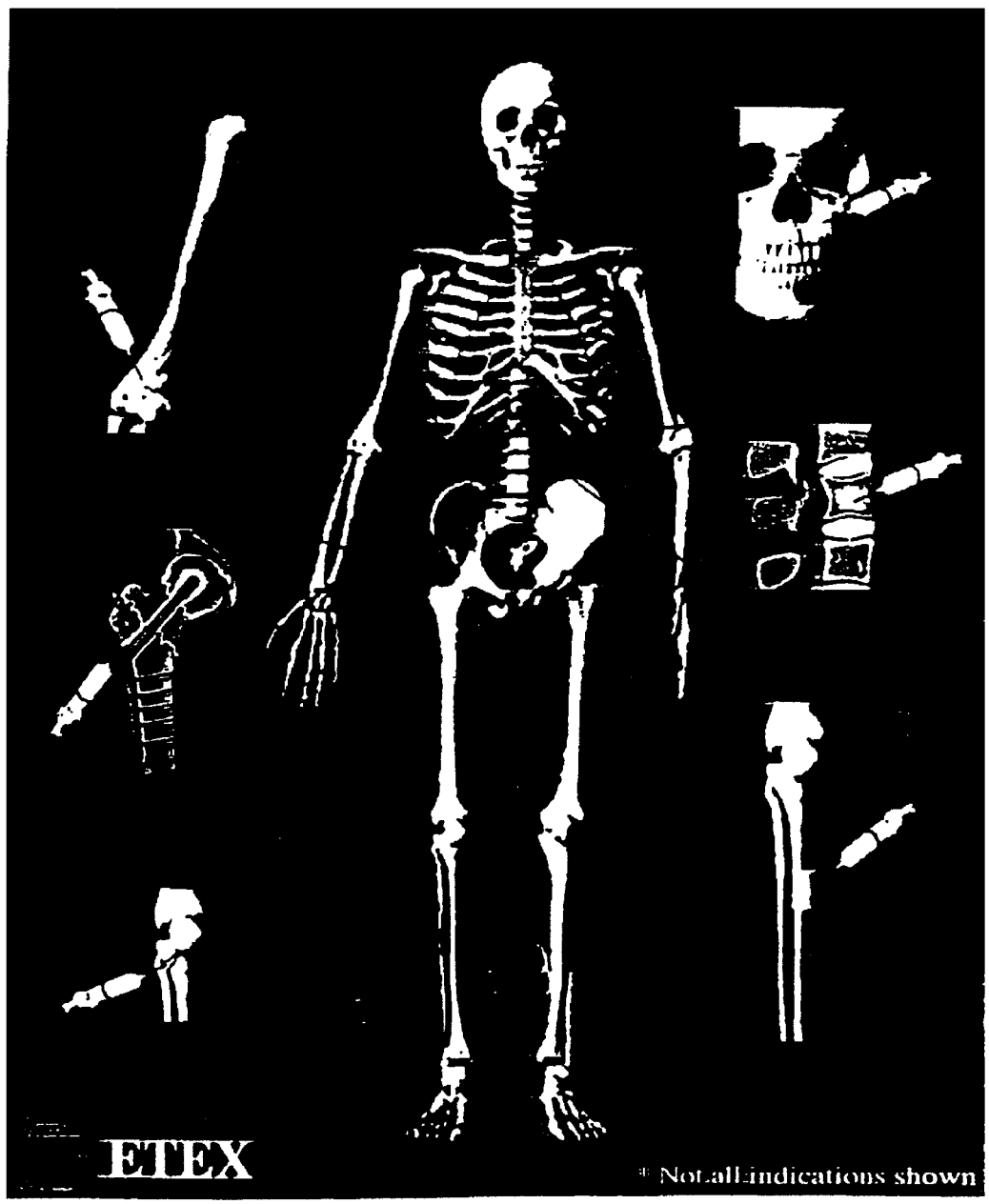
FIG. 9 depicts use of the PCA material of the present invention in a variety of bony sites.

The PCA material of the present invention has particular advantages for delivery of biologically active agents to sites in bone. Implantation of a delivery vehicle formed from PCA material of the present invention in a bony site may alternatively or additionally be utilized to anchor a delivery vehicle and accomplish systemic drug delivery, or may be utilized to accomplish delivery to a site adjacent to, though not strictly speaking "within", the bone. FIG. 9 depicts many useful applications of the PCA material of the present invention in bony sites.

Naturally-occurring bone mineral is made of nanometer-sized, poorly-crystalline calcium phosphate with apatitic structure. However, unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formulae,

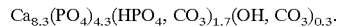

$Ca_{8.3}(PO_4)_{4.3}(HPO_4, CO_3)_{1.7}(OH, CO_3)_{0.3}$.

Bone mineral non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones. It is the Ca/P ratio in conjunction with nanocrystalline size and the poorly-crystalline nature that yields specific solubility property of the bone minerals. And because bone tissues undergo constant tissue repair regulated by the mineral-resorbing cells (osteoclasts) and mineral-producing cells (osteoblasts), solubility behavior of minerals is important in maintaining a delicate metabolic balance between these cells activities.

The PCA material of the present invention is a nano-size, poorly crystalline solid with a Ca/P ratio comparable to that of natural bone minerals. The material is bioresorbable, can be produced at low temperatures, and is readily formable and injectable. For all of these reasons, the inventive material is particularly well suited for drug delivery in bony sites. Furthermore, this synthetic PCA material can support bone growth so that it is eventually replaced by the patient's own bone. It should be borne in mind, however, that bone ingrowth may well affect the resorbability rate of the drug delivery material of the present invention. Accordingly, it may be desirable in certain circumstances (e.g., where the biologically active agent must be delivered according to a precise, predetermined administrative schedule) to reduce bone growth into the drug delivery vehicle, for example by blocking penetration of osteocytic or chondrocytic cells or precursors. In most circumstances, ossification can be avoided by placing the device at some distance away from bone. Generally, 1 mm will be sufficient, although greater distances are preferred. Also, compounds such as Indian hedgehog gene and gene products, parathyroid hormone-related protein (PTHRP) and PTHRP receptor agonists may be included in, on, or adjacent to the drug delivery device in order prevent bone growth.

In other circumstances, such bone ingrowth can desirably be encouraged. As shown in Examples 14, 17, and 18, the PCA calcium phosphate material can be placed into bony sites and allowed to resorb in a manner that results in its apparent complete (100%) replacement with new bone. Where optimal ossification is desired, the devices and objects may be seeded with bone forming cells (see below). This goal is most easily accomplished by placing the device in contact with a source of the patient's own bone forming cells. Such cells may be found in bone tissue or in bone-associated blood or fluids, including exogenous fluids which have been in contact with bone or bone materials or regions, including the periosteum, cancellous bone or marrow. In the case of devices such as screws and pins, the introduction of which into bone is accompanied by bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction bone forming cells harvested from the patient into the graft, or incorporation of trophic factors or bone growth inducing proteins into, or onto the device. Non-autologous bone cells are also within the scope of the invention if the desired amount of bone regeneration occurs prior to host rejection of the bone forming cells. In this regard, immunosuppressants may be administered to the device recipient, in some cases by incorporation into the device. Thus, cells or tissues obtained from primary sources, cell lines or cell banks may all be useful in certain embodiments.

Certain categories of biologically active agents are expected to be particularly suitable for delivery to bony sites. For example, where the drug delivery vehicle is applied to a damaged bone site, it may be desirable to incorporate bone regenerative proteins (BRPs) into the vehicle. BRPs have been demonstrated to increase the rate of bone growth and to accelerate bone healing (see, for example, Appel et al., *Exp. Opin. Ther. Patents* 4:1461, 1994). Exemplary BRPs include, but are in no way limited to, Transforming Growth Factor-Beta (TGF-β), Cell-Attachment Factors (CAFs), Endothelial Growth Factors (EGFs), OP-1, and Bone Morphogenetic Proteins (BMPs). Such BRPs are currently being developed by Genetics Institute, Cambridge, Mass.; Genentech, Palo Alto, Calif.; and Creative Biomolecules, Hopkinton, Mass. Bone regenerative proteins and trophic factors can also be used to stimulate ectopic bone formation if desired. The inventive PCA material containing BMP-7 can be placed subcutaneously, and bone formation will occur within 1–2 months.

Antibiotics and antiseptics are also desirably delivered to bony sites using the PCA drug delivery vehicle of the present invention. For example, one of the major clinical implications arising from bone-graft surgery is a need to control the post-operative inflammation or infection, particularly infection associated with osteomyelitis. An embodiment drug delivery device of the present invention, including an antibiotic, could be used as (or in conjunction with) an improved bone graft to reduce the chances of local infection at the surgery site, contributing to infection-free, thus faster, bone healing process. The efficacy of antibiotics is further enhanced by controlling the resorption of the poorly crystalline hydroxyapatite such that it dissolves at a rate that delivers antibiotic peptides or its active component at the most effective dosage to the tissue repair site.

Exemplary antibiotics include, but are in no way limited to, penicillin, tetracycline, kanamycin, gentamycin, chlortetracycline hydrochloride (aureomycin), minocyline, dosycycline, vanomycin, bacitracin, neomycin, erythromycin, streptomyan, cephalosporins, chloramphenicol, oxytetracycline (terramycine), and derivatives thereof. Antibiotics and bone regenerating proteins may be incorporated together into the PCA material of the present invention, to locally deliver most or all of the components necessary to facilitate optimum conditions for bone tissue repair.

Other biologically active agents that are desirably delivered to bony sites include anti-cancer agents, for example for treatment of bone tumors (see, for example, Otsuka et al., *J. Pharm. Sci.* 84:733, 1995). The drug delivery vehicle of the present invention is particularly useful, for example, where a patient has had a bone tumor surgically removed because the synthetic, PCA material of the present invention can improve the mechanical integrity of the bone site while also treating any remaining cancer cells to avoid metastasis. Exemplary anti-cancer agents include, for example, methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busuflan, carmustine, lomusline, dacarbazine (DTIC: dimethyltriazenomidazole carboxamide), fluorouracil, 5-fluorouracil, cytarabine, cytosine arabinoxide, mercaptopurine, 6-mercaptopurine, thioguanine.

Additional biologically active agents that can desirably be incorporated into the synthetic PCA drug delivery system of the present invention for delivery to bony sites are agents that relieve osteoporosis. For example, amidated salmon calcitonin has been demonstrated to be effective against osteoporosis.

Vitamin D and Vitamin K are also desirably delivered to bony sites, as are angiogenic factors such as veg f, which can be used when it is desirable to increase vascularization.

Bone Production and Healing

In preferred embodiments of the present invention, the PCA material is seeded with bone-forming cells or precursors thereof. Preferably, the PCA material is formulated, and the cell population is selected, so that the PCA material becomes ossified within a period of about 4–12 weeks.

In particularly preferred embodiments of the invention, the seeding is accomplished by placing the PCA material in contact with a source of the host's own bone-producing cells. Such cells are found in bone tissue or in bone-associated blood or fluids, including exogenous fluids that have been in contact with bone (including cancellous bone), bone materials, or bone regions such as the periosteum or the marrow.

Various modes of introducing the PCA material of the invention into bony sites are thoroughly described in U.S. application entitled "Orthopedic and Dental Ceramic Implants" and filed on even date herewith. Where the PCA material is to be implanted into a bony site in vivo in a manner that induces bleeding, such bleeding can effectively introduce bone-forming cells into the material so that no further seeding is required. Approaches that induce bleeding include those in which the PCA material is formed into a screw or pin, or is applied in conjunction with a screw or pin made from another material.

Where the PCA material is used as or in conjunction with a plate that opposes only cortical bone, it is preferred that a periosteal lesion be introduced in a manner that creates contact between the PCA material and the lesion, so that cells may penetrate into the PCA material from the lesion. Similarly, in some embodiments of the invention, it will be useful to surgically prepare a PCA device seating within the bone by removing a portion of cortical bone at the implant site. Cells at the implant site will migrate into and seed the PCA material.

Of course, it is not required that the PCA material devices be seeded by in vivo impregnation of the host's own cells. Bone forming cells harvested from the host may be introduced in vitro into the device, so that a seeded composition is implanted in the host. Furthermore, seeding with non-autologous bone cells is also within the scope of the invention, but care must be taken to ensure that a desired amount of bone growth occurs prior to host rejection of the bone forming cells. Such non-autologous cells can be obtained from any of a variety of sources, including but not limited to primary sources, cell lines, and cell banks.

Bone formation in and around the PCA material can be enhanced by the incorporation of trophic factors and/or bone-growth inducing factors into, or onto, the PCA material device.

Osseous Augmentation

Seeded PCA compositions of the present invention are useful for the enhancement or alteration of the shape of bony structures (e.g., a chin). For such applications, the PCA material may be supplied either as a pre-hardened shape or a molded putty form and applied to a bony surface. Generally, PCA material formulations selected for augmentation applications will be those that resorb on a relatively slower time course, typically requiring 6–12 weeks for resorption.

PCA material employed in augmentation applications are typically seeded through application of cells or cell lines to the PCA material, although some preferred embodiments involve host cell seeding. The term "host cell seeding" encompasses any method by which cells of the host are introduced into the PCA material. For example, the term encompasses migration of host cells into a device implanted in vivo, as well as assisted migration accomplished by placing bone blood or fragments of the periosteum on or in contact with the device (in vivo or in vitro), among other things.

Cartilage Production and Healing

Damage to cartilage can result in serious physical deformations. Currently, the most common treatment for loss of cartilage is replacement with a prosthetic material, but many difficulties have been encountered with this approach. As put by one of the leaders in the field. "The lack of truly biocompatible, functional prostheses can have profound and tragic effects for those individuals who have lost noses or ears due to burns or trauma". Seeded PCA compositions of the present invention offer an attractive alternative in which the PCA material acts as a formable scaffold into and within which tissue can grow. The PCA material is bioresorbable so that, eventually, the PCA material implant can be replaced with natural tissue; the negative effects of long-term prosthetic implants can therefore be avoided.

The PCA material of the present invention can be seeded with cartilage-forming cells in order to optimize chondrogenesis. Preferably, this seeding is accomplished by placing the device in contact with a source of the host's own cartilage-forming cells (e.g., chondrocytes) or precursors thereto. Such cells are found in cartilage-associated blood or fluids, including exogenous fluids that have been in contact with cartilage or cartilagenous materials. Thus, fluids that have been in contact with the perichondrium, cartilage, or marrow typically contain such cells.

In many cases, e.g., a PCA material device designed for augmentation of a damaged ear, seeding can be accomplished by placing the PCA device in contact with the breached region of the perichondrium. In other cases, it will be useful to surgically prepare a seating for the PCA device within existing cartilagenous tissue by removing a portion of the cartilage at the implant site.

In some embodiments of the present invention, additional steps may be taken to augment chondrogenesis associated with the seeded PCA material. For example, cartilage-forming cells harvested from the patient may be introduced into the device in addition (or as an alternative to) cells that impregnate it after implantation in vivo. Alternatively or additionally, trophic factors or cartilage growth-inducing factors may be incorporated into or onto the device.

It should be clear that autologous cells are not required for the seeded PCA compositions employed in cartilage-forming applications; non-autologous cells are also within the scope of the invention so long as the cells are selected and the PCA material is formulated so that a desired amount of cartilage regeneration occurs prior to host rejection of the cartilage-forming cells. Thus, cells or tissues obtained from primary sources, cells lines, or cell banks are useful in the practice of this embodiment of the present invention.

Ectopic Bone or Cartilage Production

The seeded PCA material compositions of the present invention can be used to produce bone or cartilage formation at a site at which bone or cartilage does not normally occur. Introduction of a PCA composition into which bone- or cartilage-producing cells have been seeded into an in vivo implant site will result in bone or cartilage formation at that site. In preferred embodiments, the PCA material contains growth and/or trophic factors in addition to the seeded cells, so that maintenance of the ectopically-formed bone or cartilage can be prolonged. Once it has been produced, such ectopic tissue may either be left in place or may be surgically removed, depending on its intended use. Alternatively or additionally, trophic or growth factors external to the implant may be provided, e.g., through the use of encapsulated cells, polymer implants, or other method of factor delivery (see, for example, Aebischer et al., U.S. Pat. No. 4,892,538; Sefton, U.S. Pat. No. 4,353,888 and Winn et al. *Experimental Neurology* 140:126 (1996)).

Ectopic tissues may be formed in vitro using inventive seeded PCA material compositions. Preferably, a hydrated precursor is prepared, is shaped by hand or through the use of a mold or form, and is subsequently hardened at an elevated temperature (27–50° C.). Alternatively, the PCA material may first be hardened and subsequently be machined or otherwise formed into a desired shape. Cell seeding can be accomplished by any of the methods described herein, so that ectopic tissue will be formed in vitro in the desired shape. Generally, to ensure that the shape is maintained during cell growth, it will be desirable to inhibit the action of degredative enzymes and cells, as is known in the art.

Cell Encapsulation Matrix

The PCA material of the present invention provides an excellent growth matrix for use within the cell encapsulation environment. Use of this material can prevent cell settling, provide cell dispersion, and optimize nutrient localization by encapsulated cells. Thus, according to the invention, cells may be encapsulated within encapsulation devices in the presence of the hydrated precursor or hardened PCA of the present invention, and the resultant encapsulated devices may then be implanted in vivo for use in encapsulated cell therapy applications. Useful techniques for preparing and using cell encapsulation devices are described in, for example, Winn et al., *Expt. Neurol.* 140:126, 1996 and Aebischer, U.S. Pat. No. 4,892,538; Sefton, U.S. Pat. No. 4,353,888, and Kordower et al., *Cell Transplantation*, 14:155, 1995, each of which is incorporated herein by reference.

Research Applications

The PCA material of the present invention, due to its ease of preparation, mild formation conditions, sparing solubility in most aqueous systems, and tractability for use in cell-embedding applications, provides an attractive three-dimensional growth matrix for use in research and production tissue culture applications. Furthermore, the material is useful for tissue formation and/or degradation studies (e.g., of bone or cartilage). Preferably, the material employed in such studies in seeded with cells such as (but not limited to) progenitor cells, stem cells, osteocytes, osteoclasts, osteoblasts, chondrocytes, macrophages, myoblasts, and fibroblasts.

Diagnostics

Cell-seeded PCA materials of the present invention may be employed in diagnostics that detect various health or disease states. For example, the inventive PCA material can be used in qualitative or quantitative assays to determine the bone- or cartilage-forming potential of cells taken from a patient to be diagnosed. The inventive material can also be used in diagnostics to assay vascularization and hard tissue degradation. Various soft tissue diagnostics are also made possible with the inventive PCA material compositions.

Delivery of Biologically Active Agents to Subcutaneous Implant Sites

Application of the present drug delivery device is not limited to bony sites, of course. In non-bony sites, the device is known resorb without ossification.

Placement of the instant delivery device subcutaneously is particularly useful for more systemic administration of biologically active compounds. The administration of estrogens and/or progesterones for the used in fertility control is an example of a subcutaneous application. Additionally, the administration of antigens and/or vaccines may be accomplished through subcutaneous implantation.

Delivery of Biologically Active Agents to Central Nervous System

The delivery of therapeutic substances to the central nervous system may be accomplished with the inventive delivery vehicles. Useful therapeutic substances include the delivery of γ-aminobutyric acid to epileptic foci, the delivery of L-dopa or dopamine in the striatum or substantia nigra for the treatment of Parkinson's disease, the delivery of growth factors for the prevention of neural degeneration such as GDNF in the lateral ventricles, striatum or substantia nigra for the treatment of Parkinson's disease, the administration of NGF to cortical and other regions for the treatment of Alzheimer's disease, or the administration of CNTF to the sacral or lumbar spinal cord for the treatment of amyelolateral sclerosis.

Other: Delivery of Biologically Active Agents to Sites

Other potential delivery sites include intramuscular, interperitoneal, and occular areas.

EXAMPLES

Example 1

Preparation of Reactive Amorphous Calcium Phosphate

This example describes the step-by-step preparation and methods to render relatively inert amorphous calcium phosphate solids into a highly reactive amorphous calcium phosphate of the present invention.

Solution A was prepared at room temperature by the rapid dissolution of 55 g $Na_2HPO_4 \cdot 7H_2O$ (sodium phosphate), 50 g NaOH (sodium hydroxide), 30 g $NaHCO_3$, (sodium bicarbonate) and 2 g $Na_4P_2O_7 \cdot 10H_2O$ in 1.3 l of distilled water. Solution B was prepared at room temperature by rapid dissolution of 43 g $Ca(NO_3)_2 \cdot 4H_2O$ (calcium nitrate tetrahydrate) and 1 g $MgCl_2 \cdot 6H_2O$ in 0.5 l of distilled water.

The inert carbonated amorphous calcium phosphate was then prepared at room temperature by the rapid addition of solution B to rapidly stirring solution A. The precipitate of gel-like amorphous calcium phosphate thus formed was immediately filtered using filter paper (0.05 sq. m) with medium filter speed and a vacuum pressure of about $10^{-2}$ torr. The material formed a thin cake and was washed with approximately 4 liters of distilled water by adding water into the filtrating funnel. The washed material was then collected using spatula and immersed into a liquid nitrogen in a 2.5 L container. Following the formation of hard frozen pieces, the container was transferred into a vacuum chamber for 24 hrs ($10^{-1}$–$10^{-2}$ torr), until a fine and dry powder was obtained.

Although the procedure described above may be performed at room temperature, the entire process preferably takes place below ambient temperature (4–5° C.), so as to further prevent the amorphous state from converting into more stable crystalline form. Further, such elements or ions known to act as inhibitors of crystalline hydroxyapatite formation may be added into the solution in trace amounts.

An infrared spectrum of the inert amorphous material at this point in the process contains peaks characteristic of P—O groups (600 and 1000 $cm^{-1}$), $CO_3^{2-}$ group (1,420–1, 450 $cm^{-1}$) with relatively large peak of O—H group (~3,550 $cm^{-1}$). X-ray diffraction pattern of the same material show amorphous nature of the material as demonstrated by absence of any sharp peaks when the measurement of crystallinity is determined by taking ratio of coherent peaks to background.

The inert amorphous material described above was then made into a reactive form by heating for 60 minutes at 450° C. (±3° C.). The IR of the heated material (not shown) shows reduction of particular O—H and $CO_3^{2-}$ groups, indicating significant reduction of $H_2O$ and $CO_3^{2-}$ as $CO_2$ and $H_2O$. In similarly prepared samples the carbon content was observed to drop approximately 60% with a total carbonate ratio decreasing from 1.56% to 0.5%. Note, however, that the amorphous nature of the material was not lost during this process, as demonstrated by the X-ray diffraction pattern shown in FIG. 4(a). The Ca/P ratio measurement of this material after the heat treatment was determined to be 1.575, using a method of quantitative electron microprobe analysis (FIG. 2). The overall morphological and ultrastructural properties of amorphous material is shown in FIG. 1, as seen under a transmission electron microscope. Note the "amorphous" appearance of the material with absence of sharp edges separating each granules with certain portion of the material to exhibit shapeless form (arrows). An extremely high specific surface area of 120 $m^2/g$, with an average pore size of approximately 130 Å was observed in this material.

Example 2

Preparation of Reactive Amorphous Calcium Phosphate

The preparation was conducted as described in Example 1 above, with the exception that the preparation of Solutions A and B was replaced by the following reactions. Solution A was prepared at room temperature by the rapid dissolution of 90.68 g of $Ca(NO_3)_2 \cdot 4H_2O$ in 1.2 liter of carbonated distilled $H_2O$. Solution B was prepared by dissolving 40.57 g of $K_2HPO_4$ in 1.53 liters of distilled $H_2O$, containing 24 ml of 45 vol. % KOH solution. Chemical and physical properties of the product amorphous calcium phosphate resulting from this procedure were similar to those of the material prepared accordingly for Example 1.

Example 3

Preparation of Reactive Amorphous Calcium Phosphate

The preparation was conducted as described in Example 1 above, with the exception that the preparation of Solutions A and B were replaced by the following reactions. Solution A was prepared at room temperature by the rapid dissolution of 10.58 g of $Ca(NO_3)_2 \cdot 6H_2O$ in 0.15 liters of carbonated distilled $H_2O$ at pH greater than 9.0, as adjusted by NaOH. Solution B was prepared by dissolving 7.8 g of $(NH_4)_2HPO_4$ in 0.35 liters of distilled $H_2O$. Chemical and physical properties of the product amorphous calcium phosphate resulting from this procedure were similar to those of the material prepared according to Examples 1 and 2.

Example 4

Preparation of Synthetic Poorly Crystalline Apatitic Material from Reactive Amorphous Calcium Phosphate This example describes the preparation of PCA material of the invention.

The dicalcium phosphate dihydrate (DCPD) used in this example was prepared in the following manner. Solution A was prepared at room temperature by rapid dissolution of 10 g $H_9N_2O_4P$ (diammonium hydrogen phosphate) in 500 ml distilled water at a pH of 4.6–4.8.

Solution B was prepared at room temperature by the rapid dissolution of 17.1 g $Ca(NO_3)_2 \cdot 4H_2O$ (calcium nitrate tetrahydrate) in 250 ml distilled water. The dicalcium phosphate dihydrate was prepared at room temperature by the rapid addition of solution B to the stirring solution A. Immediately thereafter, the sample was filtered using filter paper (0.05 sq. m) with medium filter speed and a vacuum pressure of about $10^{-2}$ torr. The material formed a thin cake which was washed with about 2 liters of distilled water and then air dried at room temperature for 24–72 hrs.

The reactive amorphous calcium phosphate material prepared from Example 1 was physically dry-mixed with dicalcium phosphate dihydrate ($CaHPO_4 \cdot 2H_2O$) at 50:50 wt % using a mortar and pestle for 3–5 min. Water (1 ml/g of mixed material) was then added to the powder mixture to yield a paste-like consistency. The amount of $H_2O$ added varied, depending on whether a thick or thin paste was desired. The paste material was then wrapped in moist tissue paper and was hardened into a solid mass by heating 37° C. The hardening process could be delayed for several hours by wrapping the sample in parafilm and holding it at 4° C. Also, hardening can be allowed to proceed at ambient temperature, although setup times may then be expanded.

The hardened material was composed of nanometer-sized, poorly crystalline apatitic calcium phosphate with an inherent solubility property that exceeded reported solubilities for a synthetic hydroxyapatite material. This is demonstrated in FIG. 3, where the concentration of calcium ions released into a controlled pH buffer solution over 24 hrs at 37° C., was significantly higher for the PCA material of the present invention (curve 50) than the standard crystalline hydroxyapatite material (curve 52).

Example 5

Preparation of Synthetic, Poorly Crystalline Material from Precursors of Selected Particle Size This example demonstrates the preparation of synthetic PCA materials using precursors having a selected particle size.

DCPD was prepared as described in Example 4. The dry material was ground for 5 minutes in a SPEX 8510 laboratory mill with a SPEX 8505 alumina ceramic grinding chamber. Following grinding the material was serially sieved through a Tyler test sieve shaker to produce DCPD with 8 different grain size distributions as indicated in Table 1.

TABLE 1

DCPD Grain Size Distribution

| Sample | Grain Size Distribution | Extent of hardening at 30 min, 37° C. |
|---|---|---|
| 10-1 | <25 $\mu$m | hard |
| 10-2 | 25–35 $\mu$m | hard |
| 10-3 | 35–53 $\mu$m | hard |
| 10-4 | 53–63 $\mu$m | hard |
| 10-5 | distribution B3 | hard |
| 10-6 | 106–125 $\mu$m | not fully hardened |
| 10-7 | distribution B2 | not fully hardened |
| 10-8 | unsieved distribution B1 | not fully hardened |

It has been found that the preliminary grinding of DCPD prior to sieving can be replaced by a brief hand grinding using a mortar and pestle without substantially changing the results.

The reactive amorphous calcium phosphate material prepared from Examples 1, 2, or 3 was physically dry-mixed 1:1 (wt/wt) with DCPD for 10 minutes using a SPEX 8510 laboratory mill with a SPEX 8505 alumina ceramic grinding chamber. Water (1.0–0.8 ml/gm of dry mix) was then added to the powder mixture to yield a paste-like consistency. 5 of the 8 samples indicated in Table 1 hardened well in 30 minutes at 37° C. Samples 6, 7 and 8 did not harden as quickly or as firmly as the other samples. Each of these samples had significantly higher percentages of >100 $\mu$m particles than did the other samples. It is concluded from these observations that the use of smaller grain size DCPD leads to more rapid and complete hardening within larger grain size DCPD.

Example 6

Preparation of Synthetic PCA Material from Reactive Amorphous Calcium Phosphate

Figure 3:
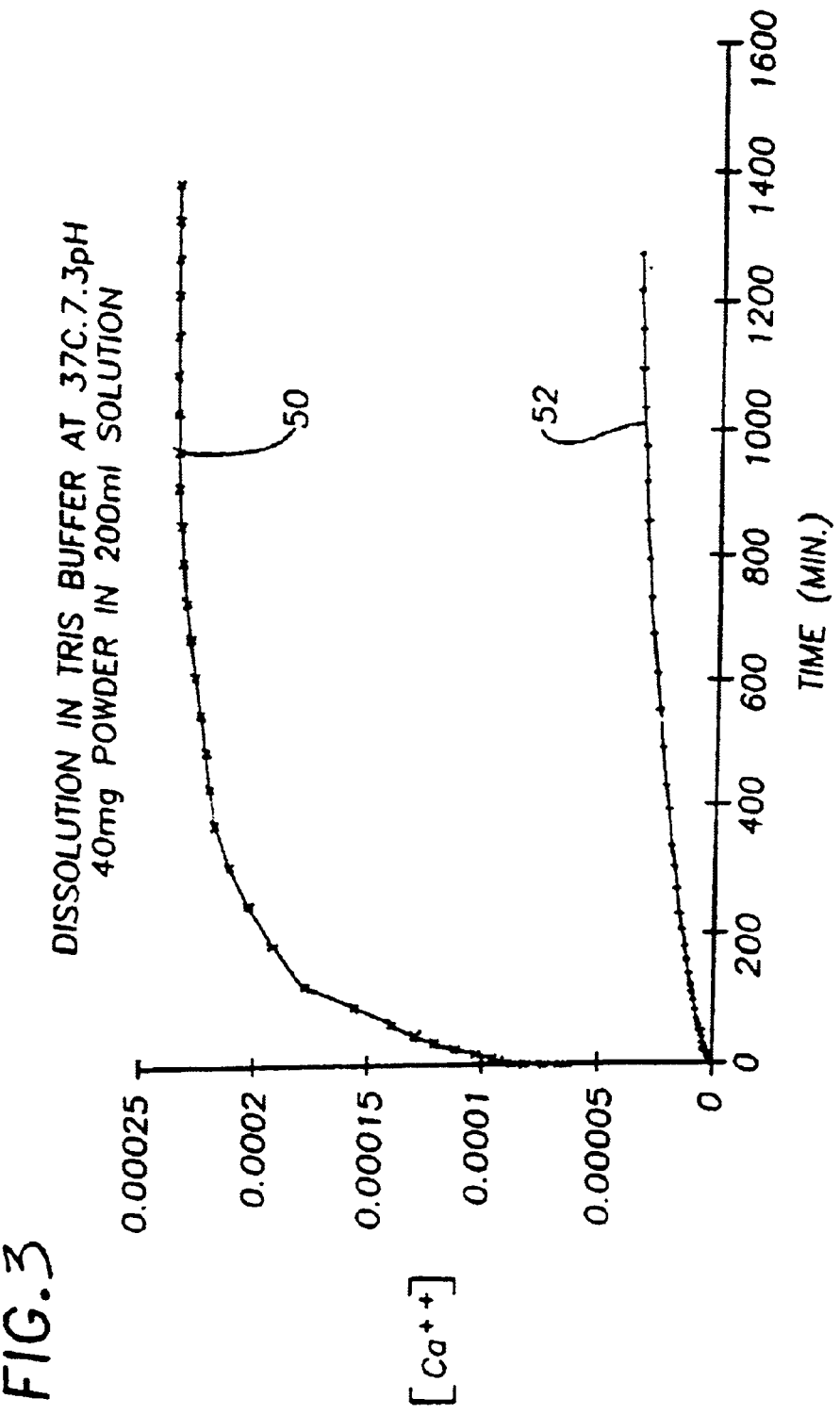
FIG. 3 is a solubility curve of a poorly crystalline apatitic calcium phosphate product derived from amorphous calcium phosphate of the present invention, as compared with a crystalline hydroxyapatite. Note the relative higher solubility of the material of the present invention versus a more crystalline form of hydroxyapatite, as measured by the amount of calcium ions released into solution at 37° C.

Reactive amorphous calcium phosphate material as prepared in Examples 1 was dry-mixed with other calcium phosphate compounds, according to the method described in Example 4. These compounds included, but were not limited to: $Ca(PO_3)_2$ (calcium metaphosphates), $Ca_7(P_5O_{16})_2$ (heptacalcium decaphosphate), $Ca_2P_2O_7$ (calcium pyrophosphate), $Ca_3(PO_4)_2$ (tricalcium phosphates). The dry-mixture ratio was properly calculated to be between Ca/P ratios of 1.5–1.70, depending on the molar Ca/P ratio of the compound mixed with the reactive amorphous calcium. The resulting material was poorly crystalline apatitic calcium phosphate solids with solubility properties same as shown in FIG. 3.

Example 7

Preparation of an Injectable Paste for Formation of a Synthetic, PCA Material from a Reactive, Amorphous Calcium Phosphate This example describes the preparation of an injectable paste for the formation of poorly crystalline apatitic calcium phosphate solid.

The dried mixed materials prepared according to Examples 4 or 6 were mixed with distilled $H_2O$ (2.3 ml/g). A paste was formed that could be easily shaped by hand or injected through a nozzle as small as 0.5 mm ID. The flowability increased after refrigerating the paste at 4° C. for 2–3 hrs.

The material could be stored in a paste form for about 12 hours at 4° C. in an air tight container without hardening.

Example 8

Characteristics of a Synthetic Poorly Crystalline Apatitic Calcium Phosphate Material The crystalline content of the PCA material was determined by X-ray diffraction and I-R spectrometry.

FIGS. 5a–d are the X-ray diffraction spectra of the reaction product between DCPD and the reactive amorphous calcium phosphate as described in Example 4. The reaction mixture was placed in a moist environment at 37° C. and examined by X-ray diffraction spectrometry at different times. X-ray scan conditions were (a) copper anode, (b) $\lambda=1.4540598$ Å, and (c) a scan range 20–35° at a step of 0.02° and step interval of 2 seconds. FIG. 6 shows the infrared spectra of dicalcium phosphate dihydrate (a), the activated ACP of the invention (b), and the PCA material of the present invention (c).

Figure 5:
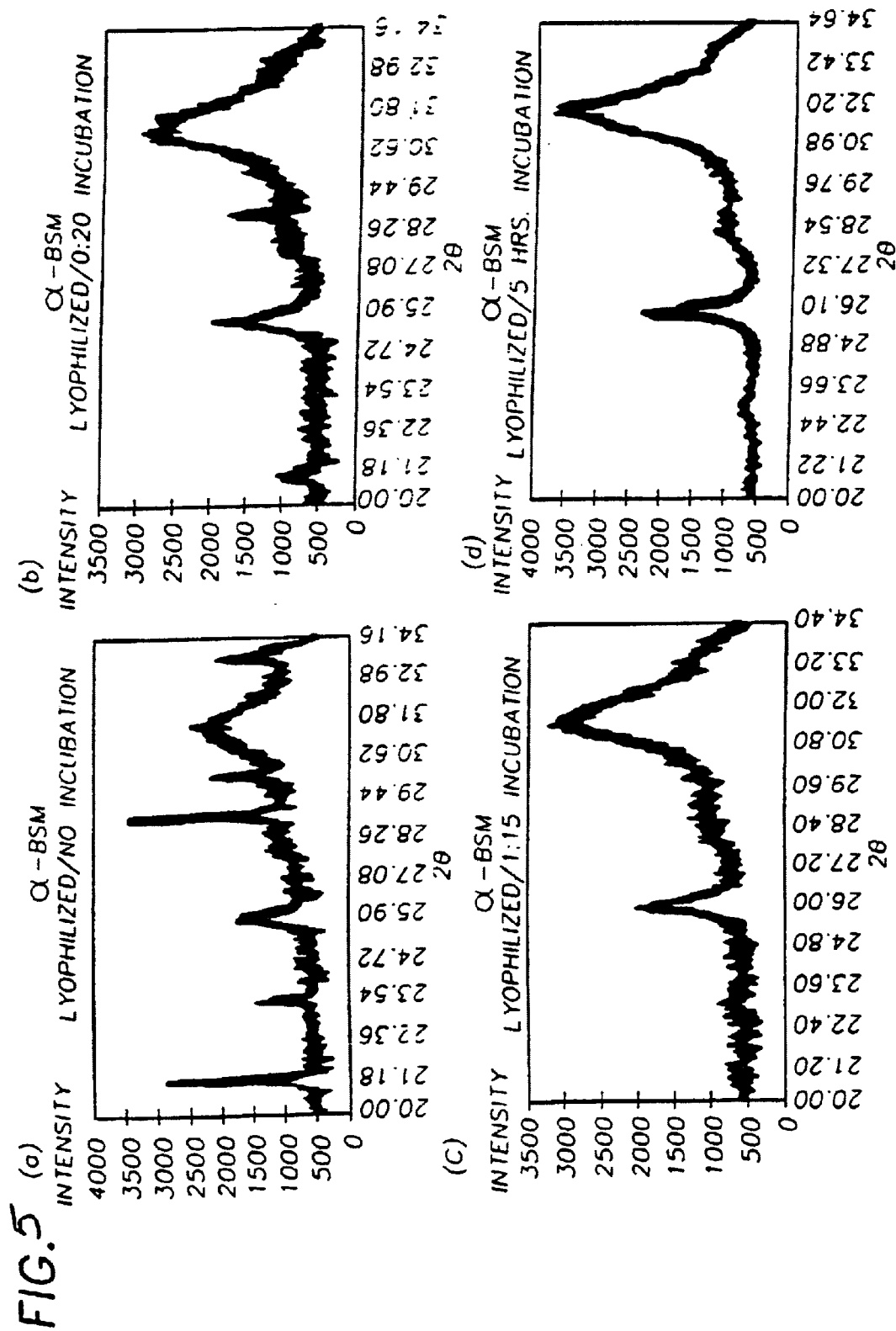
FIGS. 5a–d are X-ray diffraction patterns tracking the progress of the reaction of a mixture of reactive amorphous calcium phosphate and dicalcium diphosphate to form a PCA material of the present invention.
Figure 7:
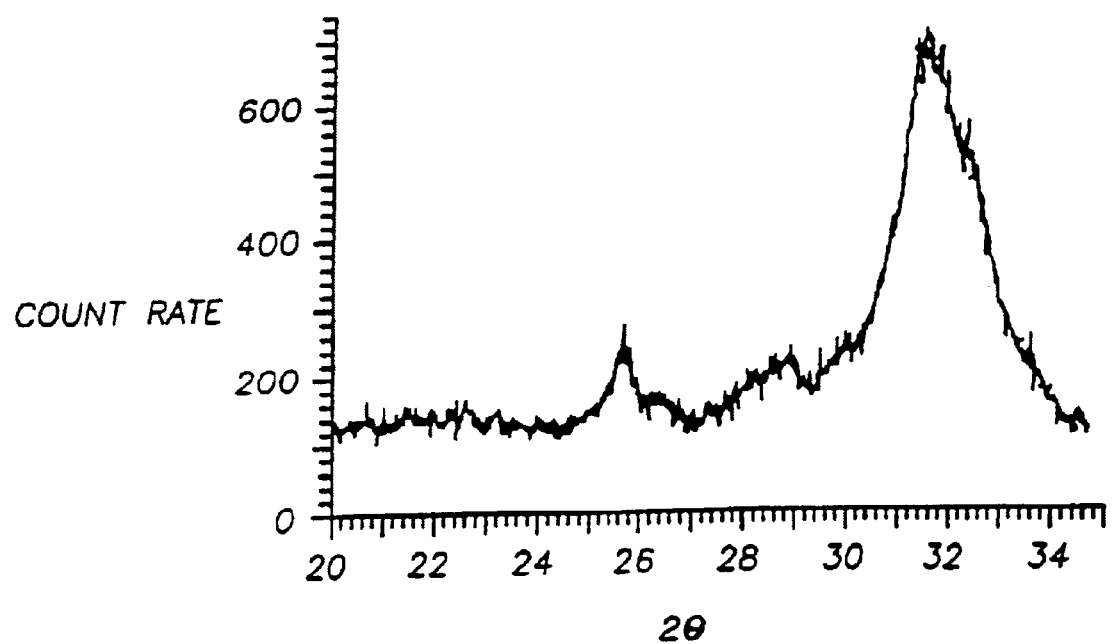
FIG. 7 is an X-ray diffraction pattern of naturally occurring bone.
Figure 8:
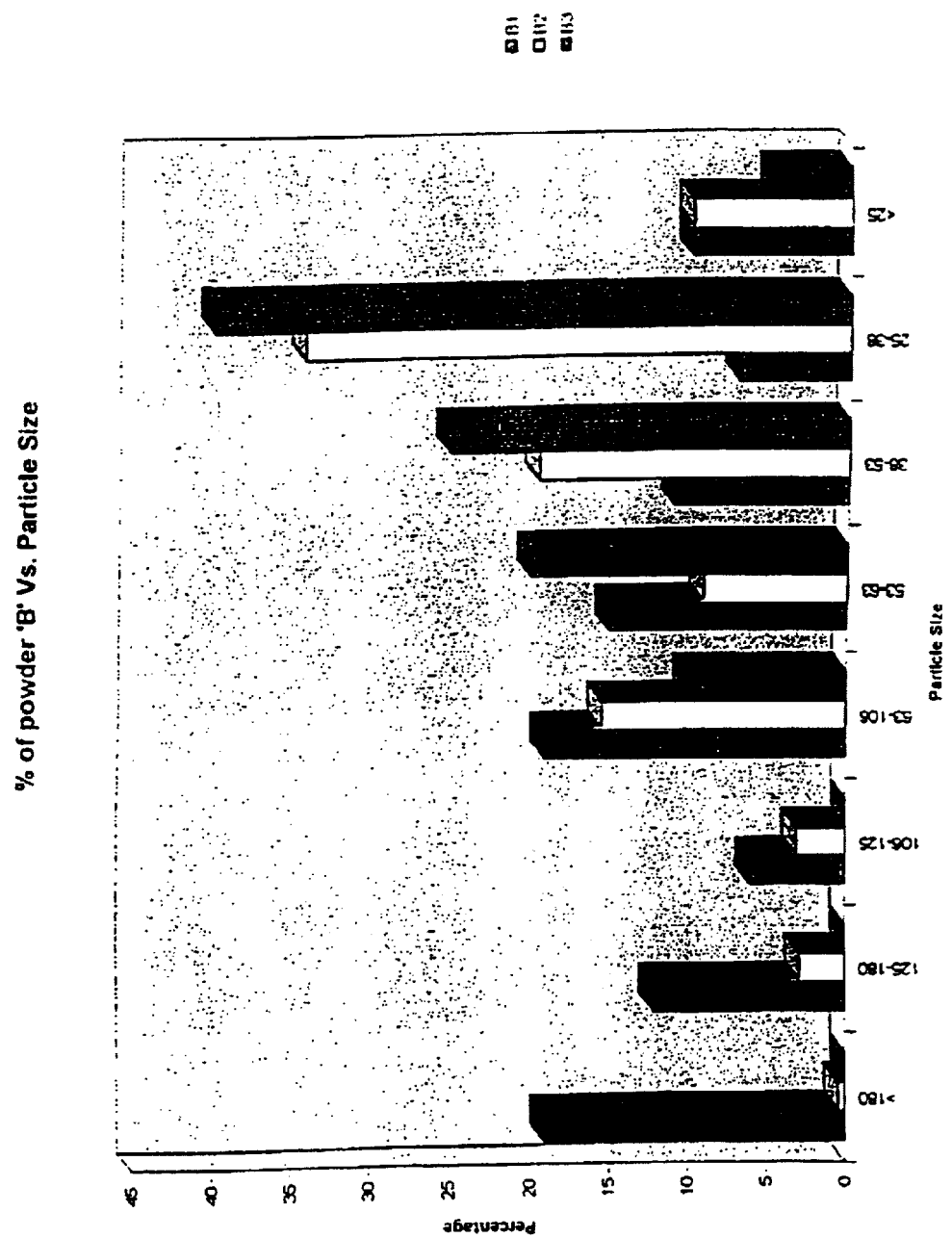
FIG. 8 is a bar graph displaying particle size distribution for various formulations described in Example 5.

Samples of FIGS. 5a–5d were incubated for 0, 20 min, 75 min and 5 hours, respectively. The samples were removed at the noted time and lyophilized to preserve chemical characteristics. FIG. 5a taken at the start of the reaction, represents a combination of peaks attributable to the starting ACP and dicalcium diphosphate (see, FIG. 4 for component XRD patterns). The sharp peaks at ca. 20.25°, 23.5°, 29.5°, 30.75° and 34.2° for crystalline dicalcium diphosphate are readily observed. With increase in reaction time, the sharp crystalline peaks subside and wide (amorphous) peaks appear centered at 26°, 28.5°, 32.0° and 33.0°. It is interesting to note that there is no significant change in the spectra after 75 minutes of reaction, indicating that the conversion reaction was essentially complete in little more than one hour. The X-ray diffraction pattern of the PCA material of the invention (FIG. 5d) can be compared to that of naturally occurring bone, shown in FIG. 7. The two spectra are nearly identical, indicating the close biomimetry of the apatitic calcium phosphate of the invention.

Examples 9–12

Characteristics of Injectable Paste for Formation of Synthetic PCA Material from a Reactive, Amorphous Calcium Phosphate These examples demonstrate the effect of fluid volume on the consistency and reactivity of injectable paste to be used in the formation of a synthetic, poorly crystalline hydroxyapatite material. Each of the pastes were prepared as described in Example 7, above, and the consistency and rate of reaction at room temperature and 37° C. were determined. Observations are reported in Table 2.

TABLE 2

Formability, injectability and reactivity of one gram drug PCA material prepared with variable water volume

| Example No. | water volume (mL) | formability | injectability | hardening time (min) (4° C./RT/37° C.) |
|---|---|---|---|---|
| 9 | 0.7 | – crumbles | – | —/—/— |
| 10 | 0.8* | +++ easily formed paste | + | >60/>60/30 |
| 11 | 0.9* | ++ toothpaste | ++ | >60/>60/30 |
| 12 | 1.0 | + liquid toothpaste | +++ | >60/>60/30 |

*Under some circumstances (e.g., evaporation) these samples may dry out somewhat over a period of one hour at room temperature. In such cases, additional water may be added to restore the original consistency.

Example 13

Infrared Spectra of Precursor and Product Materials

This example compares the infrared spectra of crystalline and amorphous precursors produced according to the Examples and the final PCA material produced by reacting similar precursors. FIG. 7a presents the IR spectrum of brushite (DCPD) prepared as described in Example 4; FIG. 7b presents the spectrum of ACP after heat treatment, prepared as described in Example 1; and FIG. 7c is the IR spectrum of the PCA material prepared as described in Example 4.

Example 14

Implantation and Resorption of PCA Material in a Bony Site

The purpose of this study was to assay resorption and ossification of PCA calcium phosphate in a bony implant site. The method is also useful for testing the resorption and ossification properties of PCA calcium phosphate formulations and composites of the invention.

The test article used was a PCA calcium phosphate formulation prepared as described in Example 4. The ACP and DCPD were mixed in the specified proportions and ground for 1 minute, 30 seconds in the SPEX grinder equipment.

Adult (>5 month old) NZW male rabbits were held in quarantine and acclimatized for a minimum of 10 days prior to the initiation of the study. Animals were individually housed in suspended stainless steel cages. Wood shavings were used in dropping pans under the cages. Prior to initiation of the study, animals were assigned to groups or treatments randomly and were identified by a numbered ear tattoo and by a corresponding cage card. All animals had single defects placed in one tibia. Timepoints for evaluations were 2, 4, and 8 weeks (2 animals at each timepoint). Surgery was performed under full anesthesia and aseptic surgical conditions.

After obtaining adequate anesthesia (e.g., ketamine/xylazine to effect), using aseptic technique, an incision was made over the lateral proximal tibia. The soft tissue was deflected away and the bone exposed. Using an approximately 5 mm trephine in a low speed dental handpiece with irrigation (0.9% physiologic saline) as needed, a ~5.5 mm diameter hole was cut through the cortical portion of the bone. The bony disk was dissected free from the cortex and the site was prepared for implantation. The hydrated precursor material in paste form was placed into the defect. Defects in control animals were left untreated. The soft tissues were then closed in layers. One sample per animal was prepared using this method.

Clinical observations of the animals' general health and well-being, with special regard to their ambulatory abilities, were made at least weekly. All animals appeared to be in good health. At the end of the study the animals were euthanized with an overdose of anesthetic and the implant site collected. Radiographs of the tibiae were made at scheduled intervals including after surgery and at the time of necropsy.

The implantation sites were fixed in formalin and stained with either hematoxylin and eosin, Masson's trichrome, or Von Kossa stained slides from decalcified samples. Undecalcified histological samples were also prepared and stained with light green basic fuschin. Slides were microscopically evaluated by a board certified veterinary pathologist (ACVP) with experience in laboratory animal pathology. Subjective observations were made of bone morphology, and presence or absence of organized bone and of detectable PCA calcium phosphate material was noted.

Figure 10A:
In FIG. 10a, the small arrows indicate one edge of the defect; the large arrowhead is at the yet unbridged defect.

Histological results indicated some mineralization at 2 weeks. By 4–6 weeks, animals receiving implants had normal trabecular bone at the implant site with no evidence of remaining PCA calcium phosphate. The untreated controls had not fully healed in that they had less then full ingrowth and/or had non-cortical-type bone. FIGS. 10a and 10b are photomicrographs of untreated and treated tibia defects, respectively, 2 weeks after surgery. As can be seen, bone to the right of the defect edge in the untreated sample (FIG. 9a) is thin trabecular bone; new bone to the right of the defect edge in the treated sample is thick trabecular bone.

Example 15

Implantation and Resorption of PCA Material in a Subcutaneous Site

This example demonstrates the resorption of the inventive PCA calcium phosphate when implanted subcutaneously into rats. It also demonstrates a useful screening procedure to test resorption characteristics of new formulations of bioceramic implant materials and composites.

Eighty male and eighty female Sprague-Dawley rats were each implanted with 4 ml (2–4 gm) of the inventive PCA (prepared according to Example 4) into the dorsal subcutis (>10×the amount considered maximal in humans on a per kg basis). Control animals were treated with an equal volume of saline. Operation procedures are described in Example 16. The rats were sacrificed according to the schedule presented below in Table 3; the implant site was examined as described in Example 16.

TABLE 3

Sacrifice Schedule

| Sacrifice Timepoint | PCA calcium phosphate implant |
|---|---|
| 1 week | 5 m/5 f |
| 2 weeks | 5 m/5 f |
| 1 month | 5 m/5 f |
| 3 months | 5 m/5 f |
| 1 year | 20 m/20 f |

Blood for clinical pathology analyses was collected via retroorbital sinus or cardiac puncture (all by the same method) while the animals were under $CO_2$ anesthesia. Blood samples were collected from each group of animals prior to scheduled sacrifice. Clinical observations of the animals for general health and well-being were performed at least weekly until 3 months, and then monthly.

At 1 week PCA material was present at the implant site and was found associated with moderate to marked granulomas presumable associated with the resorption process. At week two a small amount of PCA material was still present at the implant site and associated granulomas were mild to moderate. By week four most tissue appeared normal with a few mild granulomas persisting at the implant site. At week twelve no evidence of the implant remained.

Example 16

Implantation and Resorption of PCA Material in an Intramuscular Site

This example describes the preparation of PCA material implants that have varied in vivo resorption times as a result of varied grinding times. Individual dry precursors, ACP and DCPD were prepared as described in Example 4. Several different formulations of DCPD and ACP were then prepared by i) grinding DCPD for 15 sec, 30 sec, 1 min, 2.5 min, or 5 min in a SPEX grinder; ii) combining the ground DCPD 1:1 with ACP; and iii) grinding the mixture for an additional 15 sec, 30 sec, 1 min, 2.5 min, or 5 min, respectively. Total grinding times for the different preparations were therefore 30 sec, 1 min, 2 min, 5 min, and 10 min.

The PCA calcium phosphate, sterilized in powder form by approximately 2.5 Mrad of gamma irradiation, was prepared as described in Example 4 by taking the material in powder form and mixing with sterile water or saline and forming it into approximately 1 cm disks 2 mm thick and incubated for a minimum of 30 minutes at 37° C. Disks were implanted into adult male New Zealand White Rabbits immediately following fabrication.

Animals were assigned to dose groups which contained 3 males for a total of 15 animals. The implants were assigned to the rabbits randomly. 10–15 minutes prior to the surgery, the animal was premedicated with xylazine (10 mg/kg, i.m.). The animal was then given ketamine (50 mg/kg, i.m.). The dorsal surface of the animal was clipped free of hair and washed with a betadine surgical solution and alcohol. Before the surgery the animal was monitored to be sure that is was properly anesthetized. To do this, pressure was applied to the foot pad. When there was no response, the animal was properly anesthetized. Throughout the procedure, the animal was monitored for whisker twitching and the toe-inch reflect, which indicated that the animal was not waking up.

Using aseptic technique and a scalpel blade, an incision 1–2 cm in length was made in the skin over the m. longissimus lumborum (which lies along both sides of the spine). When the incision was made, the underlying fascia and muscle was also cut to allow the sample to pass into the muscle. The sample disk was placed directly into the muscle, being sure that the entire implant was embedded in the muscle. The muscle was closed with a single absorbable suture and the skin was stitched closed subcutaneously. Metal skin staples were used to close the external skin surface incision. Five samples were placed on each side in this manner. Each sample was placed at the end of the incision and they were approximately 1 cm apart from each other (see diagram). The samples were in the form of 7 mm by 2 mm disks weighing approximately 150 mg. The animals were monitored and were given buprenorphine (0.02–0.05 mg/jg, s.q) upon awakening. The analgesic was administered 2 times per day for three days after surgery.

The animals were radiographed immediately after the surgery and for every two weeks thereafter. The radiographs were compared to track the resorption of the materials. A standardized method was used for the radiographs to minimize any variation between timepoints.

After euthanasia, implant sites were first evaluated by gross examination. In those sites where the implant had been resorbed, area of red to tan discoloration of the muscle were observed.

Muscle tissue, with the implants, was removed, being careful not to disturb the implants. The tissues and the identifying marks were placed into labeled jars filled with 10% neutral buffered formalin. All implant sites were processed and evaluated microscopically. Observations included focal fibrosis, focal granulomatous inflammation, and appearance of the implant (in some cases). Fibrosis was primarily seen as fibrocytes and collagen. Animals with gross resorption had fibrosis and minimal to moderate granulomatous focal inflammation. Granulomatous inflammation was seen as focal aggregates of macrophages and giant cells, often with intracytoplasmic crystals, and occasional heterophils and lymphocytes. Inflammation around the non-resorbed implants was primarily minimal to mild fibrosis and/or granulomatous inflammation, both of which are within the acceptable range for intramuscular implants.

At four weeks, the pellets made from PCA calcium phosphate implants that had been prepared by grinding for 30 seconds, 1 minute, or 2 minutes were fully resorbed. Those that had been prepared by grinding for 5 minutes or 10 minutes were not fully resorbed.

Example 17

Implantation and Resorption of PCA Material in a Bony Site

The purpose of this study was to assay resorption and ossification of the PCA calcium phosphate of the invention in a bony site.

Mature (>1 year) beagle dogs were employed for this study because of their size and historical use as a model for bone studies. The tibia of the dog is large enough to allow large (>5 mm) defects to be created and studied without comprising the ability of the animal to ambulate without inducing fractures secondary to induction of defects in the bones.

Ten adult male and female beagle dogs (6.0–15.0 kg) received the same treatment; Defects were created in the lateral surface of the tibial crest cortex (8 mm or 10 mm) in each tibia. PCA calcium phosphate was placed in the defect in one tibia and the other tibia served as a control.

An incision was made over the proximal tibia. The soft tissue was deflected away and the bone was exposed. Using an 8 mm trephine in a low speed dental handpiece with irrigation (0.9% physiologic saline) as needed, the bony disk was dissected free and the site was prepared for implantation. The invention calcium phosphate material (solid or paste) was placed into the defect. The soft tissues were then closed in layers. One to three samples per animal were performed using this method. The animals were allowed to heal for scheduled periods of time.

Animals were assessed by clinical observations, radiographs, and microscopy of the defect sites at 0, 2, 4, and 8 weeks. Specifically, tibia radiographs were taken every 2 weeks throughout the study. The radiographs were used to determine the duration of the study. Approximately at the end of every 2 weeks, 2 animals were sacrificed and the test sites were removed for histology. The implantation sites were prepared as undecalcified and decalcified sections.

Two dogs were used as pilot animals and did not receive and PCA material. In these pilot animals, some healing was observed radiographically at 2 weeks. By 6–8 weeks, the defect was completely healed. The size of dog defects was determined to be optimal at 1 cm. In the remaining 8 dogs, control defects healed within 6 weeks; treated defects healed in 2 to 4 weeks. The quality of the bone in the control defects was thin trabecular bone; in the treated defects, the bone was thick trabecular to cortical type bone. Thus, the treated defects healed approximately 2 weeks faster than did untreated defects, and healed with better bone thickness.

FIG. 11 shows a highly magnified (10×) photograph of canine trabecular bone growth into a defect site treated with the PCA material of the invention 8 weeks after surgery. The small arrows denote osteoblast—like cells lining the bone spicules and are indicative of enhanced cellular activity.

FIG. 12 shows a photomicrograph of a canine cortical bone defect treated with the PCA material of the invention. The large arrows indicate one edge of the defect. The new bone growth is to the right of the defect; at 4 weeks after surgery, this growth in thick trabecular bone.

Example 18

Implantation and Resorption of PCA Material Implant in a Bony Site

The purpose of this study was to assay resorption and ossification of the PCA calcium phosphate of the invention, and to establish parameters for screening test PCA calcium phosphate materials.

Eighteen adult (>3 month old) NZW male rabbits were used in these studies. After obtaining adequate anesthesia (e.g., ketamine/xylazine to effect), using aseptic technique, an incision was made over the proximal tibia. The soft tissue was deflected away and the bone was exposed. Using an approximately 5 mm trephine in a low speed dental handpiece with irrigation (0.9% physiologic saline) as needed, the bone disk was dissected free and the site was prepared for implantation. The inventive PCA calcium phosphate material (solid, granules or paste) was placed into the defect. The soft tissues were then closed in layers.

Clinical observations of the animals general health and well-being, with special regard to ambulation, were performed weekly and in more detail at the time of the bi-weekly radiographs. Radiographs of the tibiae were made at scheduled intervals including after surgery and at the time of necropsy.

The implantation sites were prepared as hematoxylin & eosin, Masson's trichrome decalcified samples and as undecalcified slides.

Findings and clinical observations were associated with surgery and were not associated with the PCA calcium phosphate implants. Postsurgical clinical observations were within the range of anticipated findings for surgery-related trauma. Radiographs were taken immediately postsurgery and at each scheduled sacrifice timepoint.

Immediately after surgery, all bone defect sites were distinct; implants appeared to have the same radiodensity as bone. At 2 weeks postsurgery, control defects had distinct sites and implant sites were less distinct and blended into surrounding bone; similar findings were observed at 4 weeks. At 7 weeks, all sites appeared similar with increased radiodensity. Grossly, defect sites at 2 weeks were visible clearly in control and treated animals. At 4 weeks and greater, the implant or control sites could not be grossly ascertained.

Radiographic findings indicated little change in the control animals until week 7; animals treated with inventive PCA material had increasing radiodensity in the defect over time. Defects in control animals had some new bone ingrowth, predominantly of the thin trabecular type, within 4–7 weeks. Defects in treated animals had bone ingrowth as early as 2 weeks and by 7 weeks were filled with new bone. Microscopic findings are consistent with enhanced bone replacement with PCA calcium phosphate implants. Taken together, this study shows that 5 mm defects in rabbit tibia heal or have new bone growth in control animals by 7 weeks and in animals treated with the inventive PCA material by 4 weeks. Also, this rabbit unicortical 5 mm critical sized defect model is useful to analyze tests articles for there resorptive and ossificative properties.

Figure 13B:
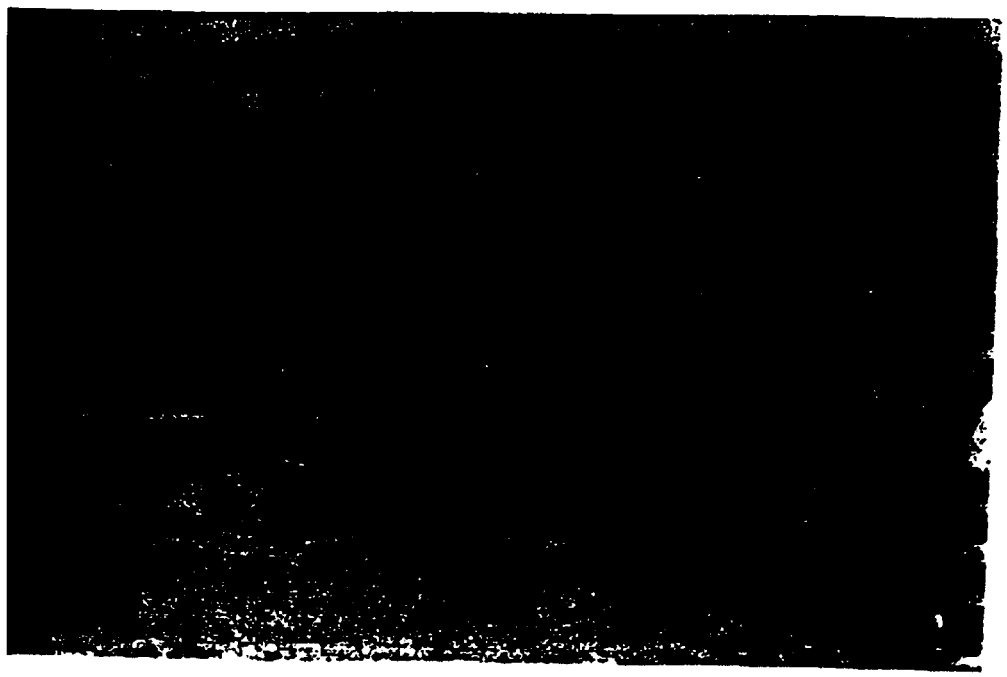
FIG. 13 presents photomicrographs of untreated (FIG. 13a) and treated (FIG. 13b) rabbit tibia defects 4 weeks after surgery (Magnification 4×; decalcified; Masson's Trichrome).
Figure 14:
FIG. 14 is a photomicrograph of a region external to a bone site in which cartilage formation has occurred (hematoxylin and eosin).

FIG. 13 shows photomicrographs of untreated (FIG. 13a) and treated (13b) rabbit tibia defects 4 weeks after surgery. The large arrow indicates the edge of the defect. In FIG. 13a, small arrows 100 denote an abundance of fibrous connective tissue on the defect site. The large arrowhead 102 points to new trabecular bone in the defect. In FIG. 13b, the two small arrows 104 demarcate the thick trabecular bone growth in the defect site.

Example 19

Variation of Resorption Rates of Synthetic PCA Materials—by Varying Particle Size PCA precursor material is prepared according to Example 5. Two precursor mixes are prepared, sample A corresponding to sample 6 and sample B is a 2:4:3:1 mix of samples 1, 2, 3, & 4. Hydrated precursor pastes of the two samples are tested in rodents in the subcutaneous test of Example 15. Resorption is monitored at various time points.

Example 20

Incorporation of a Biologically Active Agent into a PCA Material Device and Preservation of in vitro Stability This example demonstrates the incorporation of a protein into a delivery vehicle of the present invention in a manner that preserves the protein's in vitro stability.

Bovine pancreatic trypsin is prepared in phosphate buffered saline at a concentration of 100 mg/ml. 0.8 ml of this solution is added to 1 g of a 1:1 mixture of activated ACP and DCPD as described in Example 17, sample B. The mixture is formed into a ball and hardened in a moist environment at 37° C. for 30 minutes. The hardened ball is then lyophilized overnight and subsequently it is ground by and with a mortar and pestle. The powder formed this way is mixed with 1 ml of water and applied to wells in a casein assay plate. The clearance of the cloudy casein a ring around the well is compared to the clearance observed in a well similarly loaded with a lyophilized PCA sample continuing heat inactivated trypsin.

Example 21

Incorporation of a Biologically Active Agent into a PCA Material Device and Preservation of in vivo Stability This example demonstrates the incorporation of a protein in to a delivery vehicle of the present invention in a manner that preserves the protein's in vivo activity.

200 mg/ml Beta galactosidase (Worthington LS004093) is prepared in phosphate buffered saline pH 7.0. 0.8 ml of this solution is added to 1 g of a 1:1 mixture of activated ACP and DCPD (prepared as described in example 17, sample B.) and mixed into a putty. The formable PCA is then prepared in a ball and implanted subcutaneously in a rat. Two weeks later the PCA ball is removed, lyophilized and ground with a mortar and pestle. The powder is then assayed for beta galactosidase activity, for example using a liquid assay such as that described by Miller (*Experiments in Molecular Genetics, Cold Spring Harbor Laboratory Press,* Cold Spring Harbor, N.Y. 1972).

Example 22

Delivery of an Antibiotic

This example demonstrates use of the delivery vehicle of the present invention to delivery antibiotic in a dental application.

100 mg/ml gentamycin is prepared in phosphate buffered saline pH 7.0. 0.8 ml of this solution is added to 1 g of a 1:1 mixture of activated ACP and DCPD (prepared as described in Example 17, sample B.) and mixed into a putty. The formable PCA is then prepared in a ball and implanted subcutaneously in a rat. Two weeks later the PCA ball is removed, lyophilized and ground with a mortar and pestle. The powder is then assayed for bactericidal activity using a USP bacteriacidal/bacterialstasis zone of inhibition test.

Example 23

Delivery of a Vaccine

This example demonstrates use of the delivery vehicle of the present invention to delivery a vaccine.

Keyhole limpet hemocyanin is prepared at a concentration of 0.5 mg/ml in phosphate buffered saline pH 7.0 0.8 ml of this solution is added to 1 g of a 1:1 mixture of activated ACP and DCPD (prepared as described in Example 17, sample B.) and mixed into a putty. The formable CPA is then prepared in a ball and implanted subcutaneously in a rat. The process is repeated on a monthly basis for four months. Blood samples are taken on a regular basis and anti-Keyhole limpet hemocyanin antibody titers are determined by ELISA.

Example 24

Delivery of a Nucleic Acid

This example demonstrates use of the delivery vehicle of the present invention for intramuscular delivery of a nucleic acid for the purpose of cell transfection. This method may also be used to incorporate DNA into tissues other than muscle.

pUC19 plasmid DNA is prepared in EDTA TRIS pH 7.4 at 2 mg/ml. 0.8 ml of this solution is added to 1 g of a 1:1 mixture of activated ACP and DCPD (prepared as described in example 17, sample B.) and mixed into a putty. The formable PCA is then prepared in a ball and implanted intramuscularly in a rat. After 4 weeks the muscle at the implant site is dissected and histologically stained for the presence of the B galactosidase gene product.

Example 25

Implantation and Resorption of PCA Material Device for Treatment of Parkinson's Disease.

This example demonstrates use of the delivery vehicle of the present invention to deliver a drug for the treatment of Parkinson's Disease.

Primates are made hemi-parkinsonian with MPTP and evaluated behaviorally as described in Kordower et al., *Cell Transplanation* 14:155–171, 1995.

200 mg/ml GDNF is prepared in phosphate buffered saline pH 7.0. 0.8 ml of this solution is added to 1 g of a 1:1 mixture of activated ACP and DCPD (prepared as described in Example 17, sample B.) and mixed into a putty. The hydrated PCA precursor is then shaped into 3 cylinders each approximately 1 mm×1 cm and hardened in am moist environment at 37° C.

The cylinders are then placed in the lateral ventricles on the lesioned side of the experimental animals and the primates are continued to be behaviorally evaluated. After two months the animals are sacrificed and neurons of the substantial nigra and striatum are analyzed for tyrosine hydroxylase activity.

Example 26

Pre-hardened Implant: Augmentation and Resorption of the Canine Mandibular Onlay Model The purpose of this study was to evaluate resorption, ossification and biocompatibility of two formulations of the inventive PCA calcium phosphate in canine mandibular sites. Prehardened PCA calcium phosphate was implanted in a canine mandibular onlay model which additionally may be used as an augmentation model.

The test article was PCA calcium phosphate in two formulations, corresponding to Types 2 and 10 described in Example 16. The PCA calcium phosphate was pre-hardened in a moist environment at approx. 40° C. immediately prior to implantation. The control implants were 3 mm×4 mm cylinders of silicone and porous hydroxyapatite, respectively.

Two adult female hound-type does (20 to 25 kg) were used in the study. Both dogs received two control implants (1 of each) on the right side of the mandible and one each of the Type 2 and Type 10 PCA calcium phosphate formulations on the left (opposite) side.

Implantation was performed under full anesthesia and aseptic surgical conditions. The animals were premedicated with tranquilizers and atropine-type agents and induced with barbiturates. The animal's vital signs (temperature, heart, rate, respiratory rate) were monitored before and throughout the procedure. The animals were tested for proper anesthetic depth by toe pinch and corneal stimulus. After obtaining adequate anesthesia, using aseptic technique, an incision was made in the skin over the midlateral ventral surface of the mandible and proximal neck (over the mandible lower edge). The soft tissue was deflected away and the bone was exposed. The periosteum over the outer mandibular surface was elevated and the bone surface was roughened with a burr or drill until it was rough and bloody in a shape to accept the cylindrical implants. The control articles and pre-hardened PCA calcium phosphate were placed into the defects. Two samples per animal per side were onlaid onto each outer mandible surface using this method (two experimental PCA calcium phosphate samples and two controls). The samples were placed about 1 cm to insure that they do not appose each other. The periosteum was closed first using 3.0 vicryl. The soft tissues were then closed in layers with 3-0 vicryl absorbable suture. The skin was closed with simple interrupted sutures of 5-0 nylon. The animals were allowed to heal for scheduled periods of time. One dog was sacrificed at 3 weeks and the other at 3 months and the test sites were removed for histology. All animals were euthanized and identifying marks were collected.

The implantation sites were prepared as undecalcified sections. Sections were evaluated for biointegration, biodegradation, and biocompatibility.

The results wee as follows: At all time points excellent biocompatibility was observed. No giant cells and minimal macrophage were observed. There was only minimal reaction layer of only a few cells thickness at the base of the PCA calcium phosphate implants. This is significantly better than was observed for either of the controls.

At three weeks, the majority of the Type 2 material was resorbed. At twelve weeks, the Type 2 was completely resorbed to the surface of the original bone. Additionally the bone in the socket was not fully differentiated.

The Type 10 samples demonstrated osseointegration with new bone ingrowth and cell migration into the implant. The implant itself was approximately 10% resorbed after twelve weeks.

The silicon control implant, which is not resorbable, displayed a mild to moderate foreign body reaction. Voids were unfilled at three weeks, but by twelve weeks were filled with fibrous tissue. The hydroxyapatite control implant showed no signs of resorption or osseointegration within the first twelve weeks.

This experiment confirms the excellent biocompatibility of the inventive PCA calcium phosphate. Additionally, a difference in resorption time between the two PCA formulations was observed, with a prolonged resorption time course for the sample in which the precursors were mixed/ ground for a longer period of time (Type B).

The results also point out the slower resorption and ossification properties observed in the non-load bearing mandible implant site as compared to rapidly ossifying load bearing applications of Examples 14, 17 and 18.

Example 27

Ectopic Bone Production

This example describes the production of ectopic bone in an animal model using an inventive cell seeded PCA material.

The PCA material is prepared and implanted either subcutaneously or imtramuscularly as described examples 15 and 16, except that the material is not pre-hardened, the hydration medium used is 0.8 ml/gm phosphate buffered saline pH 7.4, and the material is seeded with cells as described below. In some instances 0.2 mg/ml of BMP 7 is included in the hydration medium.

Prior to implantation, the 1 g sample of hydrated PCA is inoculated using a syringe with approximately 50 µl of the subject's bone marrow harvested previously with a biopsy needle. The hydrated precursor is then implanted. Enough subjects are used to allow recovery of the PCA on a biweekly basis to study ectopic bone production.

Example 28

Production of Cartilage in vivo with Autologous Cell Seeding

This example describes the production of cartilage on the surface of bone from an inventive PCA material composition seeded with autologous cartilage-producing cells.

Figure 18:
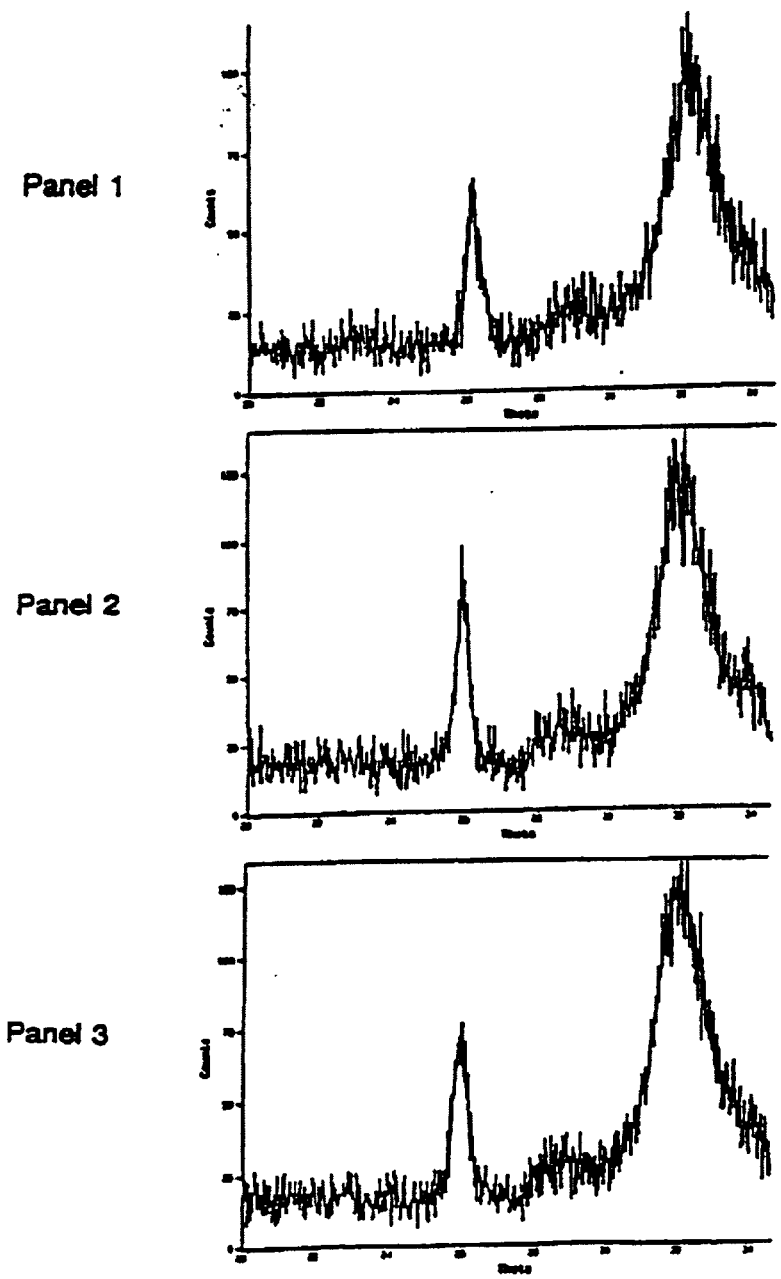
FIG. 18 shows XRT analysis of material retrieved from rabitts.
Figure 19:
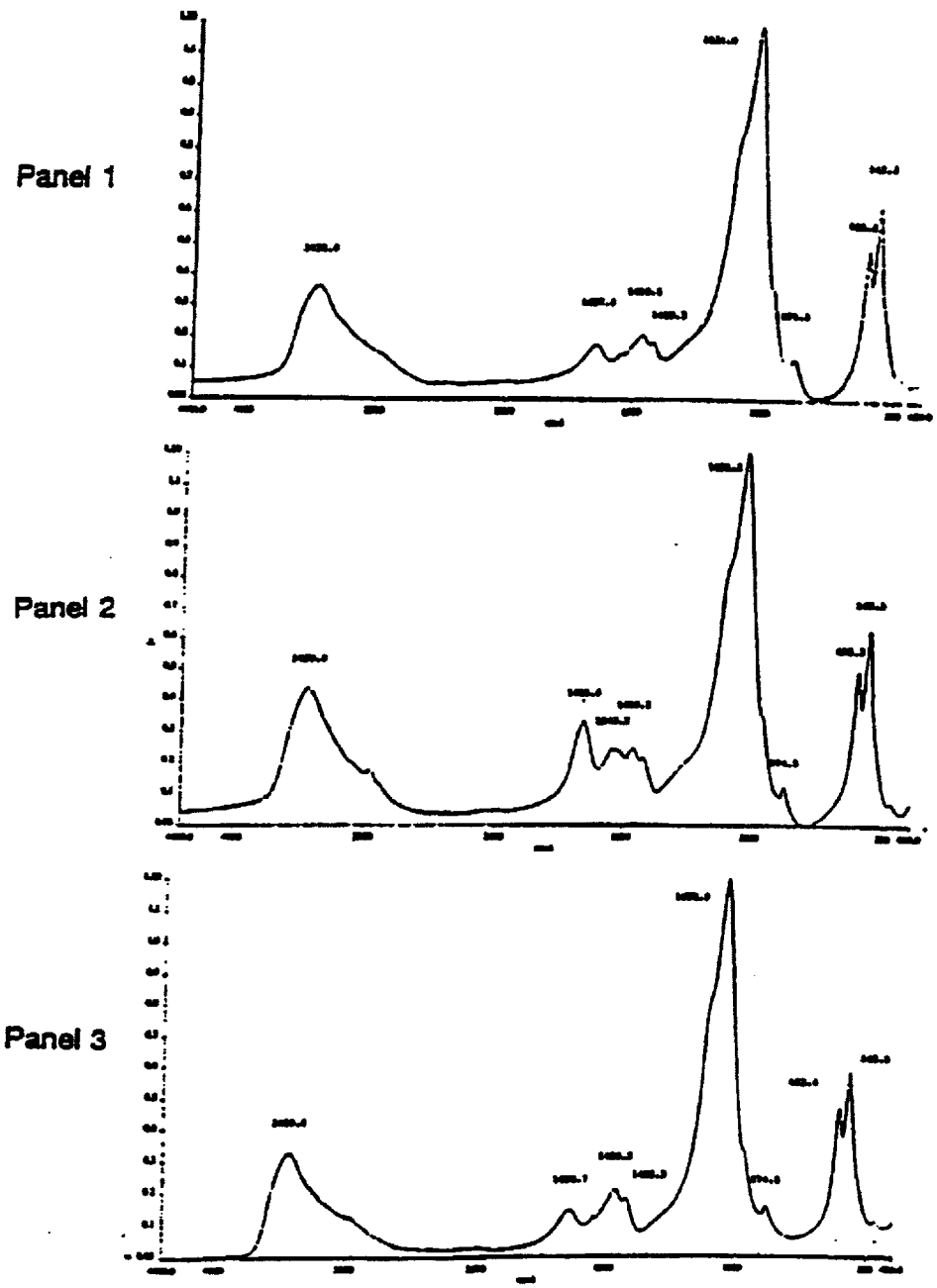
FIG. 19 shows FTIR analysis of material retrieved from rabbits.
Figure 20:
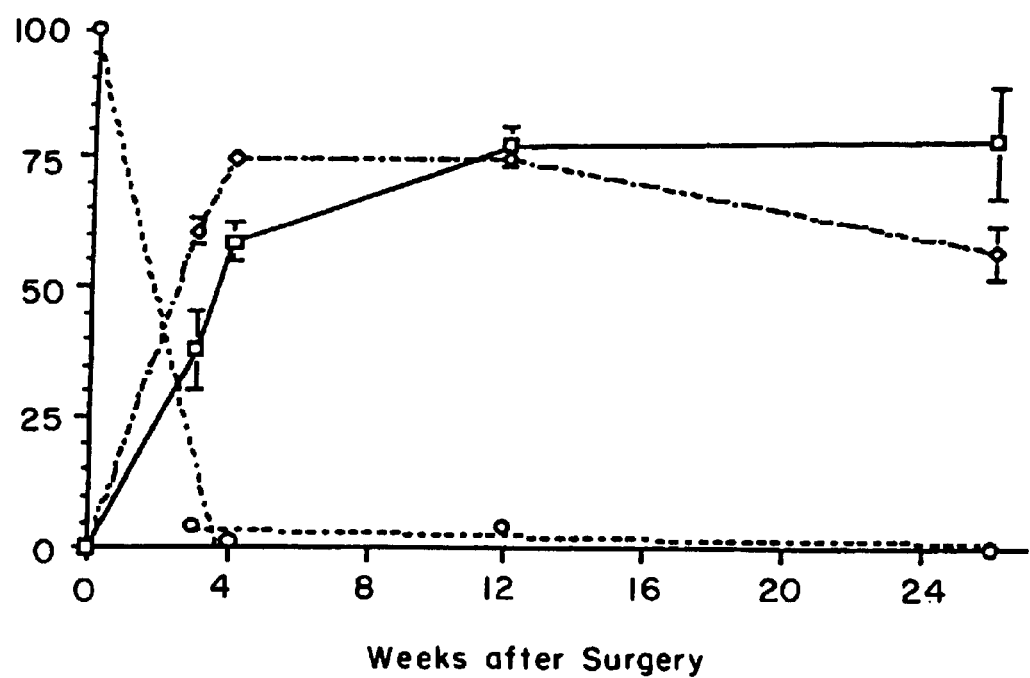
FIG. 20 shows results for new bone formation and PCA material resorption.

In a number of instances involving dogs and rabbits, unexpected formation of cartilage was observed when bone that had been treated with PCA material was histologically examined. FIG. 18 is a photomicrograph of a radial bone from a NZW rabbit, stained with hematoxylin and eosin. A small mound of PCA material had been inadvertently applied to a region of healthy bone, and the formation of cartilage is clearly observed in the center of the mound of PCA. Native bone is designated as 2 and cartilagenous region is indicated at 1.

Example 29

Production of Cartilage in vitro

This example describes the in vitro production of cartilage from a cell-seeded PCA material composition of the present invention.

Human chondrocytes are prepared and cartilage production determined according to Goldring (*Methods in Molecular Medicine Human Cell Culture Protocols,* Edited by Jones, Human Press, pp. 217–232, 1996, incorporated herein by reference); rat cell line CFK2 is maintained according to Bernier et al. (1993 *J. Bone Miner. Res.* 8: 475, 1993); and articular and intervertebral chondrocytes are prepared according to Rivard et al. (Fifth World Biomaterials Congress, pg. 291, 1996). All procedures are performed asceptically under sterile conditions.

Sterile PCA hydrated precursor is prepared according to example 5, sample 5. Hydration medium is 2 X HBSS (50 mM HEPES, 10 mM KCl, 280 mM NaCl and 12 mM glucose pH 7.5). The hydrated precursor is formed into two slabs, each of which is about 1 mm thick and approximately 1 cm square. A small indentation is prepared in the first slab, and about 25,000 cells in approximately 5 µl of growth medium containing 10% FCS are placed within the well. The second slab is placed on top of the first slab, and edges of the two slabs are gently pinched together. The resultant composition is placed in a petri dish so that it is submerged in growth medium containing 10% FCS. The petri dish is placed in an incubator at 37° C. in 5% $CO_2$. The medium is changed every three to four days. Enough replicates are prepared to analyze a sample on a weekly basis for the formation of cartilage.

Example 30

Ectopic Cartilage Formation

This example describes the production of ectopic cartilage in an animal model using an inventive cell-seeded PCA material composition.

The PCA material is prepared and implanted either subcutaneously or intramuscularly into rabbits as described in examples 15 and 16, except that the material is not pre-hardened, the hydration medium used is 0.8 ml/gm phosphate buffered saline pH 7.4, and the PCA material is seeded with cells as described below. In some instances, 0.2 mg/ml of type 1 collagen is included in the hydration medium.

Prior to implantation, the 1 g sample of hydrated PCA is inoculated with approximately 100 $\mu$l of enzymatically-isolated autologous knee joint cartilage chondrocytes. Preferably, the chondrocytes are delivered into the PCA material using a syringe. The cell-seeded hydrated precursor is implanted. Enough subjects are used to allow recovery of the PCA on a biweekly basis to study ectopic cartilage production.

Example 31

In vivo Cartilage Repair

This example describes the production of ectopic cartilage in an animal model using an inventive cell-seeded PCA material composition.

A PCA material hydrated precursor is prepared and implanted into dog knee joints in which cartilage has been surgically removed. The hydration medium used is 0.8 ml/gm phosphate buffered saline pH 7.4, and the hydrated precursor is seeded with cells as described below. In some instances 0.2 mg/ml of type 1 collagen is included in the hydration medium.

Prior to implantation, the 1 g sample of hydrated precursor material is inoculated with approximately 200 $\mu$l of enzymatically isolated autologous knee joint cartilage chondrocytes. The chondrocytes are preferably delivered by syringe. The cell-seeded hydrated precursor is implanted. Enough subjects are used to allow recovery of the PCA on a biweekly basis to study joint cartilage production.

Example 32

Cell Encapsulation Matrix

This example describes the use of inventive PCA matrices for encapsulated cell therapy. Encapsulation devices are prepared according to known methods (see Aebischer et al., U.S. Pat. No. 4,892,538; Sefton et al., U.S. Pat. No. 4,353,888, Winn et al. *Experimental Neurology* 140:126 (1996), each of which is incorporated herein by reference).

Devices are loaded with hydrated precursor paste in the presence of 15,000 fibroblasts and sealed. Devices are maintained in vitro or implanted into animal recipients. Devices are explanted periodically and checked with trypan blue for cell viability.

Example 33

In vivo Augmentation with a PCA/HA Composite

This Example demonstrates the use of a relatively slowly resorbing PCA material in a PCA/HA composite to produce a long lasting, shape-retaining skeletal augmentation.

PCA/HA composites are prepared by mixing particulate HA (grain size<200 $\mu$m) with the inventive hydrated precursor putty described in example 5, sample 5, in a ratio ranging from 0.05 to 30% wt/vol. The granular putty produced by this mixing is shaped in a form suitable for implantation. The granular putty is then hardened at 37° C.

The implant size is prepared by dissecting away a few millimeters of the cortical bone, including the periosteum. If possible, the periosteum is peeled back from the cortical bone surface at the implant site, but is left attached. The material and blood from the dissected bone is retained and mixed with fresh PCA material paste (i.e., hydrated precursor) in about a 1:3 vol/vol ratio, and is set aside. Fresh PCA material paste is used as a cement to affix the implant to exposed cortical bone surface. Additional PCA material paste is applied as needed to ensure adherence of the implant. The retained PCA/tissue material mix is then used as a seeding source for the implant and is applied to as much of the implant surface as is possible. The periosteum is then drawn back over the implant as much as possible.

Example 34

Production of PCA Calcium Phosphate Using an ACP and Participating Promoters This example demonstrates the hardening properties and PCA calcium phosphate formation from ACP using a number of different participating promoters. Highly reactive ACP was prepared according to Example 1.

The nanocrystalline hydroxyapatite of samples 1-1, 1-2 and 1-3 were prepared without inhibitors of crystallization as follows: 218 g of disodium hydrogen orthophosphate ($Na_2HPO_2.12H_2O$) were dissolved in 1200 mL of solution of distilled water. For carbonated PCA calcium phosphate of samples 1-1 and 1-2, 80 g of $NaHCO_3$ were also added to this solution. 70 g of calcium nitrate [$Ca(NO_3)_2.4H_2O$] were dissolved in 500 mL of distilled water. The calcium solution was quickly poured into the phosphate solution at room temperature with constant stirring. Precipitation was immediate and substantially complete. The pH of the precipitate was adjusted to 7.4 by the addition of sodium hydroxide solution in order to avoid the formation of acidic calcium phosphates. The precipitate was immediately separated from the solution by filtration through a Buchner filter (with a total surface about 0.1 sq.m), and was washed by about 3 liters of distilled water. A gel cake of low crystallinity calcium phosphate was obtained on the filter paper. A portion of the gel cake was immediately lyophilized for samples 1-2 and 1-3.

For sample 1-1 the gel cake was treated as follows: After filtration and washing, an appropriate amount of distilled water (5 to 80 weight %) was added to the gel precipitate. The gel was homogenized by whipping energetically for a few minutes. It was then cast into polytetrafluoroethylene (PTFE) molds (diameter 60 mm; height 2 mm), and sonicated for a few minutes in order to release the air bubbles trapped in the gel.

The molds were dried in a chamber at controlled temperature (5 to 37° C.) and humidity (10 to 95% RH). The samples shrank slowly on drying and released most of their water. The rate of drying and the shrinkage of the samples depended on the initial water content. The material hardened on drying and became glassy. It contained about 10% of residual water.

The remaining hydroxyapatites and calcium sources were used as is from commercial sources.

TABLE 4

ACP Conversion Using Participating Promoters

| sample | participating promoter | incubation at 37° C. | extent of hardening | PCA* by FTIR | PCA* by XRD |
|---|---|---|---|---|---|
| 1-1 | carbonated nanocrystalline hydroxyapatite, air dried | 30 min<br>2 hrs | starting to set<br>hard | yes | ND |
| 1-2 | carbonated nanocrystalline hydroxyapatite, lyophilized | 30 min<br>2 hrs | hard<br>hard | yes | yes |
| 1-3 | non-carbonated nanocrystalline hydroxyapatite, lyophilized | 30 min<br>2 hrs | starting to set<br>hard | yes | ND |
| 1-4 | Aldrich hydroxyapatite grain size <15–30 μm | 30 min | hard | yes | yes |
| 1-5 | Clarkson hydroxyapatite grain size >250 μm | 30 min | starting to set | yes | ND |
| 1-6 | Monetite - non calcinated grain size | 30 min<br>15 hrs | soft<br>starting to set | yes | ND |
| 1-7 | CaCO$_3$ | 30 min<br>15 hrs | starting to set | yes | ND |
| 1-8 | Ca(OH)$_2$ | 30 min<br>15 hrs | soft<br>starting to set | yes and Ca(OH)$_2$ | ND |
| 1-9 | Ca(CH$_3$COO)$_2$ | 30 min<br>15 hrs | soft<br>soft | yes | ND |

PCA = poorly crystalline apatitic calcium phosphate
ND = analysis not done

Figure 15:
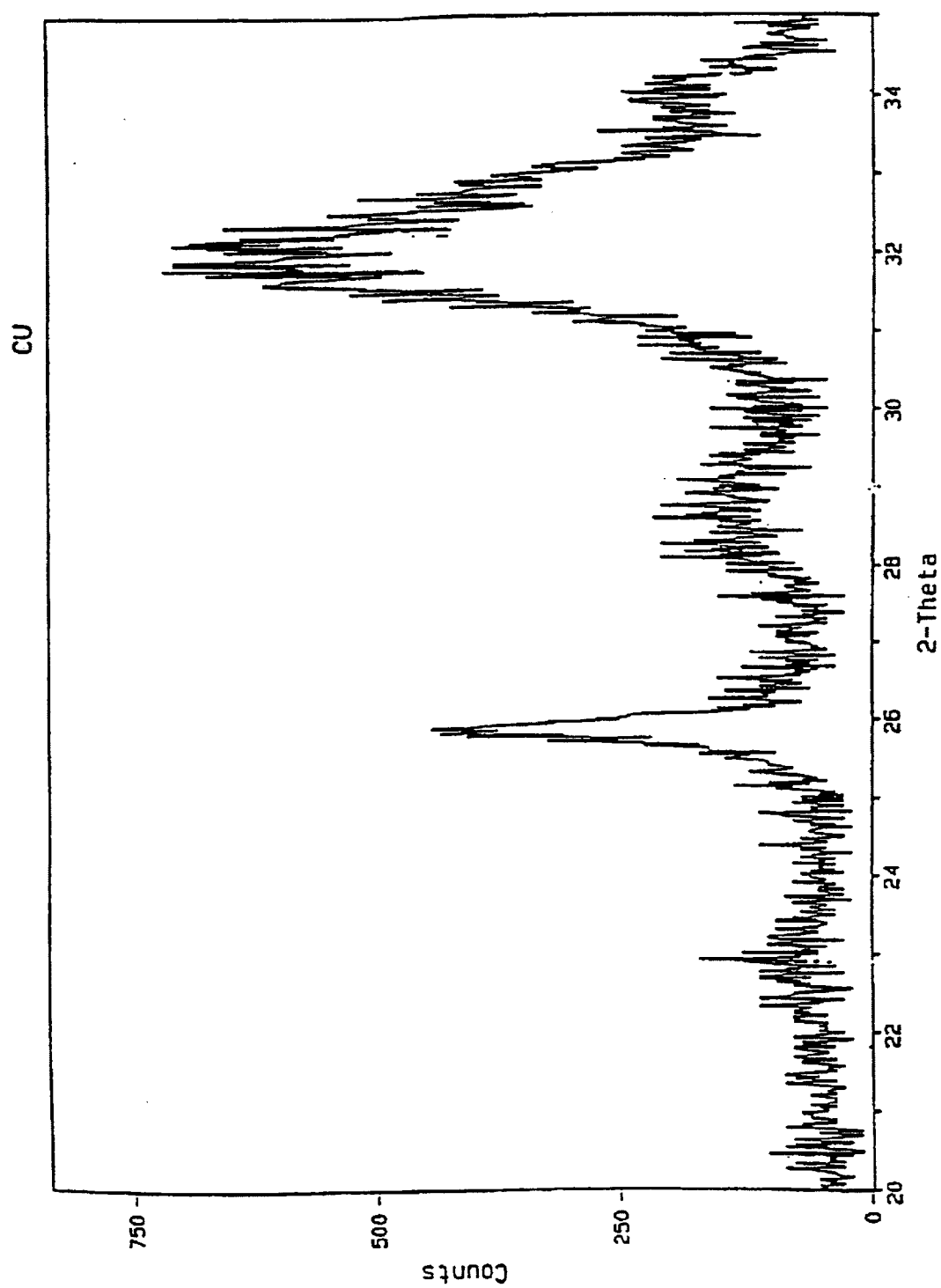
FIG. 15 is an X-ray diffraction pattern of PCA calcium phosphate prepare as described in Example 1–2.
Figure 16:
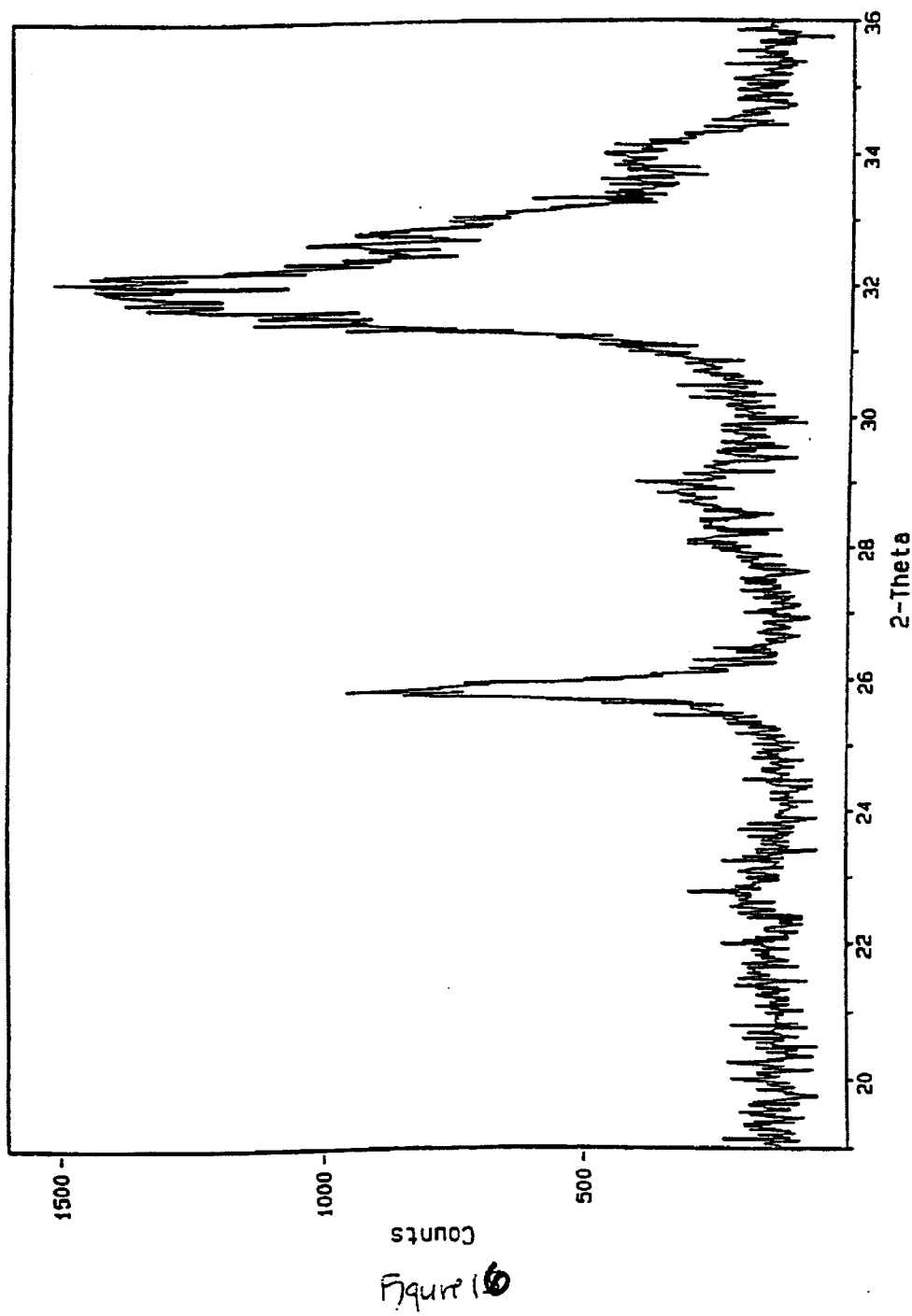
FIG. 16 is and X-ray diffraction pattern of PCA calcium phosphate prepared as described in Example 1–4.

ACP was mixed with the specific promoter at a ratio (wt/wt) of about 50:50 (see Table 1) for 5 minutes in a SPEX laboratory mill. Approximately 0.8 mL H$_2$O/g dry powders were added to the dry precursor mixture and mixed to a paste. The mixture was then shaped into a ball, wrapped in moist tissue paper and heated to 37° C. for at least 30 minutes. After 30 minutes and at various time points thereafter the paste was monitored for hardness. FIGS. 15 and 16 are representative XRD from reactions 1-2 and 1-4. The use of two different grain size hydroxyapatites as participating promoters yielded similar results as with different grain size DCPDs (see Example 5). That is, the larger grain size hydroxyapatite hardened more slowly and less completely than the smaller grain size hydroxyapatite.

Example 35

Use of a Neutreal Apaptitic Calcuim Phosphate Promote

This example demonstrates the use of a neutral apatitic calcium phosphate as a promoter for the conversion of ACP to the inventive PCA calcium phosphate to promote bone growth in vivo. Stoichiometric hydroxyapatite is mixed with reactive ACP as described in Example 34–37. Hydrated precursor paste is applied to animal subjects as described in Examples 14, 15 or 16. Bone healing and biocompatibility is monitored as described at the time points indicated.

Example 36

PCA Material Production Using Promotes

This example demonstrates the production of PCA calcium phosphate from ACP using a number of different passive promoters.

Figure 17:
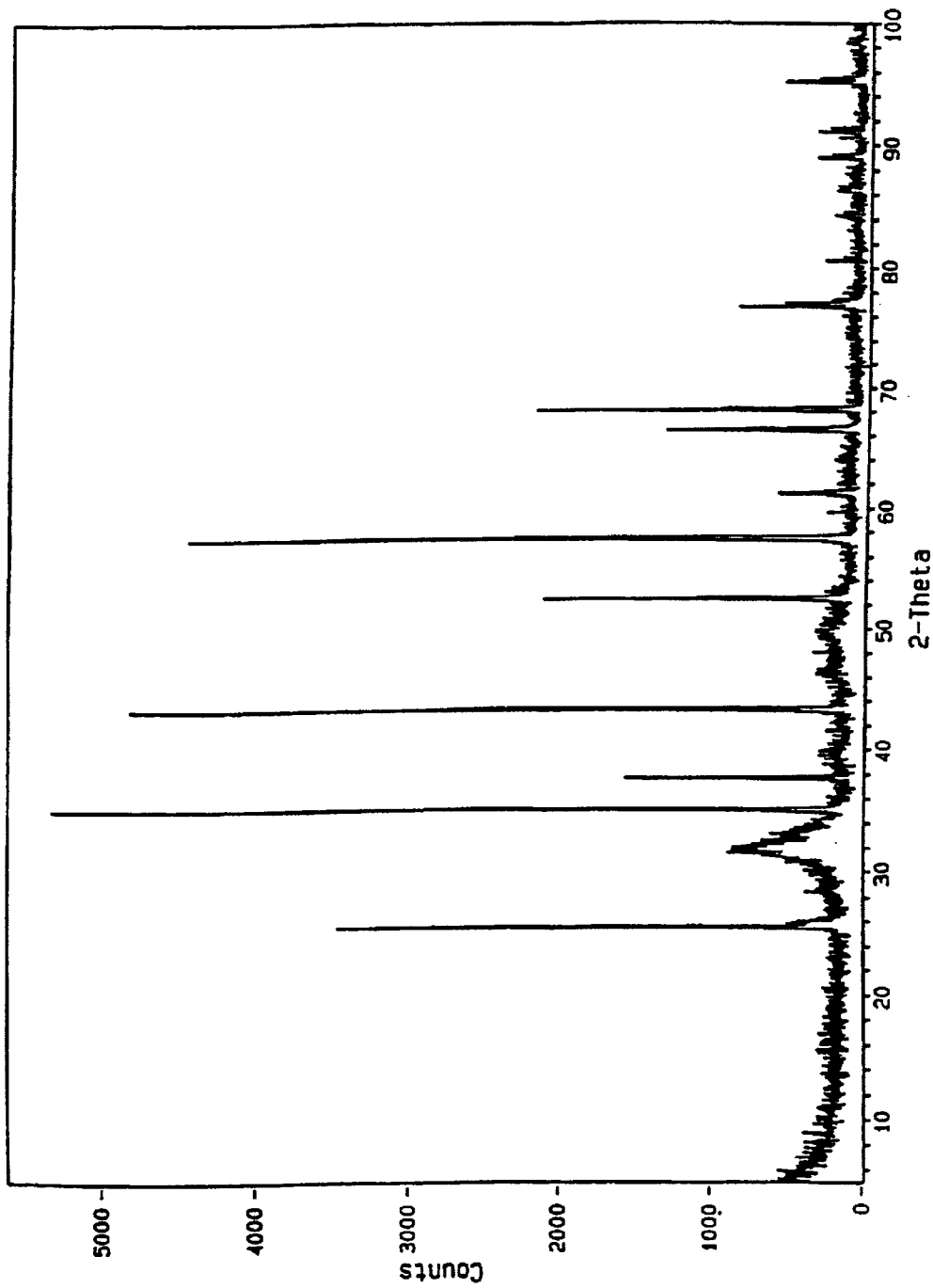
FIG. 17 is an X-ray diffraction patterns of PCA calcium phosphate prepared from $Al_2O_3$ passive promoter, in which $Al_2O_3$ peaks are indicated by lines.

Highly reactive ACP was prepared according to Example 5. ACP was mixed with the specific promoter at a ratio (wt/wt) of about 5:1 or 1:1 (see Table 2) for 5 minutes in a SPEX laboratory mill. Water (0.75–0.85 mL) was added and mixed to form a putty. The mixture was then formed into a ball, wrapped in moist tissue paper and heated to 37° C. for at least 30 minutes. After 30 minutes and at various time points thereafter the paste was monitored for hardness. FIG. 17 is a representative XRD from sample 2-4 employing an alumina promoter. In this figure the alumina peaks can be seen superimposed over the standard PCA calcium phosphate profile.

TABLE 5

ACP Conversion Using Passive Promoters

| study # | Passive Promoter (ACP:promoter) | Incubation time at 37° C. | Extent of Hardening | PCA* of FTIR | PCA* by XRD |
|---|---|---|---|---|---|
| 2-1 | SiO$_2$ (5:1) | 30 min<br>3 hrs | soft<br>very hard | yes | yes |
| 2-2 | Mica (5:1) | 30 min<br>12 hrs | soft<br>very hard | yes | yes |
| 2-3 | Al$_2$O$_3$ (1:1) | 30 min<br>12 hrs | soft<br>very hard | yes | yes |
| 2-4 | Al$_2$O$_3$ (5:1) | 30 min<br>12 hrs | soft<br>very hard | yes | yes |

*PCA = poorly crystalline apatitic calcium phosphate

Example 37

Reaction Profile

This example demonstrates the use of a scanning differential calorimeter (DSC) to monitor temperature sensitivity and the net endothermic nature of a preferred embodiment reaction employing activated ACP and DCPD precursors.

The dry precursor mixture containing equal weights of ACP and DCPD was prepared by mixing in a SPEX 850 laboratory mill with a SPEX 8505 alumina ceramic grinding chamber, ACP and DCPD precursors as described in Example 4, mixing proceeded for 2 min. Preparation of the hydrated prcursor was accomplished by adding from 0.7–1.5 ml of water per gram of mixed dry precursors. Water (0.05 mL), prechilled to approximately 4° C., was added to 47.27 mg of the dry precursor mixture and immediately placed into the calorimeter. The DSC (Perkin Elmer 7 series thermal analysis system) was set to a starting temperature of 0° C. with a scan rate of 5° C./min. The results are shown in FIG. 16. The plot represents a monitoring of the first 7 minutes of reactivity and shows essentially no heat flow between 0.0° C. and approximately 20° C., at which point onset of endothermic heat flow occurs. The heat flow properties indicate that at 37° C. the reaction is essentially endothermic, and under the conditions used, the reaction occurs only very slowly if at all at temperatures below about 20° C. Thus, the net reactivity in the system, that is, the sum of endothermic and exothermic heat flow of the system, is endothermic.

Example 38

Absence of Hardening in Certain Compositions

This example describes the conversion of ACP to PCA calcium phosphate in the absence of a promoter and dem onstrates the failure of the newly formed PCA calcium phosphate to harden. Likewise, promoter DCPD fails to harden or convert on its own.

DCPD and a variety of ACPs and other calcium phosphates were mixed with water and tested for their ability to harden at 37° C. Table 6 summarizes these results, as well as identification of the reaction products, if any, following the test period. Under no circumstances was hardening observed up to 3 days. It was concluded that while conversion of ACP to PCA calcium phosphate may occur, the presence of a promoter is desired to achieve setting and hardening

TABLE 6

ACP conversion in the absence of a promoter

| ACP | $H_2O$ (g) | Incubation | Hardening | FTIR | XRD |
|---|---|---|---|---|---|
| ACP (Example 5) | 0.8 | 30 min | soft | ACP | ACP |
|  |  | 12 hrs | soft | PCA* | PCA* |
| DCPD (Example 8) 38–53 $\mu$m | 0.7 | 30 min | soft | DCPD | ND |
|  |  | 12 hrs | soft | DCPD |  |
| ACP (Example 7) not heat activated | 1.5 | 30 min | soft | PCA* | ND |
|  |  | 12 hrs | soft | HA |  |
| ACP (Example 5) non-carbonated | 1.5 | 30 min | soft | ACP | ND |
| ACP (Example 6) not heat activated | 1.5 | 30 min | soft | ACP | ND |
| ACP (Example 5) non-carbonated; heat activated | 1.5 | 30 min | soft | PCA* | ND |

*PCA = poorly crystalline apatitic calcium phosphate
ND = analysis not done

Example 39

Different Hydrating Agents Effects on Hardening and Final Product

A hydrated precursor (ACP and DCPD) was prepared as described in Examples 4, 5 or 37 or 10, with the exception that a variety of hydration media were used. Samples were then tested for hardness and completeness of reaction at various time points. In all cases, 1 g of the mixed precursors were hydrated with 0.75–1.0 mL of hydration medium to produce a paste. Table 7 summarizes the results and demonstrates that a variety of aqueous based liquids, and in particularly physiologically acceptable media, may be used in the preparation of PCA calcium phosphate.

TABLE 7

Effect of Hydrating Agents

| Hydration Medium | Incubation Time | Hardening |
|---|---|---|
| Tris | 30 min | hard |
| 0.9 M NaCl | 30 min | hard |
| MEM | 30 min | hard |
| MOPS | 30 min | hard |
| HEPES | 30 min | hard |
| BUFFERALL | 30 min | hard |
| PBS | 30 min | hard |

Example 40

Analysis of Hardening

The porosity of a hardened sample of PCA calcium phosphate prepared according to Example 5 was determined.

A hardened sample of PCA calcium phosphate (1 g) was weighed immediately after removal from the moist incubator, and then air dried at room temperature for 12 hrs. The dried sample was carefully weighed and then the volume was calculated. The sample was placed into a 20 mL sample of water. After 1 minute the approximate displacement volume was noted. The dried sample was found to absorb up to 50–60% of its dry weight in $H_2O$. These results are interpreted to mean that the sample is up to 50–60% porous. Density was approximated at 1.65 g/cm$^3$.

Example 41

Use of Resorbable Polymer to Promote Conversion

This example demonstrates the use of a resorbable polymer to promote the conversion of ACP to PCA calcium phosphate.

Granular PLLA is prepared and sieved to a size of 100 $\mu$m. The powder thus obtained is mixed with the ACP (5:1 ACP:PLLA) of Example 37 and ground for 5 minutes in a SPEX laboratory mill. Water is added to 1 g of the mixture to form a workable paste. The paste is shaped into a ball and is heated to 37° C. in a moist environment for 1 hour. The hardened sample is analyzed using FTIR and XRD.

Example 42

Sub-Ambient Hardening Characteristics

This example investigates the hardening characteristics of the hydrated precursor at sub-ambient temperatures.

Hydrated precursor was prepared with water as described in Example 37 and then tightly sealed to avoid evaporative loss either in parafilm or in an aluminum tube. The samples were then held for up to 1 hr, 24 hrs and 6 days. At the indicated time points, the hydrated sample was removed from refrigeration placed in a moist environment at 37° C. In all instances the samples hardened within 30 minutes.

Example 43

Room Temperature Hardening

This example demonstrates the effect of maintaining the hydrated precursor uncovered at room temperature.

The dry precursor was prepared as described in Example 6 except C. The dry precursor was mixed with the indicated amount of water and tested for hardening and injectability through a 16 gauge needle after standing uncovered at room temperature for various time periods. The results are reported in Table 8.

TABLE 8

Paste Injectability after Standing at Room Temperature.

| sample wt (g) | water added (mL) | mixing time (s) | standing time (min) | room temp. (° C.) | injectability for 16 gauge needle | hardening; 30 min/ 37° C. |
|---|---|---|---|---|---|---|
| 1 | 0.8 | 20 | 10 | 25 | v. good | v. good |
| 1 | 0.8 | 20 | 20 | 24 | v. good | v. good |
| 1 | 0.8 | 20 | 30 | 25 | v. good | v. good |
| 1 | 0.8 | 20 | 40 | 25 | good | v. good |
| 1 | 0.8 | 20 | 50 | 24 | poor | v. good |
| 5 | 4.2 | 40 | 10 | 24 | v. good | v. good |
| 5 | 4.2 | 40 | 20 | 25 | v. good | v. good |
| 5 | 4.2 | 40 | 30 | 25 | good | v. good |
| 5 | 4.2 | 40 | 40 | 25 | poor | v. good |

The results demonstrate that a one gram sample may be stable as an injectable paste at ambient conditions for up to 45 minutes and that a 5 gram sample may be stable as an injectable paste for up to 30 minutes at ambient conditions (in air, 25° C.).

Example 44

Compressing Precursors Using Hydraulic Pess

This example illustrates the method of preparing a pellet with a hydraulic press.

A Carver Laboratory Press is used. A specific amount of powder is measured by weight. The powder is then placed into the die set mold. The height or thickness is determined in part by the amount of material used in the mold. Once the material is in the die set, the mold is placed onto the hydraulic press. A desired load is set on the press. The material is then compressed for a specific amount of time. After the time has elapsed, the resulting pellet is expelled from the die set into a holding container.

A 0.5 g sample, ID=AB com1, from lot AB971002 was compressed at 500 psi (pounds per square inch) for 5 minutes in the Carver Laboratory Press. The physical aspects of the resulting pellet were diameter=13 mm, height=3 mm, and the density was 1.27 g/cm3. The mechanical strength was described as hard and capable of being broken by hand. After FTIR analysis, the pellet was 70% PCA in wet tissue, 90% PCA in 20 ml distilled water, and 100% PCA in carbonated buffered solution (CO3 −2 0.2 mol). A second sample of 0.5 g, ID=ABcom2, from lot AB971002 was compressed at 4700 psi for 5 minutes in the Carver Laboratory Press. The pellet had the following results: diameter=13 mm, height=2 mm, and the density is 1.99 g/cm3. The mechanical strength was described as very hard and capable of being broken by hand. When the pellet was incubated at 37 C. for 60 hours and analyzed through FTIR analysis, the following results were found: 60% PCA in wet tissue, 60% PCA in 20 ml distilled water, and 60% PCA in carbonated buffered solution (CO3 −2 0.2 mol).

Example 45

Compressing Precursors Using Hand-held Press

This example demonstrates the method of preparing a pellet with a hand-held press.

A Perkin Elmer Quick Press is used. Pellets 7 mm in diameter are made using the selected die sets in conjunction with the Quick Press. Other die sets of various diameters can also be used depending on the desired measurements. The surface of the pellet can be flat or rounded, depending on the shape of the mold. The sample is loaded into the selected die mold. As the amount of sample increases, the thickness of the pellet also increases. Next, a reference position is selected from the various manual positions set on the top of the Quick Press. The die set is placed in position in the Quick Press. A steady pressure is applied to the handle of the Quick Press for a selected amount of time. Once the time has expired, the pellet is removed from the mold by removing the bottom cap from the die set and applying pressure to the top die in order to expel the pellet from the die set.

A 0.08 g sample, ID: AB com3, of AB from lot AB971002 was measured into the 7 mm diameter die set. The Quick Press manual position was set at 20 and compressed for 1 minute. The resulting pellet had a diameter of 7 mm and a height of 1.5 mm; the density was 1.39 g/cm3. A second sample, ID: AB com4, of 0.1 g of AB from lot AB971002 was measured into the 7 mm diameter die set. The manual position was set at 20 and compressed for 30 seconds in the Quick Press. A resulting pellet was formed with a diameter of 7.0 mm and height of 2.0 mm; the density was 1.23 g/cm3.

Example 46

Behavior of PCA Pellets with Different Media

This example describes the behavior of PCA calcium phosphate pellets in different medias.

The four kinds of media chosen were: (−MEM (Minimum Essential Medium); TBS (Tris Bovine Serum: 50 mM of Tris+150 mM of NaCl); (−MEM+FBS (Fetal Bovine Serum 10%); and Complete Media (immersion for 2 h in TBS at 37 C. and subsequent immersion into the (−MEM+FBS).

A 0.3 g sample of mixed precursors ACP and DCPD was compressed for one minute at 7 tons using the Carver Laboratory Press. The resulting pellet (a) had a diameter of 12 mm and a height of 1 mm. The pellet was put into 10 ml of distilled water at 37° C. for 30 minutes. After incubation, the pellet was put in the 6 ml of different media at 37° C. for 24 and 48 hours.

A second 1 g sample of mixed precursors ACP and DCPD was combined with 0.8 ml of distilled water. The mixture was rolled into a ball and dropped into 10 ml distilled water at 37° C. for 30 minutes. The ball was then ground using a mortar and pestle to obtain a fine powder. The powder was pressed for one minute at 7 tons using a Carver Laboratory Press. The resulting pellet (b) had a diameter of 12 mm and a height of 1 mm. The pellet was then put into the different media at 37 C. for 24 and 48 hours.

The pH of the solution of media was measured (at 25 (C.) at different times of 0, 24, and 48 hours after incubation at 37° C. The results of this study are displayed in Table 9.

TABLE 9

| Sample | α-MEM | | | TBS | | | α-MEM + FBS | | | Complete | | |
|---|---|---|---|---|---|---|---|---|---|---|---|---|
| Preparation | 0 h | 24 h | 48 h | 0 h | 24 h | 48 h | 0 h | 24 h | 48 h | 0 h | 24 h | 48 h |
| a | 7.6 | 8.1 | 7.9 | 7.5 | 7.0 | 6.8 | 7.5 | 7.7 | 8.2 | 7.6 | 7.9 | 7.9 |
| b | 7.3 | 7.3 | 7.1 | 7.3 | 6.5 | 6.0 | 7.4 | 7.5 | 7.5 | 7.5 | 7.5 | 7.3 |

Example 47

Reacting Precursors, Lyopholizing, Crumbling, Compressing

This example illustrates how a pellet is formed from PCA calcium phosphate paste.

PCA is made using ACP and DCPD, as the promoter. Saline is used as the biologically suitable aqueous medium. The prepared PCA paste is then lyophol hardened in vitro at 37° C. and subsequently lyopholized. The hardened PCA material is then crumbled by hand. Once crumbled, the PCA material is formed into a pellet by methods described in examples 34 and 35.

Example 48

Shaping, Hardening, Lyopholizing Without Grinding

This example shows how a pellet is formed from PCA calcium phosphate paste.

ACP and DCPD are selected as the precursors. An appropriate amount of Saline is used to make a PCA paste. The PCA paste is shaped into the desired form. It is then incubated at 37° C. in vitro for 30 minutes. The hardened object is then lyopholized.

Example 49

In Vivo Experiments Comparing the Methods

This example compares the methods of producing the pellets through in vivo experimentation.

Pellets are made according to Example 32. Two pellets are implanted into a dog femur. The animals are sacrificed and the implantation sites are analyzed for remaining residual material at time points of 3, 4 and 6 weeks. At each time point, decalcified and undecalcified slides of the implantation site are prepared and stained. These slides are histomorphometrically analyzed to determine the similarity of the prepared pellets to that of PCA calcium phosphate paste.

Example 50

Incorporation of a Filler or Binder

This example demonstrates the use of a filler to study plastic flow, with particular interest in the effect of tensile strength in the pellet.

A compressible sugar is used as a filler in conjunction with pellet production. The sugar is mixed with the precursors ACP and DCPD in a ratio of 1:1:1 before compression. The pellet is produced according to example 1 with modifications in the duration of the total compression cycle and the duration of the maximum compressive force. The effectiveness of the sugar filler is measured by comparing the tensile strength of the pellets. The equation used to computer tensile strength is:

$$\sigma_0 = 2F/\Pi dt,$$

where $\sigma_0$ is the tensile strength, F is the force needed to cleave the tablet, d is the diameter of the pellet, and the t is the tablet thickness or height.

Example 51

Delivery of a Vaccine in a Pellet

This example explains how the pellet is used as a delivery vehicle for a vaccine.

Keyhole limpet hemocyanin is prepared at a concentration of 0.5 mg/ml in phosphate buffered saline pH 7.0, 0.8 ml of this solution is added to 1 g of a 1:1 mixture of activated ACP and DCPD and mixed into a putty. The prepared PCA putty is then lyopholized. The dry material is milled for 10 minutes into a powder using a SPEX 8510 laboratory mill with a SPEX 8505 alumina ceramic grinding chamber. The powdered PCA is then prepared in a pellet as described in Example 32. A pellet formed by Example 32 is implanted subcutaneously in a rat. The process is repeated on a monthly basis for four months. Blood samples are taken on a regular basis and anti-Keyhole limpet hemocyanin antibody titers are determined by ELISA.

Example 52

Canine Anterior Lumbar Interbody Fusion

This example describes the use of PCA calcium phosphate in the fusion of canine spinal vertebrae.

Animals were anesthetized as described in Example 26, positioned in the right lateral decubitus position, shaved from anterior to posterior midline, extending form mid thorax to the pelvis. Following sterile prep and drape, a standard left retroperitoneal approach to the anterior lumbar spine was performed, with exposure of the L3–L6 vertebrae. The segmental vessels overlying L4 and L5 were ligated and divided, allowing anterolateral exposure of the L3-4, L4-5 and L5-6 discs. Anterior discectomies were performed at each level with the endplate prepared parallel and to bleeding subchondral bone using a parallel-paired-bladed oscillating saw (Aesculap). Following discectomy, a cylindrical titanium cage containing either PCA calcium phosphate or autologous bone or an unfilled cage was inserted into each disc space. Autogenous iliac crest bone graft was harvested from the left anterior iliac crest through a separate incision just prior to its packing into the cage and insertion into the disc space. After all three cages were inserted, internal fixation was applied using 4.5 mm vertebral body screws and a 6 mm diameter longitudinal rod from L3 to L6. Closure of the abdominal wound and iliac crest graft site was then done in layers using absorbable sutures and skin staples.

Dogs are sacrificed at two and twelve weeks and the histology of undecalcified sections are examined for evidence of new bone growth and vertebral fusion. Upon visual inspection or explant, the spinal cords using the PCA calcium phosphate of the invention appeared fused.

Example 53

Bone Healing in the Presence of PCA Material

The purpose of this study was to examine bone healing in the presence of the invented PCA material.

For this study, 30 adult NZW rabbits were used. Tap water and pellets of certified rabbit chow were available ad libitum throughout the course of the study. Surgical procedures were performed under full anesthesia and aseptic conditions. Cefazolin was then administered (22 mg/kg) 30 minutes before the surgery. The anesthesia consisted of 10 ml (100 mg/ml) ketamine, 1 ml (100 mg/ml) xylazine, and 5 ml of 0.9% physiologic saline (87.5 mg/kg ketamine, 8.75 mg/kg xylazine). The anesthetic cocktail was given at a dose level of 1.4 ml/kg i.m. The animalÆs hind limb was then clipped free of hair, and washed with a Betadine surgical solution and alcohol. Before the surgery the animal was monitored to be sure that it was properly anesthetized. To do this, pressure was applied to the foot pad. Once the animal was no longer responsive, further anesthesia ceased. Throughout the procedure the animal was monitored for whisker twitching, which would indicated revival of the animal. Using an aseptic technique, an incision was made over the proximal tibia. The soft tissue was deflected away and the bone was exposed. An 8 mm trephine dental handpiece at low speed was used for irrigation (0.9% physiologic saline) as needed. The bony disc was dissected free, and then the site was prepared for implantation. The PCA material was then placed into the defect. The soft tissues were closed in layers with 3-0 Dexon™ suture material. One sample per animal was performed using this method. The animals were monitored and given buprenorphine (0.02–0.05 mg/kg, s.c.) and a broad spectrum antibiotic upon awakening. The analgesic and antibiotic were administered 2 times per day for three days after surgery. Blood was drawn from each animal prior to euthanasia. The method used to draw blood was as follows: Acepromazine (1 mg/kg s.c.) was given to each animal to relax the animal and to dilate the vessels approximately 15–20 minutes before drawing the blood. Next, a 23 g butterfly needle was placed in the central ear artery.

A vacutainer set up with 2 cc glass tubes was used to draw no more than 2 ml of blood from the animal. The needle was removed after the blood was drawn and pressure was placed on the vessel to allow for proper clotting. Furthermore, intra-muscular injections were administered during the surgical procedure while the animal was under full anesthesia. The soft tissue site was then shaved and prepped for injections of type 10.0 PCA material. 3–5 injections into the lumbar muscle were made using a 16 gauge hypodermic needle. 4 or 5 injections were given to the rabbits at 4, 7, and 14 day time-points to allow for PCA material recovery for chemical analysis. The remaining time-points had only 3 injections. Each injection contained approximately 0.2 grams of the PCA material. On the contralateral side, 3 injections were made of a resorbable suture material which acted as the positive control. The animals were euthanized by intravenous anesthesia with sodium pentobarbital followed by exsanguination by incision of the axillary arteries. For FTIR and XRD analysis, the PCA material was removed from the soft tissue implant sites, snap frozen in isopentane and stored in a −70° C. freezer prior to shipment to ETEX Corporation on dry ice. Soft and hard tissue test sites were removed and prepared for histology.

After euthanasia and exsanguination, tissues were removed from the animals, embedded in paraffin, sectioned and stained with hematoxylin and eosin for histopathological sections. Next, 300 mg of retrieved PCA material were analyzed in a Rigaku RU300 rotating-anode X-Ray diffractometer at the Center for Materials Science and Engineering facilities at the Massachusetts Institute of Technology in Cambridge, Mass. on Jan. 22, 1997. A homogeneous mixture of 300 mg of KBr and 1.5 mg of retrieved PCA material were analyzed by a Spectrum 1000 Perkin Elmer FTIR. Also, sections of tissue were scored for endosteal bone formation on a scale of 0 to +3. Areas with neutrophilic infiltrates generally had little osteoprogenitor or new bone formation. On a scale of 0 to +3, with 0 being no new endosteal bone formation and +3 being extensive new endosteal bone formation, animals at day 4 had 0 to +1, those at day 7 had +1, and at day 14 had +2.

At day 4 and 7 there was visible, slight swelling over the defect site. Gross findings at Day 14 displayed the development of a dome shaped bony callus over the drill site. There was an increased maturity of the bony callus at the defect site for all test groups when evaluated at day 21, and a lack of any significant periosteal reaction over the remaining cortex. Microscopically, the defect site was filled with trabecular and cortical bone. There was a moderate amount of endosteal trabecular bone formation around and extending into the PCA material. At day 21 there was no indication of any adverse reaction to the implanted PCA material. Samples were retrieved at days 4, 7, and 14 and analyzed using XRD. See Figure __. These spectra confirmed the following: The crystalline structure of PCA material is stable for at least 14 days in vivo, and is substantially the same as in vitro prepared PCA material. Additionally, samples were retrieved from animals at days 4, 7 and 14 and analyzed by FTIR. See Figure __. The test material was chemically stable, and the reaction was completed in vivo. PCA material caused no unacceptable inflammatory response when implanted either intramuscularly or in a bony defect site. Through XRD and FTIR analysis, PCA material was determined to be chemically stable in vivo for up to 21 days following implantation.

Example 54

Quantification of Bone Healing with PCA Material

The Objective of this study was to quantify bone healing in the presence of the inventive PCA, and to monitor the resorption of the implanted PCA material.

The protocol was signed on Feb. 14, 1996 and the study was performed at Bio-Research Laboratories Ltd., 87 Senneville Rd., Senneville, Quebec, Canada, H9X 3R3 in accordance with the United States FDA Good Laboratory Practice Regulations (21 CFR Part 58). Surgeries were performed on Feb. 15, 16, 22, 23, 29 and March 1996 (for the 6 month study) and Apr. 11 and 12, 1996 (for the 1-year study).

Beagle dogs (*canis familiaris*), were obtained from HRP Inc., 6321 South 6th Street, Kalamazoo, Mich. 49009 U.S.A. The dogs were housed individually in stainless-steel cages each equipped with a bar type floor and an automatic watering valve in 4 separate rooms. All animals had access to a standard certified pelleted commercial dog food (400 g—PMI Certified DogChow 5007: PMI Feeds Inc.) once daily and the bowls remained in the cages for approximately 24 hours (except during designated procedures). In addition, some animals occasionally received a diet supplement of canned food, Mixit or Canine ID (Hill's Science Diet). Municipal tap water was provided ad libitum.

The PCA material was supplied as a sterile powder in pre-measured packages. The material was prepared on the day of surgery for implantation. The material was hydrated with appropriate amounts of sterile water and stored covered at room temperature prior to implantation. Each dog received a dose of Penlong-XL (Benzathine penicillin G and Procaine penicillin G) (1 mL) intramuscularly at least 1 hour prior to surgery and again 2 days following surgery. Each animal was pre-anesthetized with an intramuscular injection of AC-Promazine (0.05 mg/kg), Butorphanol (0.2 mg/kg) and Glycopyrrolate (0.01 mg/kg) at least 10 minutes prior to presurgical preparation. The animals were then prepared for surgery by shaving one (Group 1 and 2) or both (Groups 3 and 4) hindlimbs from the pelvis to the lower leg. The shaved area was washed with Hibitane™ (Chlorhexidine gluconate 4%) followed by a liberal application of 70% isopropanol and Betadine™ (Povidone iodine 10%). The animals were anesthetized with an intravenous injection of thiopentone sodium 2.5% and the subcutaneous injection site (mid-dorsal thoracic region) for Group 2 was prepared in the same manner. Prior to surgery, Duratears™ ointment was administered to each eye. All animals were intubated and maintained under isoflurane anesthesia for the surgical procedure. Lactated Ringer's (at a rate of 10 mL/kg/hour) was administered perioperatively.

A longitudinal skin incision was made along the lateral surface of the hindlimb to expose approximately 8–10 cm of the femur. The periosteum overlying the femur was reflected from the bone. A template (measuring 6 cm) was applied identifying the sites for the holes which were drilled at either end of the shaft. Using an appropriately sized drill bit, a piece of bone approximately 3–5 mm deep was removed from each end of the shaft and using an oscillating saw, this hole was elongated distally for approximately 4–5 cm. The marrow was removed and any significant bleeding was appropriately controlled. For Group 1 animals, following creation of the defect site, the bone removed was cut into small pieces, rinsed with saline and packed into the defect site as the autologous bone application. For Group 2 animals, following creation of the defect site the bone substitute material was placed into the defect site, ensuring that no excess amount of material was left in the surrounding tissues. Following this procedure, a quantity of a__-a__ BSM™ (to make up 25 g, total dose) was injected subcutaneously in the mid-dorsal thoracic region. In the case of Group 3 and 4 animals, following creation of the defect site on the first hindlimb, the bone substitute material was placed into the defect site, ensuring that no excess amount of material was left in the surrounding tissues. The bone removed was cut into small pieces and rinsed with saline. A defect site was created in the opposite limb and the prepared bone was placed in the site. Each defect site was marked by placing a 1 mm piece of K-wire at each end of the groove. The fascia was then sutured closed with resorbable suture to ensure the material remained in place. The surgical site was closed with surgical staples and the staples were removed approximately 10 days after surgery.

Radiography was performed on both hindlimbs of each animal from Group 3 on the day of necropsy of Week 0, and on all surviving Group 3 animals in Week 3, 12 and 26. Animals were sedated for the procedure. The animals were euthanized by intravenous anesthesia with sodium pentobarbital followed by exsanguination by incision of the axillary arteries. The tissues indicated above were prepared by embedding in paraffin wax, sectioning and staining with hexatoxylin and eosin. Half of each femoral implantation site (Groups 1, 2 and 4) was prepared as a decalcified section and prepared as hematoxylin and eosin and Masson's trichrome stained slides. The remaining half of each site was retained in 70% alcohol and prepared as an undecalcified section (in appropriate embedding media) and stained with von Kossa and Goldner's Trichrome while fixed in Zenker's fluid.

Following histopathology analysis, histomorphometric analysis was performed. Defect boundaries were determined subjectively and total area of bone and the PCA material present were tabulated for the region of the defect. Histomorphometry confirmed and extended the histopathology. Histomorphometric data from all von Kossa stained undecalcified sections, for all available experimental groups were pooled at each time point according to implant type independent of whether the animals were from group 1, 2 or 4. Results for new bone formation in both PCA material and autograft treated defects, as well as PCA material resorption, and are presented in Figure __. New bone formation in autograft recipients appeared to occur slightly in advance of new bone formation in PCA material recipients. At four weeks new bone in autograft recipients reached a near maximum value of 74.7%+/−20 (sem; n=8). By week 26 autograft values had decreased to 56.78%+/−20.9 (sem; n=4) suggesting that increased remodeling was occurring perhaps due to failure of some graft regions. While new bone did not reach its maximum value (77.18%+/−11.2, sem; n=8) until week 12 in the PCA material recipients, the apparent remodeling observed in autografts at 26 weeks was not observed in the PCA material recipients. The PCA material values at week 26 (78%+/−21.5, sem; n=4) were comparable to the 12 week values. Observable residual PCA material represented less than 95% of the entire surface area in the defect by week 4 and less than 0.3% by week 26. Since the defect was originally 100% filled with PCA material, resorption was greater than 99% by week 26.

Other Embodiments

It will be understood that the foregoing is merely a description of certain preferred embodiments of the invention and is not intended to be limiting thereof. The following claims cover all of the generic and specific features of the invention herein described in the text and accompanying drawings.

What is claimed is:

1. A bioresorbable implant composition comprising:
   a calcium phosphate;
   a first agent that directly or indirectly stimulates osteoclast activity, wherein said first agent modulates the resorption of the calcium phosphate at an implant site; and
   a second agent that is biologically active, wherein said first and second agents are different.

2. The implant composition of claim 1 wherein said first agent is selected from the group consisting of interleukin-1, colony stimulating factors, macrophage-colony stimulating factors, transforming growth factor α, tumor necrosis factor, interleukin-6, interleukin-11, interleukin-3, para-thyroid hormone, vitamin D metabolites, prostaglandins, and oxygen free radicals.

3. The implant composition of claim 1 further comprising at least one bone-resorbing cell.

4. The implant composition of claim 3 wherein the at least one bone-resorbing cell is selected from the group consisting of a progenitor cell, a stem cell, an osteocyte, an osteoclast, an osteoblast, a chondrocyte, a macrophage, a myoblast, a fibroblast, a bone- or cartilage-producing cell, a muscle cell, an hepatocyte, a parenchymal cell, a cell of intestinal origin, a nerve cell, and a skin cell.

5. The implant composition of claim 1, wherein said second agent is selected from the group consisting of anti-AIDS substances, anti-cancer substances, antibiotics, antiseptics, ACE inhibitors, adrenergic antagonists, antacids, immunosuppressants or immunomodulatory factors, anti-viral substances, enzyme inhibitors, neurotoxins, neurotransmitters, opiods, hypnotics, antihistamines, lubricants, tranquilizers, anti-convulsants, muscle relaxants, anti-Parkinson substances, anti-spasmodics, muscle contractants, anti-diarrheals, anti-emetics, laxatives, diuretics, miotics, anti-cholinergics, anti-glaucoma compounds, anti-parasite compounds, anti-protozoal compounds, anti-hypertensives, analgesics, anti-pyretics, anti-inflammatory agents, anti-tussive agents, anti-vertigo medications, antinertigic medications, anti-motion sickness medications, local anesthetics, ophthalmics, prostaglandins, anti-depressants, anti-psychotic substances, imaging agents, specific targeting agents, trophic factors, growth factors, neurotransmitters, cell response modifiers, vaccines, compounds that enhance or allow ingrowth of the lymphatic network or nerve fiber, an endothelial growth factor (EGF), vitamins, hormones, and nucleic acids.

6. The implant composition of claim 1 wherein the calcium phosphate comprises a powder mixture of:

an amorphous calcium phosphate having a calcium to phosphate ratio (Ca:P) of 1.1:1.0 to 1.9:1.0; and a calcium phosphate promoter selected to promote conversion of the amorphous calcium phosphate into a bioresorbable poorly crystalline apatitic (PCA) calcium phosphate.

7. The implant composition of claim 6 further comprising:

a physiologically acceptable aqueous solution in an amount sufficient to hydrate the calcium phosphate and to form a calcium phosphate paste or putty.

8. The implant composition of claim 7 wherein the physiologically acceptable aqueous solution is selected from the group of water, buffered pH solution, saline solution, serum and tissue culture medium.

9. The implant composition of claim 6 wherein the calcium phosphate promoter comprises an acidic calcium phosphate.

10. The implant composition of claim 9 wherein the acidic calcium phosphate is selected from the group of calcium metaphosphate, dicalcium phosphate dihydrate, heptacalcium decaphosphate, tricalcium phosphate, calcium pyrophosphate dihydrate, crystalline hydroxyapatite, calcium pyrophosphate, monetite, octacalcium phosphate, and poorly crystalline apatitic (PCA) calcium phosphate.

11. The implant composition of claim 1 wherein the overall calcium to phosphate ratio (Ca:P) of the calcium phosphate is less than 1.5:1.0.

12. The implant composition of claim 6 wherein the amorphous calcium phosphate and the calcium phosphate promoter are present in about equal amounts by weight.

13. The implant composition of claim 6 wherein the calcium phosphate promoter comprises dicalcium phosphate dihydrate (DCPD).

14. The implant composition of claim 1, wherein at least about 80% of said implant composition is resorbed within twelve months.

15. The implant composition of claim 1, wherein at least about 80% of said implant composition is resorbed within nine months.

16. The implant composition of claim 1, wherein at least about 80% of said implant composition is resorbed within six months.

17. The implant composition of claim 1, wherein at least about 80% of said implant composition is resorbed within three months.

18. The implant composition of claim 1, wherein at least about 80% of said implant composition is resorbed within one month.

\* \* \* \* \*

UNITED STATES PATENT AND TRADEMARK OFFICE
CERTIFICATE OF CORRECTION

PATENT NO. : 6,972,130 B1
APPLICATION NO. : 09/284436
DATED : December 6, 2005
INVENTOR(S) : Dosuk D. Lee et al.

It is certified that error appears in the above-identified patent and that said Letters Patent is hereby corrected as shown below:

On Title page
Item 56
On Page 2, Under References Cited, Under OTHER PUBLICATIONS, Under Clarke et al., replace "Non-Sterodial" with --Non-Steroidal--.

Item 56
On Page 2, Under References Cited, Under OTHER PUBLICATIONS, Under Dennissen et al., replace "hysroxyapatite" with --hydroxyapatite--.

Item 56
On Page 3, Under References Cited, Under OTHER PUBLICATIONS, Under Onodera et al., replace "Inhabitory" with --Inhibitory--.

Column 1,
    Line 10, replace "bipharmaceutics" with --biopharmaceutics--.
    Line 15, replace "delivery" with --deliver--.
    Line 61, replace "Ijntema" with --IJntema--.

Column 2, Line 12, replace "WO 94/25080." with --WO 94/25080).--.

Column 4,
    Line 1, replace "enhances" with --enhance--.
    Line 45, replace "Preferable" with --Preferably--.
    Line 56, replace "22  95%" with --95%--.

Column 5,
    Line 7, replace "of biologically" with --of a biologically--.
    Line 40, replace "nervours" with --nervous--.
    Line 44, replace "Preferably, the at" with --Preferably, at--.
    Line 59, replace "a natural" with --at natural--.

Column 6, Line 65, replace "rabitts" with --rabbits--.

Column 7, Line 14, replace "bread" with --breadth--.

UNITED STATES PATENT AND TRADEMARK OFFICE
CERTIFICATE OF CORRECTION

| | | |
|---|---|---|
| PATENT NO. | : 6,972,130 B1 | |
| APPLICATION NO. | : 09/284436 | |
| DATED | : December 6, 2005 | |
| INVENTOR(S) | : Dosuk D. Lee et al. | |

It is certified that error appears in the above-identified patent and that said Letters Patent is hereby corrected as shown below:

Column 8,
        Line 53, replace "sources)," with --sources)--.
        Line 56, replace "reaction" with --reactions--.
        Line 57, replace "accelerate at 37°c." with --accelerate at 37°C.--.
        Line 63, replace "powder is" with --powder, is--.

Column 10,
        Line 20, replace "art generally" with --art are generally--.
        Line 22, replace "constrast" with --contrast--.
        Line 48, replace "sate" with --state--.
        Line 61, replace "results in a vacancies" with --results in vacancies--; and
        Line 63, replace "possess" with --possesses--.
        Line 66, repalce "stoichmetry" with --stoichiometry--.

Column 12,
        Line 27, replace "Is recognized" with --It is recognized--.
        Line 43, replace "maintain" with --maintains--.

Column 14, Line 20, replace "Man" with --Many--.

Column 15,
        Line 61, replace "of the may" with --of the hydrated precursor may--.
        Line 43, replace "remodelling" with --remodeling--.

Column 16, Line 65, replace "of the of the" with --of the--.

Column 19, Line 26, replace "Chloinergic" with --Cholinergic--.

Column 20, Line 42, replace "Anti-hypertensives" with --Antihypertensives--.

Column 21, Line 39, replace "interluekins" with --interleukins--.

Column 22, Line 38, replace "it's" with --its--.

Column 25, Line 1, replace "is" with --are--.

Column 32, Line 56, replace "the field. "The" with --the field, "the--.

Column 42, Line 23, replace "area" with --areas--.

UNITED STATES PATENT AND TRADEMARK OFFICE
CERTIFICATE OF CORRECTION

| | |
|---|---|
| PATENT NO. | : 6,972,130 B1 |
| APPLICATION NO. | : 09/284436 |
| DATED | : December 6, 2005 |
| INVENTOR(S) | : Dosuk D. Lee et al. |

It is certified that error appears in the above-identified patent and that said Letters Patent is hereby corrected as shown below:

Column 44, Line 31, replace "there" with --their--.

Column 52, Line 44, replace "prcursor" with --precursor--.

Column 53, Line 14, replace "hardening" with --hardening.--.

Column 58, Line 62, replace "inserted," with --inserted;--.

Column 63, Line 4, replace "an" with --a--.

Signed and Sealed this

Twentieth Day of May, 2008

JON W. DUDAS
*Director of the United States Patent and Trademark Office*